United States Patent [19]

Stalker et al.

[11] Patent Number: 5,750,875
[45] Date of Patent: May 12, 1998

[54] GLYCOGEN BIOSYNTHETIC ENZYMES IN PLANTS

[76] Inventors: David M. Stalker, 2736 Cumberland Pl., Davis, Calif. 95616; Christine K. Shewmaker, 1409 Spring Creek, Woodland, Calif. 95695; Janette V. Oakes, 2408 Amapola Dr., Davis, Calif. 95616

[21] Appl. No.: 469,202

[22] Filed: Jun. 6, 1995

Related U.S. Application Data

[63] Continuation-in-part of Ser. No. 536,392, Jun. 11, 1990, abandoned, and a continuation of Ser. No. 16,881, Feb. 11, 1993, which is a continuation-in-part of Ser. No. 735,065, Jul. 24, 1991, Pat. No. 5,349,123, which is a continuation-in-part of Ser. No. 632,383, Dec. 21, 1990, abandoned, and Ser. No. 731,226, Jul. 16, 1991, abandoned.

[51] Int. Cl.$^6$ .................... A01H 5/00; C12N 15/82; C12N 15/84; C12N 15/31; C12P 19/04
[52] U.S. Cl. .................... 800/205; 800/DIG. 42; 800/DIG. 52; 800/DIG. 55; 800/DIG. 56; 800/DIG. 57; 435/69.1; 435/69.8; 435/97; 435/101; 435/172.3; 435/412; 435/417; 435/419; 536/23.2; 536/23.6; 536/23.7; 536/24.1
[58] Field of Search .................... 536/23.2, 23.6, 536/24.1, 23.7; 435/69.1, 69.8, 172.3, 240.4, 97, 99, 101, 201–204, 419, 412, 417; 800/205, DIG. 42, 52, 55, 56, 57

[56] References Cited

U.S. PATENT DOCUMENTS 4,956,282  9/1990  Goodman et al. .................... 435/69.51
5,349,123  9/1994  Shewmaker et al. .................... 800/205

FOREIGN PATENT DOCUMENTS 8908145  9/1989  WIPO .
9119808  12/1991  WIPO .

OTHER PUBLICATIONS

Binder et al. 1986. Gene 47:269–277.
Takano et al. 1986. J. Bacteriol. 166(3): 1118–1122.
Visser et al. 1989. Plant Science 64:185–192.
Sengupta-Gopalan et al. 1985. Proc. Natl. Acad. Sci. USA 82:3320–3324.
Anderson et al. 1990. pp. 159–180 In Mol. Cell. Biol. Potato, Vayda et al., eds.
Twell et al. 1987. Plant Mol. Biol. 9:365–375.
Schreier et al. 1985. EMBO J 4(2):25–32.
Olive et al. 1989. Plant Mol. Biol. 12(5):525–538.
Baulcombe, D. 1983. pp. 93–108 In: Genetic Engineering, vol. 5, Setlow et al., eds., Plenum Press: New York.
Khursheed et al. 1988. J. Biol. Chem. 263(35):18953–18960.

*Primary Examiner*—David T. Fox
*Attorney, Agent, or Firm*—Bell Seltzer Intellectual Property Group

[57] ABSTRACT

The present invention is directed to the modification of reserve polysaccharides in plants. Specifically, it has been found that host plants can be successfully transformed with a nucleic acid sequence capable of expressing a chimeric reserve polysaccharide modification enzyme gene sequence which will synthesize novel reserve polysaccharides in plants or convert the transformed plant's endogenous starch reserves to novel starch degradation products.

42 Claims, 33 Drawing Sheets

GLGA-40

| | | | | | |
|---|---|---|---|---|---|
| GATCTAACAG | GAGGGATAAT | GCAGGTTTTA | CATGTATGTT | CAGAGATGTT | CCCGCTGCTT | 60
| AAAACCGGCG | GTCTGGCTGA | TGTTATTGGG | GCATTACCCG | CAGCACAAAT | CGCAGACGGC | 120
| GTTGACGCTC | GCGTACTGTT | GCCTGCATTT | CCCGATATTC | GCCGTGGGCGT | GACCGATGCG | 180
| CAGGTAGTAT | CCCGTCGTGA | TACCTTCGCC | GGACATATCA | CGCTGTTGTT | CGGTCATTAC | 240
| AACGGGGTTG | GCATTTACCT | GATTGACGCG | CCGCATCTCT | ATGATCGTCC | GGGAAGCCCG | 300
| TATCACGATA | CCAACTTATT | TGCCTATACC | GACAACGTAT | TGCGTTTTGC | GCTGCTGGGG | 360
| TGGGTTGGGG | CAGAAATGGC | CAGCGGGGCTT | GACCCATTCT | GGCGTCCTGA | TGTGGTGCAT | 420
| GCGCACGACT | GGCATGCAGG | CCTTGCGCCT | GCGTATCTGG | CGGGGCGCGG | GCGTCCGGCG | 480
| AAGTCGGTGT | TTACTGGGCA | CAACCTGGCC | TATCAAGGCA | TGTTTTATGC | ACATCACATG | 540

FIG. 1A

| | | | | |
|---|---|---|---|---|
| AATGACATCC | AATTGCCATG | GTCATTCTTT | AATATTCATG | GGCTGGAATT CAACGGACAA 600 |
| ATCTCTTTCC | TGAAGGCCGG | TCTGTACTAT | GCCGATCACA | TTACGGCGGT CAGTCCAACC 660 |
| TACGCTCGCG | AGATCACCGA | ACCGCAGTTT | GCCTACGGTA | TGGAAGGTCT GTTGCAACAG 720 |
| CGTCACCGTG | AAGGGCGTCT | TTCCGGCGTA | CTGAACGGCG | TGGACGAGAA AATCTGGAGT 780 |
| CCAGAGACGG | ACTTACTGTT | GGCCTCGCGT | TACACCCGCG | ATACGTTGGA AGATAAAGCG 840 |
| GAAAATAAGC | GCCAGTTACA | AATCGCAATG | GGGCTTAAGG | TTGACGATAA AGTGCCGCTT 900 |
| TTTGCAGTGG | TGAGCCGTCT | GACCAGCCAG | AAAGGTCTCG | ACCTGGTGCT GGAAGCCTTA 960 |
| CCGGGTCTTC | TGGAGCAGGG | CGGGCAGCTG | GCGCTACTCG | GCGCGGGCGA TCCGGTGCTG 1020 |
| CAGGAAGGTT | TCCTTGCGGC | GGCAGCGGAA | TACCCCGGTC | AGTTGGGCGT TCAGATTGGC 1080 |

FIG. 1B

```
TATCACGAAG CATTTTCGCA TCGCATTATG GGCGGCGCGG ACGTCATTCT GGTGCCCAGC 1140
CGTTTTGAAC CGTGCGGCTT AACGCAACTT TATGGATTGA AGTACGGTAC GCTGCCGTTA 1200
GTGCGGCGCA CCGGTGGGCT TGCTGATACG GTTTCTGACT GTTCTCTTGA GAACCTTGCA 1260
GATGGCGTCG CCAGTGGGTT TGTCTTTGAA GATAGTAATG CCTGGTCGCT GTTACGGGCT 1320
ATTCGACGTG CTTTTGTACT GTGGTCCCGT CCTTCACTGT GGCGGTTTGT GCAACGTCAG 1380
GCTATGGCAA TGGATTTTAG CTGGCAGGTC GCGGCGAAGT CGTACCGTGA GCTTTACTAT 1440
CGCTCGAAAT AGTTTTCAGT CGAC 1464
```

FIG. 1C

GLGA-40

MET Gln Val Leu His Val Cys Ser Glu MET Phe Pro Leu Leu Lys Thr
1                       5                      10                      15

Gly Gly Leu Ala Asp Val Ile Gly Ala Leu Pro Ala Ala Gln Ile Ala
                20                      25                      30

Asp Gly Val Asp Ala Arg Val Leu Leu Pro Ala Phe Pro Asp Ile Arg
        35                      40                      45

Arg Gly Val Thr Asp Ala Gln Val Val Ser Arg Arg Asp Thr Phe Ala
        50                      55                      60

Gly His Ile Thr Leu Leu Phe Gly His Tyr Asn Gly Val Gly Ile Tyr
65                      70                      75              80

Leu Ile Asp Ala Pro His Leu Tyr Asp Arg Pro Gly Ser Pro Tyr His
                85                      90                      95

Asp Thr Asn Leu Phe Ala Tyr Thr Asp Asn Val Leu Arg Phe Ala Leu
                100                     105                     110

FIG. 2 A

Leu Gly Trp Val Gly Ala Glu MET Ala Ser Gly Leu Asp Pro Phe Trp
115                     120                     125

Arg Pro Asp Val Val His Ala His Asp Trp His Ala Gly Leu Ala Pro
130                     135                     140

Ala Tyr Leu Ala Ala Arg Gly Arg Pro Ala Lys Ser Val Phe Thr Gly
145                     150                     155                 160

His Asn Leu Ala Tyr Gln Gly MET Phe Tyr Ala His His MET Asn Asp
                165                     170                     175

Ile Gln Leu Pro Trp Ser Phe Phe Asn Ile His Gly Leu Glu Phe Asn
                180                     185                     190

Gly Gln Ile Ser Phe Leu Lys Ala Gly Leu Tyr Tyr Ala Asp His Ile
                195                     200                     205

Thr Ala Val Ser Pro Thr Tyr Ala Arg Glu Ile Thr Glu Pro Gln Phe
210                     215                     220

FIG. 2 B

Ala Tyr Gly MET Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
            245                 250                 255

Thr Asp Leu Leu Leu Ala Ser Arg Tyr Thr Arg Asp Thr Leu Glu Asp
                260                 265                 270

Lys Ala Glu Asn Lys Arg Gln Leu Gln Ile Ala MET Gly Leu Lys Val
                275                 280                 285

Asp Asp Lys Val Pro Leu Phe Ala Val Val Ser Arg Leu Thr Ser Gln
            290                 295                 300

Lys Gly Leu Asp Leu Val Leu Glu Ala Leu Pro Gly Leu Leu Glu Gln
305                 310                 315                 320

Gly Gly Gln Leu Ala Leu Leu Gly Ala Gly Asp Pro Val Leu Gln Glu
            325                 330                 335

FIG. 2 C

Gly Phe Leu Ala Ala Ala Ala Glu Tyr Pro Gly Gln Val Gly Val Gln
                340                     345                     350

Ile Gly Tyr His Glu Ala Phe Ser His Arg Ile MET Gly Gly Ala Asp
                355                     360                     365

Val Ile Leu Val Pro Ser Arg Phe Glu Pro Cys Gly Leu Thr Gln Leu
                370                     375                     380

Tyr Gly Leu Lys Tyr Gly Thr Leu Pro Leu Val Arg Arg Thr Gly Gly
                385                     390                     395                 400

Leu Ala Asp Thr Val Ser Asp Cys Ser Leu Glu Asn Leu Ala Asp Gly
                405                     410                     415

Val Ala Ser Gly Phe Val Phe Glu Asp Ser Asn Ala Trp Ser Leu Leu
                420                     425                     430

Arg Ala Ile Arg Arg Ala Phe Val Leu Trp Ser Arg Pro Ser Leu Trp
                435                     440                     445

FIG. 2 D

Arg Phe Val Gln Arg Gln Ala MET Ala MET Asp Phe Ser Trp Gln Val
450 455 460

Ala Ala Lys Ser Tyr Arg Glu Leu Tyr Tyr Arg Ser Lys
465 470 475

FIG. 2 E

```
GATCTAGGAG CGATA ATG GTT AGT TTA GAG AAG AAC GAT CAC TTA ATG          48
               MET Val Ser Leu Glu Lys Asn Asp His Leu MET
                1                   5                   10

TTG GCG CGC CAG CTG CCA TTG AAA TCT GTT GCC CTG ATA CTG GCG GGA       96
Leu Ala Arg Gln Leu Pro Leu Lys Ser Val Ala Leu Ile Leu Ala Gly
            15                  20                  25

GGA CGT GGT ACC CGC CTG AAG GAT TTA ACC AAT AAG CGA GCA AAA CCG      144
Gly Arg Gly Thr Arg Leu Lys Asp Leu Thr Asn Lys Arg Ala Lys Pro
                30                  35                  40

GCC GTA CAC TTC GGC GGT AAG TTC CGC ATT ATC GAC TTT GCG CTG TCT      192
Ala Val His Phe Gly Gly Lys Phe Arg Ile Ile Asp Phe Ala Leu Ser
            45                  50                  55

AAC TGC ATC AAC TCC GGG ATC CGT CGT ATG GGC GTG ATC ACC CAG TAC      240
Asn Cys Ile Asn Ser Gly Ile Arg Arg MET Gly Val Ile Thr Gln Tyr
60                  65                  70                  75

CAG TCC CAC ACT CTG GTG CAG CAC ATT CAG CGC GGC TGG TCA TTC TTC      288
Gln Ser His Thr Leu Val Gln His Ile Gln Arg Gly Trp Ser Phe Phe
            80                  85                  90
```

FIG. 3A

```
AAT GAA ATG AAC GAG TTT GTC GAT CTG CTG CCA GCA CAG CAG AGA           336
Asn Glu MET Asn Glu Phe Val Asp Leu Leu Pro Ala Gln Gln Arg
     95                 100                 105

ATG AAA GGG GAA AAC TGG TAT CGC GGC ACC GCA GAT GCG ACC CAA           384
MET Lys Gly Glu Asn Trp Tyr Arg Gly Thr Ala Asp Ala Thr Gln
        110                 115                 120

AAC CTC GAC ATT ATC CGC CGT TAT AAA GCG GAA TAC GTG GTG ATC CTG       432
Asn Leu Asp Ile Ile Arg Arg Tyr Lys Ala Glu Tyr Val Val Ile Leu
    125                 130                 135

GCG GGC GAC CAT ATC TAC AAG CAA GAC TAC TCG CGT ATG CTT ATC GAT       480
Ala Gly Asp His Ile Tyr Lys Gln Asp Tyr Ser Arg MET Leu Ile Asp
140                 145                 150                 155

CAC GTC GAA AAA GGC GCA CGT TGC ACC GTT GCT TGT ATG CCA GTA CCG       528
His Val Glu Lys Gly Ala Arg Cys Thr Val Ala Cys MET Pro Val Pro
            160                 165                 170

ATT GAA GAA GCC TCC GCA TTT GGC GTT ATG GCG GTT GAT GAG AAC GAT       576
Ile Glu Glu Ala Ser Ala Phe Gly Val MET Ala Val Asp Glu Asn Asp
                175                 180                 185
```

FIG. 3B

```
AAA ATT ATC GAA TTC GTT GAA AAA CCT GCT AAC CCG CCG TCA ATG CCG      624
Lys Ile Ile Glu Phe Val Glu Lys Pro Ala Asn Pro Pro Ser MET Pro
    190                 195                 200

AAC GAT CCG AGC AAA TCT CTG GCG AGT ATG GGT ATC TAC GTC TTT GAC      672
Asn Asp Pro Ser Lys Ser Leu Ala Ser MET Gly Ile Tyr Val Phe Asp
    205                 210                 215

GCC GAC TAT CTG TAT GAA CTG CTG GAA GAC GAT CGC GAT GAG AAC          720
Ala Asp Tyr Leu Tyr Glu Leu Leu Glu Asp Asp Arg Asp Glu Asn
    220                 225                 230                 235

TCC AGC CAC GAC TTT GGC AAA GAT TTG ATT CCC AAG ATC ACC GAA GCC      768
Ser Ser His Asp Phe Gly Lys Asp Leu Ile Pro Lys Ile Thr Glu Ala
    240                 245                 250

GGT CTG GCC TAT GCG CAC CCG TTC CCG CTC TCT TGC GTA CAA TCC GAC      816
Gly Leu Ala Tyr Ala His Pro Phe Pro Leu Ser Cys Val Gln Ser Asp
    255                 260                 265
```

FIG. 3C

```
CCG GAT GCC GAG CCG TAC TGG CGC GAT GTG GGT ACG CTG GAA GCT TAC          864
Pro Asp Ala Glu Pro Tyr Trp Arg Asp Val Gly Thr Leu Glu Ala Tyr
270                 275                 280

TGG AAA GCG AAC CTC GAT CTG GCC TCT GTG GTG CCG GAA CTG GAT ATG          912
Trp Lys Ala Asn Leu Asp Leu Ala Ser Val Val Pro Glu Leu Asp MET
        285                 290                 295

TAC GAT CGC AAT TGG CCA ATT CGC ACC TAC AAT GAA TCA TTA CCG CCA          960
Tyr Asp Arg Asn Trp Pro Ile Arg Thr Tyr Asn Glu Ser Leu Pro Pro
300                 305                 310                 315

GCG AAA TTC GTG CAG GAT CGC TCC GGT AGC CAC GGG ATG ACC CTT AAC         1008
Ala Lys Phe Val Gln Asp Arg Ser Gly Ser His Gly MET Thr Leu Asn
        320                 325                 330

TCA CTG GTT TCC GAC GGT TGT GTG ATC TCC GGT TCG GTG GTG CAG             1056
Ser Leu Val Ser Asp Gly Cys Val Ile Ser Gly Ser Val Val Gln
335                 340                 345

TCC GTT CTG TTC TCG CGC GTT CGC GTG AAT TCA TTC TGC GAC ATT GAT         1104
Ser Val Leu Phe Ser Arg Val Arg Val Asn Ser Phe Cys Asp Ile Asp
350                 355                 360
```

FIG. 3D

```
TCC GCC GTA TTG TTA CCG GAA GTA TGG GTA GGT CGC TCG TGC CGT CTG    1152
Ser Ala Val Leu Leu Pro Glu Val Trp Val Gly Arg Ser Cys Arg Leu
365                     370                 375

CGC CGC TGC GTC ATC GAT CGT GCT TGT GTT ATT CCG GAA GGC ATG GTG    1200
Arg Arg Cys Val Ile Asp Arg Ala Cys Val Ile Pro Glu Gly MET Val
380                     385                 390                 395

ATT GGT GAA AAC GCA GAG GAA GAT GCA CGT CGT TTC TAT CGT TCA GAA    1248
Ile Gly Glu Asn Ala Glu Glu Asp Ala Arg Arg Phe Tyr Arg Ser Glu
        400                 405                 410

GAA GGC ATC GTG CTG GTA ACG CGC GAA ATG CTA CGG AAG TTA GGG CAT    1296
Glu Gly Ile Val Leu Val Thr Arg Glu MET Leu Arg Lys Leu Gly His
    415                 420                 425

AAA CAG GAG CGA TAATGCAGGG TCGAC                                   1323
Lys Gln Glu Arg
430
```

FIG. 3E

```
     XbaI HindIII  EcoRV
       |    |       |
  1  TCTAGAAGCTTGGATATCTGGCAGCAGAAAAACAAGTAGTTGAGAACTAAG  51
     SerArgSerLeuAspIleTrpGlnGlnLysAsnLys . LeuArgThrLys
                                          LeuGluAlaTrpLeuAlaSerGlySerArgLysThrSerSer . GluLeuAr
      . LysLeuGlyTyrLeuAlaAlaGluLysGlnValValGluAsn . G
         2      7                                  16

PvuII
                                   NspBII
                                     |
  52 AAGAAGAAAATGGCTTCCTCAATGATCTCCTCCCCAGCTGTTACCACCGTC  102
     LysLysLysMETAlaSerSerMETIleSerSerProAlaValThrThrVal
     gArgArgLysTrpLeuProGln . SerProGlnLeuLeuProProSe
     luGluGluAsnGlyPheLeuAsnAspLeuLeuProSerCysTyrHisArgG
                                                89
                                                89

StyI
                                                 NcoI
          NaeI                                   DsaI
           |                                      |
     HindII HgiCI
       |    |
 103 AACCGTGCCGGTGCCGGCATGGTTGCTCCATTCACCGGCCTCAAATCCATG  153
     AsnArgAlaGlyAlaGlyMETValAlaProPheThrGlyLeuLysSerMET
     rThrValProValProAlaTrpLeuLeuHisSerProAlaSerAsnProTr
     lnProCysArgCysArgHisGlyCysSerIleHisArgProGlnIleHisG
     103    113                                  150
               118                               150
                                                 150
```

```
                                    BbvII              NheI
154 GCTGGGCTTCCCCACGAGGAAGACCAACAATGACATTACCTCCATTGCTAGC 204
    AlaGlyPheProThrArgLysThrAsnAsnAspIleThrSerIleAlaSer
    pLeuAlaSerProArgGlyArgProThrMETThrLeuProProLeuLeuAl
    lyTrpLeuProHisGluGluAspGlnGln . HisTyrLeuHisCys . G
                              179                    200

SphI
              BspMI   NspI          [MfeI]
              [AvaIII]        HaeI
205 AACGGTGGAAGAGTACAATGCATGCAGGTGTGGCCTCCAATTGGAAAGAAG 255
    AsnGlyGlyArgValGlnTyrAsnAlaCysArgCysGlyLeuGlnLeuGluArgAr
    aThrValGluGluTyrAsnAlaCysArgCysGlyLeuGlnLeuGluArgAr
    lnArgTrpLysSerThrMETHisAlaGlyValAlaSerAsnTrpLysGluG
    Ksp632I                             238        242
      208           220       229
                              229

XhoII
                        BamHI
256 AAGTTTGAGACTCTTTCCTGGGATCC 281
    LysPheGluThrLeuSerTrpAsp
    gSerLeuArgLeuPheProGlyIle
    luVal . AspSerPheLeuGlySer
                            277
                            277
```

```
X         10        20        30        40        50        60        70
 CTCGAGATTTGTCAAATCAGGCTCAAAGATCGTTTTTCATATCGGAATGAGGATTTTATTTATTCTTTTA
 ::::::::::::::::::::::::::::::::::::::::::::::::::::::::::::::::::::::
     ATTTGTCAAATCAGGCTCAAAGATCGTTTTTCATATCGGAATGAGGATTTTATTTATTCTTTTA
 X         10        20        30        40        50        60

80        90       100       110       120       130       140
 AAAATAAAGAGGTGTTGAGCTAAACAATTTCAAATCTCATCACACATATGGGGTCAGCCACAAAAATAAA
 ::::::::::::::::::::::::::::::::::::::::::::::::::::::::::::::::::::::
 AAAATAAAGAGGTGTTGAGCTAAACAATTTCAAATCTCATCACACATATGGGGTCAGCCACAAAAATAAA
        70        80        90       100       110       120       130

150       160       170       180       190       200       210
 GAACGGTTGGAACGGATCTATTATATAATACTAATAAAGAATAGAAAAAGGAAAGTGAGTGAGGTGCGAG
 ::::::::::::::::::::::::::::::::::::::::::::::::::::::::::::::::::::::
 GAACGGTTGGAACGGATCTATTATATAATACTAATAAAGAATAGAAAAAGGAAAGTGAGTGAGGTGCGAG
       140       150       160       170       180       190       200

220       230       240       250       260       270       280
 GGAGAGAATCTGTTTACTATCAGAGTCGATCATGTGTCAGTTTTATCGATATGACTCTGACTTCAACTGA
 ::::::::::::::::::::::::::::::::::::::::::::::::::::::::::::::::::::::
 GGAGAGAATCTGTTTACTATCAGAGTCGATCATGTGTCAGTTTTATCGATATGACTCTGATTTCAACTGA
       210       220       230       240       250       260       270

290       300       310       320       330       340
 GTTTAAGCAATTCTGATAAGGCGAGGAAAATCACAGTGCTGAA-TCTAGAAAAATCTCATAGTGTGAGAT
 ::::::::::::::::::::::::::::::::::::::::::::::::::::::::::::::::::::::
 GTTTAAGCAATTCTGATAAGGCGAGGAAAATCACAGTGCTGAAATCTAGAAAATCTCATAGTGTGAGAT
       280       290       300       310       320       330       340
```

FIG. 5A

```
                    360       370       380       390       400       410
         AAGTCTCAACAACAAAACGTTGAGTCCATAGAGGGGTGTATGTGACACCCCAACCTCAGCAAAAGAAAACC
         :::::::::::::::::::::::::::::::::::::::::::::::::::::::::::::::::::::
         AAGTCTCAACAACAAAACGTTGAGTCCATAGAGGGGTGTATGTGACACCCCAACCTCAGCAAAAGAAAACC
                    350       360       370       380       390       400       410

430       440       450       460       470       480
         TCCCCTCAAGAAGGACATTTGCGGTGCTAAACAATTTCAAGTCTCATCACACATATATATTATATAATAC
         :::::::::::::::::::::::::::::::::::::::::::::::::::::::::::::::::::::
         TCCCCTCAAGAAGGACATTTGCGGTGCTAAACAATTTCAAGTCTCATCACACATATATATTATATAATAC
                    420       430       440       450       460       470       480

500       510       520       530       540       550
         TAATAAAGAATAGAAAAAGGAAAAGGTAAACATCACTAATGACAGTTGCGGTGCAAAGTGAGTGAGATAAT
         :::::::::::::::::::::::::::::::::::::::::::::::::::::::::::::::::::::
         TAATAAAGAATAGAAAAAGGAAAAGGTAAACATCACTAATGACAGTTGCGGTGCAAAGTGAGTGAGATAAT
                    490       500       510       520       530       540       550

570       580       590       600       610       620
         AAACATCAGTAATAGACATCACTAACTTTTATTGGTTATGTCAAACTCAAAATAAAATTTCTCAACTTGT
         :::::::::::::::::::::::::::::::::::::::::::::::::::::::::::::::::::::
         AAACATCAGTAATAGACATCACTAACTTTTTATTGGTTATGTCAAACTCAAAATAAAATTTCTCAACTTGT
                    560       570       580       590       600       610       620
```

FIG. 5B

```
         640       650       660       670       680       690
TTACGTGCCTATATATACCATGCTTGTTATATGCTCAAAGCACCAACAAAATTTAAAAACAATTTGAACA
::::::::::::::::::::::::::::::::::::::::::::::::::::::::::::::::::::
TTACGTGCCTATATATACCATGCTTGTTATATGCTCAAAGCACCAACAAAATTTAAAAACAATTTGAACA
        630       640       650       660       670       680       690

710
TTTGCAAAACTAGTATGGG
::::::::
TTTGCAAAA
     700 X
```

FIG. 5C

```
X          10         20         30         40         50         60         70
  CTCGAGATTTGTCAAATCAGGCTCAAAGATCGTTTTCATATCGGAATGAGGATTTTATTTATTCTTTTA
  :::::::::::::::::::::::::::::::::::::::::::::::::::::::::::::::::
  ATTTGTCAAATCAGGCTCAAAGATCGTTTTCATATCGGAATGAGGATTTTATTTATTCTTTTA
X            10         20         30         40         50         60

80         90        100        110        120        130        140
  AAAATAAAGAGGTGGTGAGCTAAACAATTTCAAATCTCATCACACATATGGGGTCAGCCACAAAAATAAA
  :::::::::::::::::::::::::::::::::::::::::::::::::::::::::::::::::::
  AAAATAAAGAGGTGTTGAGCTAAACAATTTCAAATCTCATCACACATATGGGGTCAGCCACAAAAATAAA
            70         80         90        100        110        120        130

150        160        170        180        190        200        210
  GAACGGTTGGAACGGATCTATTATATAATACTAATAAAGAATAGGAAAAGGAAAGTGAGTGAGGTGCGAG
  :::::::::::::::::::::::::::::::::::::::::::::: :::::::::::::::::::::
  GAACGGTTGGAACGGATCTATTATATAATACTAATAATAAAGAATAGAAAAAGGAAAGTGAGTGAGGTGCGAG
           140        150        160        170        180        190        200

220        230        240        250        260        270        280
  GGAGAGAATTTGTTTAATATCAGAGTCGATCATGTGTCAGTTTTATCGATATGATTCTGACTTCAACTGA
  :::::::::::::::::::::::::::::::::::::::::::::::::: :::::::::::::::::
  GGAGAGAATCTGTTTACTATCAGAGTCGATCATGTGTCAGTTTTATCGATATGACTCTGATTTCAACTGA
           210        220        230        240        250        260        270
```

FIG. 6A

```
      290        300        310        320        330        340
GTTTAAGCAATTCTGATAAGGCGGAGAAAAATCATAGTGCTGAG-TCTAGAAAAATCTTCATGCAGTGTGAG
 :::::::::::::::::::::::::::::: :::::::::: : :::::::::::::: ::::::::::
GTTTAAGCAATTCTGATAAGGCGGAGAAAAATCACCAGTGCTGAAATCTAGAAAAATCTCAT--AGTGTGAG
      280        290        300        310        320        330        340

360
ATAAACCTCAACAAGAAC-------------------------
 ::::: ::::::::::: :::
ATAAGTCTCAACAAAAACGTTGAGTCCATAGAGGGGGTGTATGTGACACCCCAACCTCAGCAAAAGAAAA
      350        360        370        380        390        400        410

ATTTGCGGTGCTAAACAATTTCAAGTCTTATCACACATATATTATATATT
                                   :::::::::::::::::::::::::::::::::::::::::::::::: :
CCTCCCCCTCAAGAAGGACATTTGCGGTGCTAAACAATTTCAAGTCTCATCACACATATATTATATAAT
      420        430        440        450        460        470        480

:::::::::::::::::::::::::::::::::::::::::::::::::::
ACTAATAAAGAATAGAAAAAGGAAAAGGTAAACATCACTAATGACAGTTGCGGTGCAAAGTGAGTGAGATA
      490        500        510        520        530        540        550
```

FIG. 6B

```
       500        510        520        530        540        550
ATAAACATCACTAATAGACATCACTAACTTTTATTGGTTATGTCAAACTCAAAAATAAAATTTCTCAACTT
:: :::::::: :: ::::::::::::::::::::::::::::::::::::::::::::::::::::::::
ATAAACATCAGTAATAGACATCACTAACTTTTATTGGTTATGTCAAACTCAAAAATAAAATTTCTCAACTT
       560        570        580        590        600        610        620

570        580        590        600        610        620
GTTTACGTGCCTATATATACCATGCTTGTTATATGCTCAAAGCACCAACAAAATTTAAAAACAATTTGAA
::::::::::::::::::::::::::::::::::::::::::::::::::::::::::::::::::::::
GTTTACGTGCCTATATATACCATGCTTGTTATATGCTCAAAGCACCAACAAAATTTAAAAACAATTTGAA
       630        640        650        660        670        680        690

640        650
CATTTGCAAAACTAGTATGGG
:: :::::::
CATTTGCAAAA
       700  X
```

FIG. 6C

```
X
         10        20        30        40        50        60
    GGATCCATTAGGACTAGATAATGAAAAGAAACCGTTTTTTTAATACCTCGGCTGCTATTG
    ||||||||||||||||||||||||||||||||||||||||||||||||||||||||||||
    ATTAGGACTAGATAATGAAAAGAAACCGTTTTTTTAATACCTCGGCTGCTATTG
X            10        20        30        40        50

70        80        90       100       110       120
    CCATTTCGATTGCATTAAATACTTTTTTTGTAGCATGCAGACGATTGCTGCTGAACCAG
    ||||||||||||||||||||||||||||||||||||||||||||||||||||||||||||
    CCATTTCGATTGCATTAAATACTTTTTTTGTAGCATGCAGACGATTGCTGCTGAACCAG
             60        70        80        90       100       110

130       140       150       160       170       180
    AAGAAACTTATCTTGATTTTCGTAAGGAGACGATATATTTCTATTCCTTGATCGTTTCA
    ||||||||||||||||||||||||||||||||||||||||||||||||||||||||||||
    AAGAAACTTATCTTGATTTTCGTAAGGAGACGATATATTTCTATTCCTTGATCGTTTCA
        120       130       140       150       160       170

190       200       210       220       230       240
    GCGATGGAGAGATCCAAGTAATAATGCAGGTTTAATTCTGCAACCTACGATCCTAATAATT
    ||||||||||||||||||||||||||||||||||||||||||||||||||||||||||||
    GCGATGGAGAGATCCAAGTAATAATGCAGGTTTAATTCTGCAACCTACGATCCTAATAATT
        180       190       200       210       220       230
```

FIG. 7A

```
                   250        260        270        280        290        300
TAAAAAATATACTGGAGGAGATCTCCGGGGGTTGATTAATAAACTACCCTATTTAAAAT
||||||||||||||||||||||||||||||||||||||||||||||||||||||||||
TAAAAAATATACTGGAGGAGATCTCCGGGGGTTGATTAATAAACTACCCTATTTAAAAT
                   240        250        260        270        280        290

310        320        330        340        350        360
CACTTGGTGTTACTTCAATCTGGATTACTCCCCCCAATCGATAATGTGAATAATACTGATG
||||||||||||||||||||||||||||||||||||||||||||||||||||||||||
CACTTGGTGTTACTTCAATCTGGATTACTCCCCCCAATCGATAATGTGAATAATACTGATG
                   300        310        320        330        340        350

370        380        390        400        410        420
CTGCTGGCAATACTGGATATCATGGTTATTGGGGAAGAGATTATTTTCGTATAGATGAAC
||||||||||||||||||||||||||||||||||||||||||||||||||||||||||
CTGCTGGCAATACTGGATATCATGGTTATTGGGGAAGAGATTATTTTCGTATAGATGAAC
                   360        370        380        390        400        410

430        440        450        460        470        480
ATTTTGGCAATCTCGATGATTTCAAAGAACTGACTAGTTTGATGCATAGTCCTGATTATA
||||||||||||||||||||||||||||||||||||||||||||||||||||||||||
ATTTTGGCAATCTCGATGATTTCAAAGAACTGACTAGTTTGATGCATAGTCCTGATTATA
                   420        430        440        450        460        470

FIG. 7B
```

```
              490       500       510       520       530       540
     ATATGAAACTGGTTCTTGATTATGCCCCTAATCATTCGAATGCTAATGATGAAAATGAAT
     ||||||||||||||||||||||||||||||||||||||||||||||||||||||||||||
     ATATGAAACTGGTTCTTGATTATGCCCCTAATCATTCGAATGCTAATGATGAAAATGAAT
              480       490       500       510       520       530

550       560       570       580       590       600
     TTGGTGCACTATATCGTGATGGTGTGTTATTACTGATTATCCTACAGATGTTGCCGCCA
     ||||||||||||||||||||||||||||||||||||||||| ||||||||||||||||||
     TTGGTGCACTATATCGTGATGGTGTGTTTATTACTGATTATCCTACGAATGTTGCCGCCA
              540       550       560       570       580       590

610       620       630       640       650       660
     ATACGGGCTGGTATCATCACAATGGTGGGTAACGAACTGGAATGATTTCTTCCAAGTGA
     ||||||||||||||||||||||||||||||||||||||||||||||||||||||||||||
     ATACGGGCTGGTATCATCACAATGGTGGGTAACGAACTGGAATGATTTCTTCCAAGTGA
              600       610       620       630       640       650

670       680       690       700       710       720
     AGAATCATAATCTATTCAATCTATCAGACCTCAATCAATCCAATACTGATGTCTACCAGT
     ||||||||||||||||||||||||||||||||||||||||||||||||||||||||||||
     AGAATCATAATCTATTCAATCTATCAGACCTCAATCAATCCAATACTGATGTCTACCAGT
              660       670       680       690       700       710
```

FIG. 7C

```
          730       740       750       760       770       780
ACTTGTTGGATGGCTCTAAATTTTGGATCGATGCTGGTGTGGATGCTATCAGGATTGATG
||||||||||||||||||||||||||||||||||||||||||||||||||||||||||||
ACTTGTTGGATGGTTCTAAATTTTGGATCGATGCTGGTGTGGATGCTATCAGGATTGATG
          720       730       740       750       760       770

790       800       810       820       830       840
CCATCAAGCATATGGACAAGTCTTTTATACAGAAATGGACCAGCGATATTTATGATTACA
||||||||||||||||||||||||||||||||||||||||||||||||||||||||||||
CCATCAAGCATATGGACAAGTCTTTTATACAGAAATGGACCAGCGATATTTATGATTACA
          780       790       800       810       820       830

850       860       870       880       890       900
GTAAGTCTATCGGCCGGGAAGGATTTTTTTCTTCGGTGAATGGTTTGGTGCCAGTGCGA
|||||||||||||||||||||||||||||||||||||||||||||||||||||||||||
GTAAGTCTATCGGCCGGGAAGGATTTTTTTCTTCGGTGAATGGTTTGGTGCCAGTGCGA
          840       850       860       870       880       890

910       920       930       940       950       960
ATACTACAACAGGTGTTGATGGTAATGCTATCGATTACGCCAACACTTCCGGGTCAGCGT
||||||||||||||||||||||||||||||||||||||||||||||||||||||||||||
ATACTACAACAGGTGTTGATGGTAATGCTATCGATTACGCCAACACTTCCGGGTCAGCGT
          900       910       920       930       940       950
```

FIG. 7D

```
        970       980       990      1000      1010      1020
TGCTGGATTTTGGATTCCGCGATACTTTTAGAAAGAGTTTTGGTAGGACGTAGCGGAAATA
|||||||||||||||||||||||||||||||||||||||||||||||||||||||||||||
TGCTGGATTTTGGATTCCGCGATACTTTTAGAAAGAGTTTTGGTAGGACGTAGCGGAAATA
        960       970       980       990      1000      1010

1030      1040      1050      1060      1070      1080
CAATGAAAAACGTTAAATAGTTATCTGATAAAAAGACAAACAGTCTTTACCAGTGATGACT
|||||||||||||||||||||||||||||||||||||||||||||||||||||||||||||
CAATGAAAAACGTTAAATAGTTATCTGATAAAAAGACAAACAGTCTTTACCAGTGATGACT
       1020      1030      1040      1050      1060      1070

1090      1100      1110      1120      1130      1140
GGCAGGTTGTTTTTATGGATAACCATGATATGGCACGCATTGGTACCGCTCTGCGTTCAA
|||||||||||||||||||||||||||||||||||||||||||||||||||||||||||||
GGCAGGTTGTTTTTATGGATAACCATGATATGGCACGCATTGGTACCGCTCTGCGTTCAA
       1080      1090      1100      1110      1120      1130

1150      1160      1170      1180      1190      1200
ACGCCACTACTTTTGGTCCTGGAAATAATGAAAACCGGTGGAAGTCAGAGTGAAGCTTTTG
|||||||||||||||||||||||||||||||||||||||||||||||||||||||||||||
ACGCCACTACTTTTGGTCCTGGAAATAATGAAAACCGGTGGAAGTCAGAGTGAAGCTTTTG
       1140      1150      1160      1170      1180      1190
```

FIG. 7E

```
              1210       1220       1230       1240       1250       1260
         CTCAGAAACGTATAGACCTCGGTTCTGGTTGCCGACAATGACTGTACGTGGTATTCCTGCCA
         ||||||||||||||||||||||||||||||||||||||||||||||||||||||||||||
         CTCAGAAACGTATAGACCTCGGTTCTGGTTGCCGACAATGACTGTACGTGGTATTCCTGCCA
              1200       1210       1220       1230       1240       1250

1270       1280       1290       1300       1310       1320
         TTTATTATGGTACTGAACATTATGCCGCTAACTTTACCTCTAACAGTTTTGGTCAAGTTG
         ||||||||||||||||||||||||||||||||||||||||||||||||||||||||||||
         TTTATTATGGTACTGAACATTATGCCGCTAACTTTACCTCTAACAGTTTTGGTCAAGTTG
              1260       1270       1280       1290       1300       1310

1330       1340       1350       1360       1370       1380
         GCAGTGATCCTTACAACCGAGAGAAAATGCCAGGATTTGATACGGAAAGTGAGGCTTTCT
         ||||||||||||||||||||||||||||||||||||||||||||||||||||||||||||
         GCAGTGATCCTTACAACCGAGAGAAAATGCCAGGATTTGATACGGAAAGTGAGGCTTTCT
              1320       1330       1340       1350       1360       1370

1390       1400       1410       1420       1430       1440
         CCATTATTAAAACACTGGGTGACCTAAGGAAAAGTAGCCCGGCAATTCAAAATGGAACTT
         ||||||||||||||||||||||||||||||||||||||||||||||||||||||||||||
         CCATTATTAAAACACTGGGTGACCTAAGGAAAAGTAGCCCGGCAATTCAAAATGGAACTT
              1380       1390       1400       1410       1420       1430
```

FIG. 7F

```
         1450      1460      1470      1480      1490      1500
ATACTGAACTATGGGTTAATGATGATATATTAGTATTTGAGCGGGCGTTCTGGGAACGATA
||||||||||||||||||||||||||||||||||||||||||||||||||||||||||||
ATACTGAACTATGGGTTAATGATGATATATTAGTATTTGAGCGGGCGTTCTGGGAACGATA
         1440      1450      1460      1470      1480      1490

1510      1520      1530      1540      1550      1560
TTGTTATTGTTGCACTTAATCGTGGTGAGGCTAACACAATTAATGTTAAAAATATAGCGG
||||||||||||||||||||||||||||||||||||||||||||||||||||||||||||
TTGTTATTGTTGCACTTAATCGTGGTGAGGCTAACACAATTAATGTTAAAAATATAGCGG
         1500      1510      1520      1530      1540      1550

1570      1580      1590      1600      1610      1620
TTCCTAATGGGGTATATCCGAGTTTGATTGGGAATAATAGTGTTTCAGTAGCAAATAAAC
||||||||||||||||||||||||||||||||||||||||||||||||||||||||||||
TTCCTAATGGGGTATATCCGAGTTTGATTGGGAATAATAGTGTTTCAGTAGCAAATAAAC
         1560      1570      1580      1590      1600      1610

1630      1640      1650      1660      1670      1680
AGGCAACACTAACACTTATGCAAAATGAAGCTGTTGTCATTCGCTCACAATCAGATGATG
 |||||||||||||||||||||||||||||||||||||||||||||||||||||||||||
GGACAACACTAACACTTATGCAAAATGAAGCTGTTGTCATTCGCTCACAATCAGATGATG
         1620      1630      1640      1650      1660      1670
```

FIG. 7G

```
      1690       1700       1710       1720       1730       1740
CGGAGAACCCTACAGTACAAAGCATAAACTTCGCATGTAATAACGGTTATACGATTTCAG
||||||||||||||||||||||||||||||||||||||||||||||||||||||||||||
CGGAGAACCCTACAGTACAAAGCATAAACTTCACATGTAATAACGGTTATACGATTTCAG
      1680       1690       1700       1710       1720       1730

1750       1760       1770       1780       1790       1800
GTCAAAGTGTTTATATTATTGGTAATATACCTCAGTTAGGTGGTTGGGACTTAACTAAAG
||||||||||||||||||||||||||||||||||||||||||||||||||||||||||||
GTCAAAGTGTTTATATTATTGGTAATATACCTCAGTTAGGTGTTGGGACTTAACTAAAG
      1740       1750       1760       1770       1780       1790

1810       1820       1830       1840       1850       1860
CGGTAAAAATATCACCGACACAATATCCACAATGGAGTGCGAGCTTAGAGCTTCCTTCTG
||||||||||||||||||||||||||||||||||||||||||||||||||||||||||||
CGGTAAAAATATCACCGACACAATATCCACAATGGAGTGCGAGCTTAGAGCTTCCTTCTG
      1800       1810       1820       1830       1840       1850

1870       1880       1890       1900       1910       1920
ACTTAAATGTTGAATGGAAGTGTGTGAAACGTAATGAAACCAATCCGACGGCTAATGTTG
||||||||||||||||||||||||||||||||||||||||||||||||||||||||||||
ACTTAAATGTTGAATGGAAGTGTGTGAAACGTAATGAAACCAATCCGACGGCTAATGTTG
      1860       1870       1880       1890       1900       1910
```

FIG. 7H

```
          1930      1940      1950      1960      1970      1980
AGTGGCAGTCTCGGTGCAAATAACCAGTTCAATAGCAATGACACACAAAACAACGAATGGCT
|||||||||||||||||||||||||||||||||||||||||||||||||||||||||||||
AGTGGCAGTCTGGTGCAAATAACCAGTTCAATAGCAATGACACACAAAACAACGAATGGCT
     1920      1930      1940      1950      1960      1970

1990       X
CGTTTTAATTAAAAGTCGAC
||||||||||||||||
CGTTTTAATTAAAAA
     1980     X
```

FIG. 71

```
X                                                              10                                              20                                              30                                              40                                              50                                              60
MKRNRFFNTSAAIAISIALNTFFCSMQTIAAEPEETYLDFRKETIYFLFLDRFSDGDPSN
===========================================================
MKRNRFFNTSAAIAISIALNTFFCSMQTIAAEPEETYLDFRKETIYFLFLDRFSDGDPSN
X                                                              10                                              20                                              30                                              40                                              50                                              60

70                                              80                                              90                                             100                                             110                                             120
NAGFNSATYDPNNLKKYTGGDLRGLINKLPYLKSLGVTSIWITPPIDNVNNTDAAGNTGY
============================================================
NAGFNSATYDPNNLKKYTGGDLRGLINKLPYLKSLGVTSIWITPPIDNVNNTDAAGNTGY
                                                               70                                              80                                              90                                             100                                             110                                             120

130                                             140                                             150                                             160                                             170                                             180
HGYWGRDYFRIDEHFGNLDDFKELTSLMHSPDYNMKLVLDYAPNHSNANDENEFGALYRD
============================================================
HGYWGRDYFRIDEHFGNLDDFKELTSLMHSPDYNMKLVLDYAPNHSNANDENEFGALYRD
                                                              130                                             140                                             150                                             160                                             170                                             180

190                                             200                                             210                                             220                                             230                                             240
GVFITDYPTDVAANTGWYHHNGGVTNWNDFFQVKNHNLFNLSDLNQSNTDVYQYLLDGSK
===   ======================================================
GVFITDYPTNVAANTGWYHHNGGVTNWNDFFQVKNHNLFNLSDLNQSNTDVYQYLLDGSK
                                                              190                                             200                                             210                                             220                                             230                                             240
```

FIG. 8A

```
          250       260       270       280       290       300
FWIDAGVDAIRIDAIKHMDKSFIQKWTSDIYDYSKSIGREGFFFFGEWFGASANTTTGVD
||||||||||||||||||||||||||||||||||||||||||||||||||||||||||||
FWIDAGVDAIRIDAIKHMDKSFIQKWTSDIYDYSKSIGREGFFFFGEWFGASANTTTGVD
          250       260       270       280       290       300

310       320       330       340       350       360
GNAIDYANTSGSALLDFGFRDTLERVLVGRSGNTMKTLNSYLIKRQTVFTSDDWQVVFMD
||||||||||||||||||||||||||||||||||||||||||||||||||||||||||||
GNAIDYANTSGSALLDFGFRDTLERVLVGRSGNTMKTLNSYLIKRQTVFTSDDWQVVFMD
          310       320       330       340       350       360

370       380       390       400       410       420
NHDMARIGTALRSNATTFGPGNNETGGSQSEAFAQKRIDLGLVATMTVRGIPAIYYGTEH
||||||||||||||||||||||||||||||||||||||||||||||||||||||||||||
NHDMARIGTALRSNATTFGPGNNETGGSQSEAFAQKRIDLGLVATMTVRGIPAIYYGTEH
          370       380       390       400       410       420

430       440       450       460       470       480
YAANFTSNSFGQVGSDPYNREKMPGFDTESEAFSIIKTLGDLRKSSPAIQNGTYTELWVN
||||||||||||||||||||||||||||||||||||||||||||||||||||||||||||
YAANFTSNSFGQVGSDPYNREKMPGFDTESEAFSIIKTLGDLRKSSPAIQNGTYTELWVN
          430       440       450       460       470       480
```

FIG. 8B

```
       490        500        510        520        530       540
DDILVFERRSGNDIVIVALNRGEANTINVKNIAVPNGVYPSLIGNNSVSVANKQATLTLM
||||||||||||||||||||||||||||||||||||||||||||||||||   |||||
DDILVFERRSGNDIVIVALNRGEANTINVKNIAVPNGVYPSLIGNNSVSVANKRTTLTLM
       490        500        510        520        530       540

550        560        570        580        590       600
QNEAVVIRSQSDDAENPTVQSINFACNNGYTISGQSVYIIGNIPQLGGWDLTKAVKISPT
|||||||||||||||||||||||| |||||||||||||||||||||||||||||||||
QNEAVVIRSQSDDAENPTVQSINFTCNNGYTISGQSVYIIGNIPQLGGWDLTKAVKISPT
       550        560        570        580        590       600

610        620        630        640        650     X
QYPQWSASLELPSDLNVEWKCVKRNETNPTANVEWQSGANNQFNSNDTQTTNGSF.
||||||||||||||||||||||||||||||||||||||||||||||||||||||
QYPQWSASLELPSDLNVEWKCVKRNETNPTANVEWQSGANNQFNSNDTQTTNGSF.
       610        620        630        640        650     X
```

FIG. 8C

GLYCOGEN BIOSYNTHETIC ENZYMES IN PLANTS

RELATED APPLICATION DATA

The present application is a continuation application of U.S. patent application Ser. No. 08/016,881, filed on Feb. 11, 1993, which is a continuation-in-part of U.S. patent application Ser. No. 07/735,065, filed on Jul. 24, 1991, now U.S. Pat. No. 5,349,123, which in turn is a continuation-in-part of abandoned U.S. patent application Ser. Nos. 07/632,383 filed on Dec. 21, 1990 and 07/731,226 filed on Jul. 16, 1991; and a CIP of 07/536,392 filed on Jun. 11, 1990, now abandoned.

TECHNICAL FIELD

This invention relates to transgenic plants and, more particularly, to methods and compositions which modify the biosynthesis and degradation pathways of reserve polysaccharides in plants.

BACKGROUND OF THE INVENTION

In the animal kingdom, nonvascular plants, fungi, yeast and bacteria, the primary reserve polysaccharide is glycogen. Glycogen is a D-glucose polysaccharide containing linear molecules with α-1,4 glycosyl linkages and is branched via α-1,6 glycosyl linkages. Although glycogen is analogous to starch from a linkage comparison, glycogen exhibits a different chain length and degree of polymerization. In bacteria, for example, the α-1,6 glycosyl linkages constitute only approximately 10% of the total linkages, indicating that the majority of the glycogen polymer resides as linear glucose units.

In vascular plants, reserve polysaccharides are stored in roots, tubers and seeds in the form of starch. Starch, a complex polymer of D-glucose, consists of a mixture of linear chain (amylose) and branched chain (amylopectin) glucans. Starches isolated from different plants are found to have distinct proportions of amylose. Typically, amylose comprises from about 10–25% of plant starch, the remainder being the branched polymer amylopectin. Amylopectin contains low molecular weight chains and high molecular weight chains, with the low molecular weight chains ranging from 5–30 glucose units and the high molecular weight chains from 30–100 or more. The ratio of amylose/amylopectin and the distribution of low molecular weight to high molecular weight chains in the amylopectin fraction are known to affect the properties, such as thermal stabilization, retrogradation, and viscosity, and therefore the utility of starch. The highest published low m.w./high m.w. chain ratios (on a weight basis) in amylopectin are 3.9/1 for waxy corn starch, which has unique properties. Additionally, duwx, which has slightly more branch points than waxy, also has further unique properties.

In addition, starches from different plants or plant parts often have different properties. For example, potato starch has different properties than other starches, some of which may be due to the presence of phosphate groups. In some plant species, mutants have been identified which have altered contents of amylose and amylopectin. Mutations that affect the activity of starch-branching enzyme in peas, for example, result in seeds having less starch and a lower proportion of amylopectin. Also, mutations in the waxy locus of maize, which encodes a starch granule bound starch synthase, result in plants which produce amylopectin exclusively. Similarly, a potato mutant has been identified whose starch is amylose-free (Hovenkamp-Hermelink et al. *Theor. Appl. Genet.* (1987) 75:217–221). It has been found that varying the degree of starch branching can confer desirable physical properties; other changes in the characteristics of native starch could result in the production of polymers with new applications.

Cyclodextrins are the products of enzymatic starch degradation by a class of amylases termed cyclodextrin glycosyltransferase (CGT) enzymes. The family of cyclodextrins contains three major and several minor cyclic oligosaccharides which are composed of a number of homogenous cyclic α-1,4-linked glucopyranose units. The cyclodextrin having six glucopyranose units is termed α-cyclodextrin (also know as Schardinger's α-dextrin, cyclomaltohexaose, cyclohexaglucan, cyclohexaamylose, α-CD, ACD and C6A). The seven unit cyclodextrin is termed β-cyclodextrin (also known as Schardinger's β-dextrin, cyclomaltoheptaose, cycloheptaglucan, β-CD, BCD and C7A). The eight unit cyclodextrin is termed γ-cyclodextrin (also known as Schardinger's γ-dextrin, cyclomaltooctaose, cyclooctaglucan, cyclooctaamylose, γ-CD, GCD and C8A).

The cyclic nature of cyclodextrins allows them to function as clathrates (inclusion complexes) in which a guest molecule is enclosed in the hydrophobic cavity of the cyclodextrin host without resort to primary valence forces. Thus, the components are bound as a consequence of geometric factors, and the presence of one component does not significantly affect the structure of the other component. Complexing a hydrophobic compound with cyclodextrin increases the stability and solubility of the hydrophobic compound. Applications of this phenomena have been found in many fields including pharmaceuticals, foods cosmetics and pesticides.

In pharmaceutical applications, complexing a drug with cyclodextrins for oral delivery can have many advantages. Among the benefits are the transformation of liquids into solids which can be formed into tablets, stabilization of drugs against volatilization and oxidation, reduction of bad taste or smell, improvement in the rate of dissolution of poorly soluble drugs and increases in blood levels of poorly water soluble drugs (Pitha, in *Controlled Drug Delivery*, Bruck, ed. Vol. 1, p. 125, (1983) CRC Press). From the limited research done on parenteral administration of cyclodextrin-complexed drugs, some of the same advantages found for oral delivery can also be observed. The undesirable side effects of drugs can be reduced with complexation with cyclodextrins. Such side affects include gastric irritation from oral delivery, local irritation and hemorrhagic areas from intramuscular injection, and local irritation from eye-drops (Szejtli, J., *Cyclodextrin Technology*, Kluwer Academic Publications, Boston (1988), pp. 186–306).

The addition of cyclodextrins to food products or cosmetics can also have many effects. In spices, food flavoring or perfume fragrances, cyclodextrins protect against oxidation, volatility, and degradation by heat or light (Hashimoto, H., "Application of Cyclodextrins to Food, Toiletries and Other Products in Japan," in *Proceedings of the Fourth International Symposium of Cyclodextrins*, O. Huber and J. Szejtli, eds. (1988) pp. 533–543). Cyclodextrins can also eliminate or reduce undesirable smells or tastes, and modify food or cosmetic textures.

Complexing pesticides with cyclodextrins can increase the bioavailability of poorly wettable or slightly soluble substances, and transform volatile liquids or sublimable solids into stable solid powders (Szejtli, J. (1988) supra at pp. 335-364; U.S. Pat. No. 4,923,853). Pesticides which are sensitive to light, heat or oxygen degradation can be stabilized by complexing with cyclodextrins.

Currently, production of cyclodextrins begins with the cultivation of an appropriate microorganism, e.g., *Bacillus macerans*, and separation, purification and concentration of the amylase enzyme. The enzyme is then used to convert a starch substrate to a mixture of cyclic and acyclic dextrins. Subsequent separation and purification of cyclodextrins is then required. The bacterial strain from which the enzyme is isolated and the length of time the starch conversion is allowed to progress determines the predominant form of cyclodextrin produced. Manufactures of α-cyclodextrins attempt to manipulate the reaction to preferentially make the specific cyclodextrin, however, the process is not easily controlled, and a mixture of cyclodextrins is obtained. At the present time β-cyclodextrin is the most widely commercialized form of cyclodextrin because the β-form is much cheaper to produce than the α- or γ-cyclodextrins.

In 1987, the U.S. market for cyclodextrins was predicted to reach $50 million per year within 2 years; that figure would double if the U.S. Food and Drug Administration approved the use of cyclodextrins in food (Seltzer, R., *Chem. Eng. News*, (May 1987) pp. 24–25). The world market is estimated to be twice the U.S. figure (Szejtli, J. (1988) supra at p. viii). The potential U.S. market for cyclodextrins has been predicted to reach as high as $245 million per year (Anon., Bioproc. Technol., November 1987). There is potentially a large market waiting to be tapped if the cost of cyclodextrins could be lowered through alternative production methods.

With the development of genetic engineering techniques, it is now possible to transfer genes from a variety of organism into the genome of a large number of different plant species. This process is preferable to plant breeding techniques whereby genes can only be transferred from one plant in a species to another plant in the same or a closely related species. It would thus be desirable to develop plant varieties through genetic engineering, which have increased capacity for starch synthesis, altered amylose/amylopectin ratios, altered distribution of low to high molecular weight chains in the amylopectin fraction and also starches with novel molecular weight characteristics. In this manner, useful starches with a variety of viscosity or texture differences may be obtained.

In addition, recognizing the disadvantages of bacterial-derived CGT-mediated cyclodextrin production, it is considered desirable to produce cyclodextrins where CGT is the expression product of a recombinant gene transferred into a plant host. In this method, generically known as molecular farming, plants are transformed with a structural gene of interest and the product extracted and purified from a harvested field of the transgenic plants. For example, human serum albumin has been produced in transgenic tobacco and potato (Sijmons, P. C. et al., *Bio/Technology* (1990) 8:217–221).

Extending the idea of molecular farming to cyclodextrins provides a means to lower production costs. One particularly desirable host plant for such transformation is potato because of the large amount of starch production in potato tubers. A typical tuber contains approximately 16% of its fresh weight as starch (Burton, W. G., *The Potato* (1966) 3rd Edition, Longman Scientific and Technical Publications, England, p. 361). Transformation of potato plants with the bacterial CGT structural gene linked to a tuber-specific promoter and a leader directing the enzyme, for example, to the amyloplast, provides a means to produce large quantities of cyclodextrins in tubers.

To this end, nucleic acid sequences which encode glycogen biosynthetic or degradative enzymes are desirable for study and manipulation of the starch biosynthetic pathway. In particular, these enzymes may be expressed in plant cells using plant genetic engineering techniques and targeted to a plastid where starch synthesis occurs. It was therefore considered desirable to apply recombinant deoxyribonucleic acid (rDNA) and related technologies to provide for modified reserve polysaccharides in transgenic plants.

Proceeding from the seminal work of Cohen & Boyer, U.S. Pat. No. 4,237,224, rDNA technology has become available to provide novel DNA sequences and to produce heterologous proteins in transformed cell cultures. In general, the joining of DNA from different organisms relies on the excision of DNA sequences using restriction endonucleases. These enzymes are used to cut donor DNA at very specific locations, resulting in gene fragments which contain the DNA sequences of interest. Alternatively, structural genes coding for desired peptides and regulatory control sequences of interest can now be produced synthetically to form such DNA fragments.

These DNA fragments usually contain short single-stranded tails at each end, termed "sticky-ends". These sticky-ended fragments can then be ligated to complementary fragments in expression vehicles which have been prepared, e.g., by digestion with the same restriction endonucleases. Having created an expression vector which contains the structural gene of interest in proper orientation with the control elements, one can use this vector to transform host cells and express the desired gene product with the cellular machinery available. Recombinant DNA technology provides the opportunity for modifying plants to allow the expression of desirable enzymes in planta.

However, while the general methods are easy to summarize, the construction of an expression vector containing a desired structural gene is a difficult process and the successful expression of the desired gene product in significant amounts while retaining its biological activity is not readily predictable. Frequently, bacterial-derived gene products are not biologically active when expressed in plant systems.

To successfully modify plants using rDNA, one must usually modify the naturally occurring plant cell in a manner in which the cell can be used to generate a plant which retains the modification. Even in successful cases, it is often essential that the modification be subject to regulation. That is, it is desirable that the particular gene be regulated as to the differentiation of the cells and maturation of the plant tissue. In the case of glycogen synthase, ADP-glucose pyrophosphorylase and/or cyclodextrin glycosyltransferase, it is also important that the modification be performed at a site where the product will be directed to contact the reserve polysaccharide regions of the modified plant. Thus, genetic engineering of plants with rDNA presents substantially increased degrees of difficulty.

In addition, the need to regenerate plants from the modified cells greatly extends the period of time before one can establish the utility of the genetic construct. It is also important to establish that the particular constructs will be useful in a variety of different plant species. Furthermore, one may wish to localize the expression of the particular construct in specific sites and it is desirable that the genetically modified plant retain the modification through a number of generations.

RELEVANT LITERATURE

The structural genes encoding the *E. coli* glycogen biosynthetic enzymes have been cloned (Okita, et al. (1981) *J. Biol. Chem.* 256: 6944–6952) and their nucleic acid sequences determined (Preiss, J. (1984) *Ann. Rev; Microbiol.* 38:419–458; Kumar et al. (1986) *J. Biol. Chem.* 261:16256–16259). Genes encoding mammalian glycogen synthases have also been cloned and their nucleic acid sequences determined (Browner, et al. *Proc. Nat. Acad. Sci.* (1989) 86:1443–1447; Bai, et al., *J. Biol Chem.* (1990) 265:7843–7848).

SUMMARY OF THE INVENTION

By this invention, nucleic acid constructs comprising at least one chimeric reserve polysaccharide modification enzyme gene sequence and promoter and control sequences operable in plant cells, are provided.

In particular, one aspect of this invention relates to constructs comprising sequences relating to reserve polysaccharide biosynthetic enzymes, such as glycogen biosynthetic enzymes, glycogen synthase and/or ADP-glucose pyrophosphorylase. Another aspect of the invention relates to constructs comprising sequences relating to polysaccharide degradation enzymes, including amylases such as cyclodextrin glycosyltransferases.

In one aspect of the invention, a sequence encoding a desired enzyme is joined to a sequence which encodes a transit peptide that provides for translocation of the enzyme to a plastid.

Other constructs of this invention provide sequences for transcription of the selected enzyme sequences in plant cells. To this end, transcriptional initiation regions that function to regulate expression of genes in plants are considered. Of particular interest are those regulatory regions that preferentially direct expression of genes in roots, tubers, and seeds, or in other plant parts that synthesize reserve starch. In addition, constructs may contain sequences encoding a marker enzyme for selection of transformed cells.

Expression constructs which comprise sequences which provide for transcriptional and translational regulation in plant cells of the sequences encoding the desired enzymes are of special interest. These constructs include, in the 5'-3' direction of transcription, a transcriptional/translational initiation control region, a sequence encoding a selected enzyme in reading frame, and a transcription/translation termination region, wherein the sequence encoding the enzyme is under the regulatory control of the initiation and termination regions. Expression constructs may also contain sequences which encode a transit peptide that provides for translocation of the enzymes to plastids and/or a marker enzyme.

Another aspect of the invention involves vectors which comprise sequences providing for transfer of desired sequences and integration into the genome of a plant cell. For example plant transformation vectors may include Agrobacterium T-DNA border region(s) to provide for transfer of the sequences to the plant cell.

Also considered part of this invention are plant cells containing nucleic acid sequences of the desired enzyme. Such plant cells are obtainable through transformation techniques which utilize, e.g., Agrobacterium to transfer DNA to the plant cells or through direct transfer techniques such as DNA bombardment, electroporation or microinjection. Plant cells containing the desired sequences can be regenerated to yield whole plants containing the sequences.

In yet another aspect of this invention, plant cells containing the desired enzymes or having reduced or increased starch precursor enzymes are considered. Of particular interest are plant cells in starch storage organs, such as roots, tubers or seeds. It is preferable that the enzyme be located in plastids, where starch synthesis occurs, and more preferably in amyloplasts, where reserve starch is synthesized and stored.

Further, it can be recognized that the modulation of polysaccharide modification enzymes in these plant cells has implications for modifying the starch content and/or composition of these cells. In this manner, plants or plant parts which synthesize and store starch may be obtained which have increased or decreased starch content and modified starch related properties such as specific gravity, free sugar content and/or novel and useful starches. In particular, potato starch having decreased amylose and modified amylopectin may be produced and further applications to modify starches consisting entirely of amylopectin such as that of waxy maize or a mutant potato, are also considered. Similarly, the starch from these plant parts can be harvested for use in commercial applications, or can be modified in planta to produce desired starch degradation products.

BRIEF DESCRIPTION OF THE DRAWINGS

FIGS. 1A–1C depicts a DNA sequence (SEQ ID NO: 11) for the *E. coil* glycogen synthase gene, glgA, generated, through Polymerase Chain Reaction (PCR) from *E. coli* K-12 618;

FIGS. 2A–2E depict the translated amino acid sequence (SEQ ID NO:12) of the PCR generated glgA gene;

FIGS. 3A–3E depict DNA sequence (SEQ ID NO: 13) and the translated amino acid sequence (SEQ ID NO:14) of the PCR generated *E. coli* ADP-glucose pyrophosphorylase gene, glgC, from *E. coli* K-12 618;

FIGS. 4A–4B depict the DNA sequence which encodes a SSU transit peptide from soybean plus 48 bp of DNA which encodes a mature SSU protein from pea, together with the amino acid sequence encoded by the reading frame (upper sequence); The DNA sequence of FIG. 4 and the translated amino acid sequences in three reading frames are represented as (SEQ. ID NO: 15–20);

FIGS. 5A–5C depict a comparison of DNA sequences from patatin 5' untranslated regions from *Solanum tuberosum* varieties Kennebec (top sequence, SEQ ID NO: 21) (generated by PCR) and Maris Piper (bottom sequence, SEQ ID NO: 22);

FIGS. 6A–6C depict a comparison of DNA sequences from patatin 5' untranslated regions from *Solanum tuberosum* varieties Russet Burbank (top sequence, SEQ ID NO: 22) (generated by PCR) and Maris Piper (bottom sequence, SEQ ID NO: 24);

FIGS. 7A–7I depicts a comparison of DNA sequences for native *Klebsiella pneumoneae* cyclodextrin glycosyltransferase (bottom sequence, SEQ ID NO: 25) and PCR-generated pCGT2 cyclodextrin glycosyltransferase (top sequence, SEQ ID NO: 26) (absence of bar between bases indicates difference in the two sequences); and FIGS. 8A–8C depicts a comparison of amino acid sequences for native *Klebsiella pneumoneae* cyclodextrin glycosyltransferase (bottom sequence, SEQ ID NO: 27) and pCGT2 cyclodextrin glycosyltransferase (top sequence, SEQ ID NO: 28) (absence of bar between residues indicates difference in the two sequences).

DETAILED DESCRIPTION OF THE INVENTION

The present invention relates to the expression of novel reserve polysaccharide modification enzyme gene sequences in plants. In particular, this invention is directed to a plant cell having nucleic acid sequences encoding such enzymes integrated in its genome as the result of genetic engineering. Cells containing a DNA or RNA (mRNA) sequence encoding the enzyme, as well as cells containing the enzyme, are also provided. Plants and, more particularly, plant parts may also be obtained which contain such enzyme gene sequences and/or such enzymes.

In considering the present reserve polysaccharide modification enzymes, there are two major classes presented: Biosynthetic enzymes which produce novel reserve polysaccharides, and starch degradation enzymes which produce novel starch degradation products. Representative of the first class of such enzymes include glycogen biosynthetic enzymes, which are not known to be endogenous to vascular plants.

The biosynthetic steps involved in glycogen synthesis in E. coli include: 1) the formation of ADP-glucose from ATP and glucose 1-phosphate, 2) the transfer of a glucose unit from ADP-glucose to a preformed maltodextrin primer via an α-1,4 linkage, and 3) the formation of α-1,6 glucosyl linkages from glycogen. The bacterial enzymes which catalyze the above reactions are ADP-glucose pyrophosphorylase (EC 2.7.7.27), glycogen synthase (EC 2.4.1.21), and Q-enzyme or branching enzyme (EC 2.4.1.18), respectively. The genes encoding these enzymes have been cloned and are also known as glgC, glgA, and glgB, respectively.

The pathway of glycogen biosynthesis in mammals is similar to that in bacteria, an exception being that UDP-glucose is the preferred glucose donor. The mammalian enzymes which catalyze glycogen biosynthetic reactions similar to those in bacteria are glucose-1-phosphate uridylyltransferase, glycogen synthase (EC 2.4.1.11), and 1,4-α-glucan branching enzyme. Genes encoding human muscle and rat liver glycogen synthases have been cloned and their sequences determined.

In particular, the glycogen biosynthesis enzyme glycogen synthase (glgA) is of special interest. The E. coli glycogen synthase is of particular interest in that the enzyme is similar to plant starch synthase with respect to being non-responsive to allosteric effectors or chemical modifications. Expression of a glycogen synthase enzyme in a plant host demonstrates biological activity even within an intact plant cell. Namely, potato plants having glgA expressed in potato tubers result in tubers having a deceased specific gravity; specific gravity being a commonly used measurement with respect to dry matter and starch contents of potato tubers (W. G. Burton, in The Potato, Third Edition, pub. Longman Scientific & Technical (1989) Appendix II, pp. 599–601). Further analysis of transgenic tubers having decreased specific gravity indicates that the starch in these tubers is modified. In particular, the percentage of amylose is decreased and the ratio of low m.w./high m.w. chains in the amylopectin fraction is increased. This phenotypic effect in planta is indicative of glgA biological activity. Additional disclosure concerning glycogen biosynthetic enzymes can be found in U.S. patent application Ser. No. 07/735,065, filed on Jul. 16, 1991 and U.S. patent application Ser. No. 07/632,383, filed on Dec. 21, 1990, now abandoned, the complete specifications of which are incorporated herein by this reference.

Other phenotypic starch modifications resulting from biological activity of glycogen biosynthetic enzymes in plants are also considered in this invention. Such altered phenotypes may result from enzymatic activity of these proteins on plant starch precursors, or from the inhibition of plant starch biosynthetic enzyme activities. Inhibition of plant enzymes, for example, could result through the production of inactive forms of the plant enzymes as the result of association with the glycogen biosynthetic enzymes. The inhibition of plant enzymes may then lead to plants having altered starch (such as branching patterns or molecular weight) and/or lowered starch levels. In addition, increased plant metabolites, such as sugars, could also result from starch alteration or inhibition caused by expression of glycogen biosynthetic enzymes. For example, transgenic potato tubers described herein are observed to have up to 3-fold increases in free sugar content.

Measurement of specific gravity or free sugar content may be useful to detect modified starch, with other methods, such as HPLC and gel filtration, also being useful. The glycogen synthase sequence may be employed as the sole glycogen biosynthetic enzyme or in conjunction with sequences encoding other glycogen biosynthetic enzymes.

In accordance with an additional aspect of the subject invention, the second class of reserve polysaccharide modification enzymes includes novel starch degradation enzymes which permit modification of the composition of host plants to increase synthesis of starch degradation products. Representative of such enzymes are amylase enzymes such as cyclodextrin glycosyltransferase enzymes, which can provide for the production of cyclodextrins from endogenous starch reserves in a variety of host plants.

As used herein, cyclodextrin glycosyltransferase (CGT) is intended to include any equivalent amylase enzyme capable of degrading starch to one or more forms of cyclodextrin. Considerations for use of a specific CGT in plants for the conversion of starch to cyclodextrin include pH optimum of the enzyme and the availability of substrate and cofactors required by the enzyme. The CGT of interest should have kinetic parameters compatible with the biochemical systems found in the host plant cell. For example, the selected CGT may compete for starch substrate with other enzymes.

The most preferred cyclodextrin forms are the α-, β- or γ-forms, although other higher forms of cyclodextrins, e.g. δ-, ε-, ζ- and η- forms, are also possible. Different CGT enzymes produce α, β, and γ CDs in different ratios. See, Szejtli, J., Cyclodextrin Technology (Kluwer Academic Publications, Boston) (1988), pp. 26–33 and Schmid, G., TIBTECH (1989) 7:244–248. In addition, various CGT enzymes can preferentially degrade the starch substrate to favor production of a particular cyclodextrin form. Some CGTs produce primarily β-CDs (Bender, H (1990) Carb. Res. 206:257–267; Kimura et al. (1987) Appl. Microbiol. Biotechnol. 26:149–153), whereas the Klebsiella CGT described in the following examples, produces α- and β-CDs in vitro at a ratio of 20:1 when potato starch is used as the substrate (Bender, H. (1990) supra). The use of these different CGTs in transgenic plants could result in different CD profiles and thus different utilities. For example, cyclodextrins have been reported as effective in inhibiting apple juice browning, with β-cyclodextrins producing better results than either α- or γ-cyclodextrins (Chemistry and Industry, London (1988) 13:410). In addition, it has been discovered that in vitro application of β-CDs to potato tuber slices inhibits discoloration, and in vitro application to whole potato tubers prevents a typical blackspot reaction caused by bruising. Additional disclosure concerning cyclydextrin glycosyltransferase enzymes can be found in U.S. patent application Ser. No. 07/536,392, filed on Jun. 11, 1990, the complete specification of which is incorporated herein by this reference.

An enzyme relevant to the present invention as including any sequence of amino acids, such as protein, polypeptide, or peptide fragment, which demonstrates the ability to catalyze a reaction involved in the modification of the reserve polysaccharide content of a transformed host cell.

In one aspect of the invention, the modification will result in the biosynthesis of glycogen. Thus, a glycogen biosynthetic enzyme of this invention will display activity towards a glucan molecule, although it may have preferential activity towards either ADP- or UDP-glucose. In plants, ADP-glucose is the preferred donor for starch biosynthetic reactions. Therefore, of particular interest in this invention are glycogen biosynthesis enzymes which also prefer ADP-glucose. Of special interest are glycogen biosynthesis enzymes obtainable from bacterial sources. Over 40 species of bacteria synthesize glycogen, including Escherichia and Salmonella.

Obtaining glycogen biosynthetic enzymes may be accomplished by a variety of methods known to those skilled in the art. For example, radiolabeled nucleic acid probes may be prepared from a known sequence which will bind to, and thus provide for detection of, other sequences. Glycogen biosynthesis enzymes may be purified and their sequences obtained through biochemical or antibody techniques, polymerase chain reaction (PCR) may be employed based upon known nucleic acid sequences, and the like.

In another aspect of the invention, the modification will result in the production of novel starch degradation products such as, e.g., cyclodextrins. The structural gene for a selected CGT can be derived from cDNA, from chromosomal DNA or may be synthesized, either completely or in part. For example, the desired gene can be obtained by generating a genomic DNA library from a source for CGT, such as a prokaryotic source, e.g. *Bacillus macerans, Bacillus subtilis* or, preferably, from *Klebsiella pneumoneae*.

Typically, a gene sequence obtainable from the use of nucleic acid probes will show 60–70% sequence identity between the target sequence and the given sequence encoding an enzyme of interest. However, lengthy sequences with as little as 50–60% sequence identity may also be obtained. The nucleic acid probes may be a lengthy fragment of the nucleic acid sequence, or may also be a shorter, oligonucleotide probe. Oligonucleotide probes can be considerably shorter than the entire nucleic acid sequence encoding a selected enzyme, but should be at least about 10, preferably at least about 15, and more preferably at least about 20-nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Hybridization and washing conditions can be varied to optimize the hybridization of the probe to the sequences of interest. Lower temperatures and higher salt (SSC) concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe. (See, for example, Beltz, et al. *Methods in Enzymology* (1983) 100:266–285).

It will be recognized by one of ordinary skill in the art that selected enzyme sequences of this invention may be modified using standard techniques of site specific mutation or PCR, or modification of the sequence may be accomplished in producing a synthetic nucleic acid sequence and will still be considered an enzyme nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of an enzyme relevant to the present invention may be a DNA or RNA sequence, derived from genomic DNA, cDNA, mRNA, or may be synthesized in whole or in part. The structural gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene may be synthesized using codons preferred by a selected plant host. Plant-preferred codons may be determined, for example, from the codons used most frequently in the proteins expressed in a particular plant host species. Other modifications of the gene sequences may result in mutants having slightly altered activity. Once obtained, an enzyme nucleic acid sequence of this invention may be combined with other sequences in a variety of ways.

Often, the sequences associated with reserve polysaccharide modification are used in conjunction with endogenous plant sequences. By "endogenous plant sequence" is meant any sequence which can be naturally found in a plant cell. These sequences include native (indigenous) plant sequences as well as sequences from plant viruses or plant pathogenic bacteria, such as Agrobacterium or Rhizobium species that are naturally found and functional in plant cells.

In one aspect of this invention, the selected enzyme sequence will be joined to a sequence encoding a transit peptide or functional portion of a transit peptide which is capable of providing for intracellular transport of a heterologous protein to a plastid in a plant host cell. Chloroplasts are the primary plastid in photosynthetic tissues, although plant cells are likely to have other kinds of plastids, including amyloplasts, chromoplasts, and leucoplasts. Transport into amyloplasts is preferred in this invention as these plastids are associated with reserve starch synthesis and storage. Any transit peptide providing for intracellular transport to a plastid is useful in this invention, such as the transit peptides from the precursor proteins of the small subunit of ribulose bisphosphate carboxylase (RUBISCO), acyl carrier protein (ACP), the waxy locus of maize, or other nuclear-encoded plastid proteins.

In addition to the identified transit peptide portion of a protein, it may be desirable to include sequences encoding a portion of the mature plastid-targeted protein to facilitate the desired intracellular transport of the glycogen biosynthetic enzyme. In one embodiment of this invention, the transit peptide from the small subunit of RUBISCO is utilized along with 48 bp of sequence encoding the amino terminal 16 amino acids of a mature small subunit protein.

Other endogenous plant sequences may be provided in nucleic acid constructs of this invention, for example to provide for transcription of the enzyme sequences. Transcriptional regulatory regions are located immediately 5' to the DNA sequences of the gene of interest, and may be obtained from sequences available in the literature, or identified and characterized by isolating genes having a desirable transcription pattern in plants, and studying the 5' nucleic acid sequences. Numerous transcription initiation regions which provide for a variety of constitutive or regulatable, e.g. inducible, expression in a plant cell are known. Among sequences known to be useful in providing for constitutive gene expression are regulatory regions associated with Agrobacterium genes, such as for nopaline synthase (Nos), mannopine synthase (Mas), or octopine synthase (Ocs), as well as regions coding for expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, patatin, zein, and the like.

Sequences to be transcribed are located 3' to the plant transcription initiation region and may be oriented, in the 5'-3' direction, in the sense orientation or the antisense orientation. In the sense orientation, an mRNA strand is produced which encodes the desired glycogen biosynthetic enzyme, while in antisense constructs, an RNA sequence complementary to an enzyme coding sequence is produced. The sense orientation is desirable when one wishes to produce the selected enzyme in plant cells, whereas the antisense strand may be useful to inhibit production of related plant enzymes. Regions of homology have been observed, for example, upon comparison of E. coli glgC sequence to that of a rice ADP glucose pyrophosphorylase. Either method may be useful in obtaining an alteration in the polysaccharide or dry matter content of a plant. The presence of the selected enzyme sequences in the genome of the plant host cell may be confirmed, e.g., by a Southern analysis of DNA or a Northern analysis of RNA sequences or by PCR methods.

In addition to sequences providing for transcriptional initiation in a plant cell, also of interest are sequences which provide for transcriptional and translational initiation of a desired sequence encoding a glycogen biosynthetic enzyme. Translational initiation regions may be provided from the source of the transcriptional initiation region or from the gene of interest. In this manner, expression of the selected enzyme in a plant cell is provided. The presence of the enzyme in the plant host cell may be confirmed by a variety of methods including a immunological analysis of the protein (e.g. Western or ELISA), as a result of phenotypic changes observed in the cell, such as altered starch content, altered starch branching, etc., or by assay for increased enzyme activity, and the like. If desired the enzyme may be harvested from the plant host cell or used to study the effect of the enzyme on plant cell functions, especially in the plastid organelles.

Other sequences may be included in the nucleic acid construct providing for expression of the selected enzymes ("expression constructs") of this invention, including endogenous plant transcription termination regions which will be located 3' to the desired enzyme encoding sequence. In one embodiment of this invention, transcription termination sequences derived from a patatin gene are preferred. Transcription termination regions may also be derived from genes other than those used to regulate the transcription in the nucleic acid constructs of this invention. Transcription termination regions may be derived from a variety of different gene sequences, including the Agrobacterium, viral and plant genes discussed above for their desirable 5' regulatory sequences.

Further constructs are considered which provide for transcription and/or expression of more than one selected enzyme. For example, one may wish to provide enzymes to plant cells which provide for modification of the starch synthesized, as well as for an increase or decrease in overall starch production. Examples of enzymes which may prove useful in modifying starch structure are those which catalyze reactions involving UDP- or ADP-glucose, for example glycogen synthase or branching enzyme. However, to provide for increased or decreased starch production, or the production of starch degradation products, one may wish to utilize sequences encoding enzymes which catalyze formation of the nucleotide-glucose molecule, such as ADP-glucose pyrophosphorylase in bacteria, or glucose-1-phosphate uridylyltransferase in mammals. Although plants typically utilize ADP-glucose, UDP-glucose may also be useful.

In providing for transcription and/or expression of the selected enzyme sequences, one may wish to limit these enzymes to plant cells which synthesize and store reserve starch. Towards this end, one can identify useful transcriptional initiation regions that provide for expression preferentially in the roots, tubers, seeds, or other starch-containing tissues of a desired plant species. These sequences may be identified from cDNA libraries using differential screening techniques, for example, or may be derived from sequences known in the literature. Of particular interest in a presently preferred embodiment of the invention is a transcriptional initiation region from the patatin gene of potato, which demonstrates preferential expression in the potato tuber. Similarly, other promoters which are preferentially expressed in the starch-containing tissues, such as the zein genes in corn, as opposed to other plant structures are desirable.

In developing the nucleic acid constructs of this invention, the various components of the construct or fragments thereof will normally be inserted into a convenient cloning vector, e.g. a plasmid, which is capable of replication in a bacterial host, e.g. E. coli. Numerous vectors exist that have been described in the literature, many of which are commercially available. After each cloning, the cloning vector with the desired insert may be isolated and subjected to further manipulation, such as restriction, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

The constructs of this invention providing for transcription and/or expression of the enzyme sequences of this invention may be utilized as vectors for plant cell transformation. The manner in which nucleic acid sequences are introduced into the plant host cell is not critical to this invention. Direct DNA transfer techniques, such as electroporation, microinjection or DNA bombardment may be useful. To aid in identification of transformed plant cells, the constructs of this invention may be further manipulated to include plant selectable markers. The use of plant selectable markers is preferred in this invention as the amount of experimentation required to detect plant cells is greatly reduced when a selectable marker is expressed. Useful selectable markers include enzymes which provide for resistance to an antibiotic such as gentamicin, hygromycin, kanamycin, and the like. Similarly, enzymes providing for production of a compound identifiable by color change, such as GUS, or luminescence, such as luciferase, are useful.

An alternative method of plant cell transformation employs plant vectors which contain additional sequences which provide for transfer of the desired enzyme sequences to a plant host cell and stable integration of these sequences into the genome of the desired plant host. Selectable markers may also be useful in these nucleic acid constructs to provide for differentiation of plant cells containing the desired sequences from those which have only the native genetic material. Sequences useful in providing for transfer of nucleic acid sequences to host plant cells may be derived from plant pathogenic bacteria, such as Agrobacterium or Rhizogenes, plant pathogenic viruses, or plant transposable elements.

When Agrobacterium is utilized for plant transformation, it may be desirable to have the selected nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri-containing the T-DNA for recombination may be armed (capable of causing gall formation), or disarmed (incapable of causing gall formation), the latter being permissible so long as a functional complement of the vir genes, which encode transacting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region(s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli,* and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the expression vectors in host Agrobacterium cells.

Utilizing vectors such as those described above, which can replicate in Agrobacterium is preferred. In this manner, recombination of plasmids is not required and the host *Agrobacterium vir* regions can supply transacting factors required for transfer of the T-DNA bordered sequences to plant host cells.

In general, the plant vectors of this invention will contain the selected enzyme sequence(s), alone or in combination with transit peptides, and endogenous plant sequences providing for transcription or expression of these sequences in a plant host cell. The plant vectors containing the desired sequences may be employed with a variety of plant cells, particularly plants which produce and store reserve starch. Plants of interest include, but are not limited to plants which have an abundance of starch in the seed, such as corn (e.g. *Zea mays*), cereal grains (e.g. wheat (Triticum spp.), rye (*Secale cereale*), triticale (*Triticum aestium*×*Secale cereale* hybrid), etc.), waxy maize, sorghum (e.g. Sorghum bicolor) and rice (e.g. *Oryza sativa*), in the root structures, such as potato (e.g., Irish (*Solanum tuberosum*), Sweet (*Ipomoea batatas*), and yam (Discorea spp.)), tapioca (e.g. cassava (*Manihot esculenta*)) and arrowroot (e.g., Marantaceae spp., Cycadaceae spp., Cannaceae spp., Zingiberaceae spp., etc.), or in the stem, such as sago (e.g. Palmae spp., Cycadales spp.). Starch is also found in botanical fruits, including for example tomato, apple and pear.

Also considered part of this invention are plants containing the nucleic acid sequences of this invention, and following from that, plants containing the selected enzymes as the result of expression of the sequences of this invention in plant cells or having a decreased expression of a native enzyme. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations either from seed or using vegetative propagation techniques.

Of particular interest are plant parts, e.g. tissues or organs, (and corresponding cells) which form and store reserve starch, such as roots, tubers, and seeds. Of more particular interest are potato tubers containing the selected enzymes. It can be recognized that the modification of enzymes in plants may also result in desirable alterations in the plant cells or parts. These alterations may include modification of dry matter content, free sugar content or of starch content and/or structure, or modification of specific gravity. The novel plant cells or plant parts can thus be harvested and used for isolation of the altered material.

Once the cells are transformed, transgenic cells may be selected by means of a marker associated with the expression construct. The expression construct will usually be joined with such a marker to allow for selection of transformed plant cells, as against those cells which are not transformed. As before, the marker will usually provide resistance to an antibiotic, e.g., kanamycin, gentamicin, hygromycin, and the like, or an herbicide, e.g. glyphosate, which is toxic to plant cells at a moderate concentration.

After transformation, the plant cells may be grown in an appropriate medium. In the case of protoplast transformations, the cell wall will be allowed to reform under appropriate osmotic conditions. In the case of seeds or embryos, an appropriate germination or callus initiation medium would be employed. For transformation in explants, an appropriate regeneration medium is used.

The callus which results from transformed cells may be introduced into a nutrient medium which provides for the formation of shoots and roots, and the resulting plantlets planted and allowed to grow to seed. During the growth, tissue may be harvested and screened for the presence of expression products of the expression construct. After growth, the transformed hosts may be collected and replanted. One or more generations may then be grown to establish that the enzyme structural gene is inherited in Mendelian fashion.

The ability to modify the composition of a host plant offers potential means to alter properties of the plant produce, such as, e.g., by the replacement of endogenous starch with oligosaccharides comprising glucopyranose units. These oligosaccharides, cyclodextrins for example, may then be purified away from the other plant components. For example, by modifying crop plant cells by introducing a functional structural gene expressing a selected enzyme, one can provide a wide variety of crops which have the ability to produce starch degradation products, and desirably such production will be effected without damaging the agronomic characteristics of the host plant. In this manner, substantial economies can be achieved in labor and materials for the production of starch degradation products, while minimizing the detrimental effects of starch degradation on the host plants.

Preferably, the activity of the starch degradation enzyme will be localized in the starch storage organelles, tissues or regions of the host plant, e.g., the amyloplast of a host potato tuber. The structural gene will manifest its activity by mediating the production of degradation products in at least one portion of the genetically modified host plant.

The following examples serve to illustrate certain preferred embodiments and aspects of the present invention and are not to be construed as limiting the scope thereof.

EXPERIMENTAL

In the experimental disclosure which follows, the following abbreviations apply: eq (equivalents); M (Molar); mM (millimolar); μM (micromolar); N (Normal); mol (moles); mmol (millimoles); μmol (micromoles); nmol (nanomoles); kg (kilograms); g (grams); mg (milligrams); μg (micrograms); ng (nanograms); L (liters); ml (milliliters); μl (microliters); cm (centimeters); mm (millimeters); μm (micrometers); nm (nanometers); V (volts); μF (microfarads) and °C. (degrees Centigrade).

In order to demonstrate the practice of the present invention in utilizing reserve polysaccharide biosynthetic enzymes, the following examples convey an embodiment for the biosynthesis of glycogen.

EXAMPLE 1

Cloning of Glycogen Biosynthetic Enzyme Genes
A. Cloning and Sequencing of a GlgA Gene From *E. coli*

Total genomic DNA is prepared from *E. coli* K12 618 (Leung et al., *J. of Bacteriology* (1986) 167:82–88) by growing a 5 ml culture in ECLB (Maniatis, T. et al., *Molecular Cloning: A Laboratory Manual*, (1982) Cold Spring Harbor, N.Y.) overnight at 37° C. The bacteria are pelleted by centrifugation for 10 minutes at 4500×g, the supernatant is discarded, and the pellet is resuspended in 2.5 ml of 10 mM Tris, 1 mM EDTA buffer. To this suspension is added 500 μl of a 5 mg/ml Pronase® protease (Calbiochem Brand Biochemicals; La Jolla, Calif.) solution and 2 ml of 2% lauryl sulfate, sodium salt (Sigma; St. Louis, Mo.), with gentle mixing, and the suspension is incubated at 37° C. for 50 minutes. A clear solution indicates that the bacteria have lysed. The solution is then extracted with 5 ml phenol, then 5 ml phenol:chloroform:isoamyl alcohol (25:24:1), followed by 5 ml chloroform. Nucleic acids are precipitated from the aqueous phase with 1/10 volume of 3M sodium acetate and two volumes of 100% ethanol, and the tube is incubated at room temperature for 1 hour. Nucleic acids are removed from solution and resuspended in 1 ml water. A second ethanol precipitation is performed and the nucleic acids are resuspended in 200 μl of 10 mM Tris, 1 mM EDTA buffer.

Synthetic oligonucleotides, str1 and str2, corresponding to sequences flanking the 1.4 kb glgA (glycogen synthase—EC 2.4.1.21) gene of *E. coli* (Kumar et al., *J. of Biol. Chemistry* (1986) 261:16256–16259) and containing restriction sites for BglII (str1) and SalI (str2) are synthesized on an Applied Biosystems 380A DNA synthesizer (Foster City, Calif.) in accordance with the manufacturer's instructions.

The nucleic acid preparation of *E. coli* is treated with RNAse and the DNA is used as a template in a polymerase chain reaction (PCR) with str1 and str2 as primers. A Perkin-Elmer/Cetus (Norwalk, Conn.) thermal cycler is used with the manufacturer's reagents and in accordance with the manufacturer's instructions. The reaction mixture contains 41.5 μl $H_2O$, 10 μl 10× reaction buffer, 16 μl dNTP's [1.25 mM dCTP, dATP, dGTP & dTTP], 5 μl str1 (20 mM), 5μl str2 (20 mM), 22 μl total *E. coli* DNA (0.05 μg/μl), and 0.5 μl Taq polymerase. The reaction is performed for 15 cycles with melting (denaturation) for 1 minute at 94° C., annealing (hybridization) for 2 minutes at 37° C. and chain elongation for 3 minutes at 72° C. The reaction is then performed for an additional 10 cycles with melting for 1 minute at 94° C., annealing for 2 minutes at 37° C. and chain elongation at 72° C. for 3 minutes 15 seconds initially and increasing the time by 15 seconds each cycle so that the last cycle is 5 minutes 45 seconds.

The resulting PCR products (~1.4 kb) are digested with BglII and SalI and ligated into a SalI and BglII digest of pCGN789, a pUC based vector similar to pUC119 with the normal polylinker replaced by a synthetic linker which contains the restriction digest sites EcoRI, SalI, BglII, PstI, XhoI, BamHI, and HindIII. The ligated DNA is transformed into *E. coli* DH5α. The transformed cells are plated on ECLB containing penicillin (300 mg/L), IPTG and X-Gal (Vieira and Messing, *Gene* (1982) 19:259–268). White colonies are picked to ECLB containing penicillin (300 mg/L) and flooded with $I_2$/KI (0.2% $I_2$ in 0.4% KI). Clones producing a brown color, which indicates excess starch production, are selected. One clone, glgA-2, is selected and the DNA and translated amino acid sequences are determined (see, FIGS. 1 and 2 and SEQ ID NOS: 1–2). The DNA sequence is 98% homologous to the published sequence (Kumar et al, supra) and 96% homologous at the amino acid level.

B. Cloning and Sequencing of a GlgC Gene From *E. coli*

Synthetic oligonucleotides, glgC1 and glgC2, corresponding to sequences flanking the 1.3 kb glgC (ADP-glucose pyrophosphorylase - EC 2.7.7.27) gene of *E. coil* (Baecker et al., *J. of Biol. Chemistry* (1983) 258:5084–5088) and containing restriction sites for BglII (glgC1) and SalI (glgC2) are synthesized on an Applied Biosystems 380A DNA synthesizer (Foster City, Calif.) in accordance with the manufacturer's instructions.

Total genomic DNA is prepared from *E. coli* K12 618 as described above. The nucleic acid preparation of *E. coli* is treated with RNAse and the DNA is used as a template in a polymerase chain reaction (PCR) with glgC1 and glgC2 as primers. A Perkin-Elmer/Cetus (Norwalk, Conn.) thermal cycler is used with the manufacturer's reagents as described above.

The resulting PCR products (~1.3 kb) are digested with BglII and SalI and ligated into a SalI and BglII digest of pCGN789 (described above). The ligated DNA is transformed into *E. coli* DH5α, and the transformed cells are plated as described above. Clones producing excess starch are selected as described above. One clone, pGlgC-37, is selected and the DNA sequence (SEQ ID NO: 3) determined (see, FIG. 3). The DNA sequence is 99% homologous to the published sequence (Baecker et al, supra) of glgC from *E. coli* K-12. The glgC from *E. coli* 618 is a mutant and the amino acid sequence of this mutant differs from that of *E. coli* K-12 at five amino acids (Lee et al., *Nucl. Acids Res.* ; (1987) 15:10603). The translated amino acid sequence of pGlgC-37 differs from that of the glgC from *E. coli* 618 at a single amino acid; the asparagine (Asn) at position 361 of the *E. coli* 618 mutant is an aspartate (Asp) in the translated amino acid sequence of pGlgC-37 (FIG. 3).

EXAMPLE 2

Attachment of Glycogen Genes to SSU Leader Sequence

A. Construction of SSU+aroA Transit Peptide

Plasmid pCGN1132 contains a 35S promoter, ribulosebisphosphate carboxylase small subunit (5'-35S-SSU) leader from soybean plus 48 bp of mature small subunit (SSU) gene from pea, and aroA sequence (the gene locus which encodes 5-enolpyruvyl-3-phosphoshikimate synthetase (EC 2.5.1.19)). It is prepared from pCGN1096, a plasmid containing a hybrid SSU gene, which carries DNA encoding mature SSU protein from pea, and SstI and EcoRI sites 3' of the coding region (used in the preparation of pCGN1115, a plasmid having a 5'-35S-SSU+48-aroA-tml-3' sequence) and pCGN1129, (a plasmid having a 35S promoter in a chloramphenicol resistance gene (Cam$^r$) backbone).

Construction of pCGN1096

The aroA moiety of pCGN1077 is removed by digestion with SphI and SalI. (The construction of pCGN1077 and other constructs hereunder are described in detail in copending U.S. application Ser. No. 06/097,498, filed Sep. 16, 1987, which is hereby incorporated by reference). In its place is cloned the region coding for the mature pea SSU protein, as an SphI-PstI fragment, which is then excised with SphI and SalI. The resulting plasmid, pCGN1094, codes for a hybrid SSU protein having the transit peptide of the soybean clone, and the mature portion of the pea clone and contains SstI and EcoRI sites 3' of the coding region. The HindIII to BamHI region of transposon Tn6 (Jorgensen et al., *Mol. Gen. Genet.* (1979) 177:65) encoding the kanamycin resistance gene (Kan$^r$) is cloned into the same sites of pBR322 (Bolivar et al., *Gene* (1977) 2:95–133) generating pDS7. The BglII site 3' of the Kan$^r$ gene is digested and filled in with the large fragment of *E. coli* DNA polymerase 1 and deoxynucleotides triphosphate. An SstI linker is ligated into the blunted site, generating plasmid pCGN1093. Plasmid pPMG34.3 is digested with SalI, the site filled in as above and EcoRI linkers are ligated into the site resulting in plasmid pCGN1092. The latter plasmid is digested with SstI and SmaI and the Kan$^r$ gene excised from pCGN1093 with SstI and SmaI is ligated in, generating pCGN1095. The Kan$^r$ and aroA genes are excised as a piece from pCGN1095 by digestion with SstI and EcoRI and inserted into the SstI and EcoRI sites of pCGN1094, producing pCGN1096. Summarizing, pCGN1096 contains (5'-3') the following pertinent features: The SSU gene—a polylinker coding for PstI, SalI, SstI, and KpnI—the Kan$^r$ gene—SmaI and BamHI restriction sites—the aroA gene without the original ATG start codon.

Construction of pCGN1115

Plasmid pCGN1096 is digested to completion with SalI and then digested with exonuclease Bal31 (BRL; Gaithersburg, Md.) for 10 minutes, thus deleting a portion of the mature SSU gene. The resulting plasmid is then digested with SmaI to eliminate the Kan$^r$ gene and provide blunt ends, recircularized with T4 DNA ligase and transformed into *E. coli* LC3 (Comai et al., *Science* (1983) 221:370–371), an aroA mutant. DNA isolated from aroA$^+$ and Kan$^r$ colonies is digested with BamHI and SphI and ligated with BamHI- and SphI-digested M13mp18 (Norrander et al., *Gene* (1983) 26:101–106 and Yanisch-Perron et al., *Gene* (1985) 33:103–119) DNA for sequencing. Clone 7 has 48bp of the mature SSU gene remaining and the 3'-end consists of phe-glu-thr-leu-ser (SEQ ID NO: 1). Clone 7 is transformed into *E. coli* strain 71–18 (Yanisch-Perron et al. (1985) supra) and DNA isolated from transformants is digested with SphI and ClaI to remove the 0.65 kb fragment containing the 48 bp of mature protein and the 5'-end of the aroA gene. Plasmid pCGN1106 (Comai, L. et al., *J. Biol. Chem.* (1988) 263:15104–15109) is also digested with SphI and ClaI and the 6.8 kb isolated vector fragment is ligated with the 0.65 kb fragment of clone 7 to yield pCGN1115 (5'-35S-SSU+48-aroA-tml-3').

Construction of pCGN1129

The 7.2 kb plasmid pCGN1180 (35S-SSU+70-aroA-ocs3') (Comai et al. (1988) supra) and the 25.6 kp plasmid pCGN594 (LB-Gent$^r$-ocs5'-Kan$^r$-ocs3 '-RB) (construction of pCGN594 is described in co-pending U.S. application Ser. No. 07/382,802, filed Jul. 19, 1989) are digested with HindIII and ligated together to yield the 32.8 kb plasmid pCGN1109 (LB-Gent$^r$-35S-SSU+70-aroA-ocs3'-ocs5'-Kan$^r$-ocs3 '-RB).

Plasmid pCGN1109 is digested with EcoRI to delete an internal 9.1 kb fragment containing the SSU leader plus 70 bp of the mature SSU gene, the aroA gene and its ocs3' terminator, the Amp$^r$ backbone from pCGN1180 and ocs5'-Kan$^r$-ocs3' from pCGN594. The EcoRI digest of pCGN1109 is then treated with Klenow fragment to blunt the ends, and an XhoI linker (dCCTCGAGG) (New England Biolabs.; Beverly, Mass.) is ligated in, yielding pCGN1125 (LB-35S-RB).

Plasmid pCGN1125 is digested with HindIII and BglII to delete the 0.72 kb fragment of the 35S promoter. This digest is ligated with HindIII- and BamHI-digested Cam$^r$ vector, pCGN786 (described in co-pending U.S. application Ser. No. 07/382,803, filed Jul. 19, 1989). The resulting 3.22 kb plasmid, pCGN1128, contains the 35S promoter with a 3' multilinker in a Cam$^r$ backbone.

Plasmid pCGN1128 is digested with HindIII, treated with Klenow fragment to blunt the ends and ligated with BglII linkers to yield pCGN1129, thus changing the HindIII site located 5' to the 35S promoter into a BglII site.

B. Transit Peptide Joined to GlgA Gene Plasmid pCGN1115 is digested with SalI to remove a 1.6kb fragment containing the SSU leader plus 46bp of the mature SSU gene and the aroA gene. An XhoI digest of pCGN1129 opens the plasmid 3' to the 35S promoter. Ligation of these two digests yields the 4.8 kb plasmid pCGN1132, containing 5'-35S-SSU leader plus 48 bp of mature SSU-aroA.

Plasmid pGlgA-2 is digested with BglII and SalI and ligated to pCGN1132 that has been digested with BamHI and SalI. A clone containing 5'-35S-SSU+48bp-glgA-3' is selected and designated pCGN1439.

C. Transit Peptide Joined to GlgC Gene

Plasmid pGlgC-37 is digested with BglII and SalI and ligated to pCGN1132 that has been digested with BamHI and SalI. A clone containing 5'-35S-SSU+48bp-glgC-3' is selected and designated pCGN1440.

EXAMPLE 3

Cloning of Patatin Regulatory Regions and Preparation of Patatin-5'-nos-3' Expression Cassettes This example describes the cloning of a patatin-5' regulatory region from potato and the preparation of patatin-5'-nos-3' expression cassette pCGN2143.

Genomic DNA is isolated from leaves of *Solanum tuberosum* var. Kennebec as described in Dellaporta et al., *Plant Mol. Biol. Reporter* (1983) 1(4):19–21), with the following modifications: approximately 9 g fresh weight of leaf tissue is ground, a polytron grinding is not performed and in the final step the DNA is dissolved in 300 µl of 10 mM Tris, 1 mM EDTA, pH 8.

A synthetic oligonucleotide, pat1, containing digestion sites for NheI, PstI and XhoI with 24 bp of homology to the 5'-region of a 701 bp fragment (coordinates 1611 to 2313) 5' to a class I patatin gene, isolated from *Solanum tuberosum* var. Maris Piper (Bevan et al., NAR (1986) 14:4625–4638), is synthesized (Applied BioSystems 380A DNA synthesizer). A second synthetic oligonucleotide, pat2, containing digestion sites for BamHI and SpeI with 25 bp of homology to the 3' region of the 703 bp piece is also synthesized.

Using the genomic potato DNA as a template, and pat1 and pat2 as primers, a polymerase chain reaction (PCR) is performed in a Perkin-Elmer/Cetus thermal cycler with the manufacturer's reagents and in accordance with the manufacturer's instructions. The reaction contains 62.5 µl H₂O, 10 µl 10× Reaction buffer, 16 µl dNTP's [1.25 mM dCTP, dATP, dGTP & dTTP], 5 µl pat1 (20 mM), 5 µl pat2 (20mM), 1 µl potato genomic DNA (3 µg/µl), 0.5 µl Taq polymerase. The PCR is performed for 25 cycles with melting for 1 minute at 94° C., annealing for 2 minutes at 37° C. and chain elongation for 3 minutes at 72° C. The resulting PCR product fragments (approximately 700 bp) are digested with NheI and BamHI. Plasmid pCGN1586N (5-D35S-TMVΩ'-nos-3'; pCGN1586 (described below) having a NheI site 5' to the 35S region) is digested with NheI and BamHI to delete the D35S-Ω' fragment. Ligation of NheI-BamHI digested pCGN1586N, which contains the nos-3' region, and the PCR fragments yields a patatin-5'-nos3' cassette with SpeI, BamHI, SalI and SstI restriction sites between the 5' and 3' regions for insertion of a DNA sequence of interest.

The 5' region of a clone, designated pCGN2143 is sequenced. Plasmid pCGN2143 has a Kennebec patatin-5' region that is 702 bp in length and 99.7% homologous to the native sequence (as reported by Bevan (1986) supra).

Synthetic oligonucleotides, pat5 and pat6, are prepared as described above. Pat5 and pat6 contain complementary sequences which contain the restriction digest sites NheI, XhoI and PstI. Pat5 and pat6 are annealed to create a synthetic linker. The annealed linker is ligated to pCGN2143 that has been linearized with EcoRI and treated with Klenow polymerase to generate blunt ends. A plasmid, pCGN2162 which has the following restriction sites at the 3' end of nos is selected: 5'-EcoRI-NheI-XhoI-PstI-EcoRI.

Construction of pCGN1586/1586N

Plasmid pCGN2113 (6.1 kb) contains a double-35S promoter (D35S) and the tml-3' region with multiple cloning sites between them, contained in a pUC-derived plasmid backbone bearing an ampicillin resistance gene (Ampr). The promoter/tml cassette is bordered by multiple restriction sites for easy removal. Plasmid pCGN2113 is digested with EcoRI and SacI, deleting the 2.2 kb tml-3' region. Plasmid pBI221.1 (Jefferson, R. A., *Plant Mol. Biol. Reporter* (1987) 5:387–405) is digested with EcoRI and SacI to delete the 0.3 kb nos-3' region. The digested pCGN2113 and pBI221.1 DNAs are ligated together, and the resultant 4.2 kb recombinant plasmid with the tml-3' of pCGN2113 replaced by nos-3' is designated pCGN1575 (5'-D35S-nos-3').

Plasmid pCGN1575 is digested with SphI and XbaI, blunt ends generated by treatment with Klenow fragment, and the ends are ligated together. In the resulting plasmid, pCGN1577, the SphI, PstI, SalI and XbaI sites 5' of the D35S promoter are eliminated.

Plasmid pCGN1577 is digested with EcoRI, the sticky ends blunted by treatment with Klenow fragment, and synthetic BglII linkers (d(pCAGATCTG) New England Biolabs, Inc.; Beverly, Mass.) are ligated in. A total of three BglII linkers are ligated into the EcoRI site creating two PstI sites. The resulting plasmid, termed pCGN1579 (D35S-nos-3'), has a 3' polylinker consisting of 5'-EcoRI, BglII, PstI, BglII, PstI, BglII, EcoRI-3'[1].

A tobacco mosaic virus omega' (TMVΩ) region (Gallie et al., NAR (1987) 15(21) :8693–8711) with BglII, NcoI, BamHI, SalI and SacI restriction sites:

BglII
5'-CAGGAGATCT TATTTTTACA ACAATTACCA ACAACAACAA ACAACAAACA
ACATTACAAT TACTATTTAC AATTACACCA TGGATCCGTC GACGAGCTC 3'
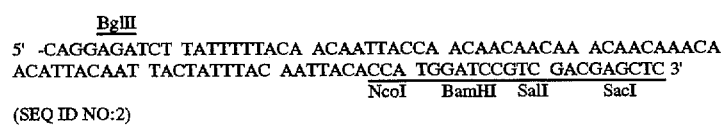

(SEQ ID NO:2)

is synthesized on an Applied Biosystems® 380A DNA synthesizer and digested with BglII and SacI. Plasmid pCGN1577 is digested with BamHI and SacI and the synthetic TMVΩ is ligated in between the 5'-D35S and nos-3' regions. The resulting plasmid is designated pCGN1586 (5'-D35S-TMVΩ'-nos-3'). Plasmid pCGN1586N is made by digesting pCGN1586 with HindIII and filling in the 5' overhang with Klenow fragment, thus forming a NheI site 5' to the D35S region.

Plasmid pCGN2143 is also described in co-pending U.S. application Ser. No. 07/536,392 filed Jun. 11, 1990, which is hereby incorporated by reference.

EXAMPLE 4

Preparation of Binary Vectors

This example describes the construction of a binary vector containing: (1) the patatin-5' region from *Solanum tuberosum* var. Kennebec, (2) DNA encoding a transit peptide from soybean RuBisCo SSU protein, (3) 48 bp of DNA encoding 16 amino acids of mature RuBisCo SSU protein from pea, (4) the glgA coding region from *E. coli* 618 and (5) the nos-3' region.

A. GlgA Construct

Plasmid pCGN2162 prepared as described in Example 3 is digested with SpeI and SalI, opening the plasmid between the patatin-5' region and nos-3' region. Plasmid pCGN1439 (described in Example 2) is digested with XbaI and SalI and ligated with pCGN2162 to yield pCGN1454. Plasmid pCGN1454 consists of 5'-Kennebec patatin-SSU+48-glgA-nos3'.

Plasmid pCGN1454 is digested with XhoI and treated with Klenow polymerase to generate blunt ends. Plasmid pCGN1557 is digested with XbaI and treated with Klenow polymerase to generate blunt ends. The fragments resulting from the digests are ligated together. The transformation is plated onto ECLB containing gentamycin, IPTG and X-Gal. White colonies are picked and screened for ampicillin sensitivity. Gent$^r$, Amp$^s$ clones are analyzed and two clones are selected. Plasmid pCGN1457 has the 5'patatin-SSU+48bp-glgA-nos3' inserted into pCGN1557 such that it transcribes in the opposite direction from the 35S-Kan$^r$-tml gene. Plasmid pCGN1457B has the 5'patatin-SSU+48bp-glgA-nos3' inserted into pCGN1557 such that it transcribes in the same direction as the 35S-Kan$^r$-tml gene.

B. GlgC Construct

Plasmid pCGN2162 prepared as described in Example 3 is digested with SpeI and SalI, opening the plasmid - between the patatin-5' region and nos-3' region. Plasmid pCGN1440 (described in Example 2) is digested with XbaI and SalI and ligated with pCGN2162 to yield pCGN1453. Plasmid pCGN1453 consists of 5'-Kennebec patatin-SSU+48-glgC-nos3'.

Plasmid pCGN1453 is digested with PstI and ligated to a PstI digest of pCGN1557. The transformation is plated as described above and colonies are screened for ampicillin sensitivity. Gent$^r$, Amp$^s$ clones are analyzed and one clone, pCGN1455, is selected. Plasmid pCGN1455 has the 5'patatin-SSU+48bp-glgC-nos3' inserted into pCGN1557 such that it transcribes in the same direction as the 35S-Kan$^r$-tml gene.

C. Construction of pCGN1557

Plasmid pCGN1557 (McBride and Summerfelt, *Plant Mol. Biol.* (1990) 14(27):269–276) is a binary plant transformation vector containing the left and right T-DNA borders of *Agrobacterium tumefaciens* octopine Ti-plasmid pTiA6 (Currier and Nester, *J. Bact.* (1976) 126:157–165), the gentamicin resistance gene (Gen$^r$) of pPH1JI (Hirsch and Beringer, *Plasmid* (1984) 12:139–141), an *Agrobacterium rhizogenes* Ri plasmid origin of replication from pLJbB11 (Jouanin et al., *Mol. Gen. Genet.* (1985) 201:370–374), a 35S promoter-Kan$^r$-tml-3' region capable of conferring kanamycin resistance to transformed plants, a ColE1 origin of replication from pBR322 (Bolivar et al. (1977) supra) and a lacZ' screenable marker gene from pUC18 (Yanisch-Perron et al., (1985) supra). The construction of pCGN1557 is also described in co-pending U.S. application Ser. No. 07/494,722, filed Mar. 16, 1990.

EXAMPLE 5

Preparation of Transgenic Plants

This example describes the transformation of *Agrobacterium tumefaciens* with glycogen biosynthetic enzyme gene nucleic acid constructs in accordance with the present invention and the cocultivation of these *A. tumefaciens* with plant cells to produce transgenic plants containing the glycogen constructs.

A. Transformation of *Agrobacterium tumefaciens*

Cells of *Agrobacterium tumefaciens* strain 2760 (also known as LBA4404, Hoekema et al., *Nature* (1983) 303:179–180) are transformed with binary vectors, such as pCGN1457, pCGN1457B and pCGN1455 (as described in Example 4) using the method of Holsters, et al., (*Mol. Gen. Genet.*, (1978) 163:181–187). The transformed *A. tumefaciens* are then used in the co-cultivation of plants.

The Agrobacterium are grown on AB medium (K$_2$HPO$_4$ 6 g/L, NaH$_2$PO$_4$.H$_2$O 2.3 g/L, NH$_4$Cl 2 g/L, KCl 3 g/L, glucose 5 g/L, FeSO$_4$ 2.5 mg/L, MgSO$_4$ 246 mg/L, CaCl$_2$ 14.7 mg/L, 15 g/L agar), plus 100 µg/L gentamycin sulfate and 100 µg/L streptomycin sulfate for 4–5 days. Single colonies are inoculated into 10 ml of MG/L broth (per liter: 5 g mannitol, 1 g L-Glutamic acid or 1.15 g sodium glutamate, 0.5 g KH$_2$PO$_4$, 0.10 g NaCl, 0.10 g MgSO$_4$0.7H$_2$O, 1 µg biotin, 5 g tryptone, 2.5 g yeast extract; adjust pH to 7.0) and are incubated overnight in a shaker at 30° C. and 180 rpm. Prior to co-cultivation, the Agrobacterium culture is centrifuged at 12,000×g for 10 minutes and resuspended in 20 ml of MS medium (#510–1118, Gibco; Grand Island, N.Y.).

B. Cocultivation with Potato Cells

Feeder plates are prepared by pipetting 0.5 ml of a tobacco suspension culture (~10$^6$cells/ml) onto 0.8% agar co-cultivation medium, containing Murashige and Skoog salts (#510–117, Gibco; Grand Island, N.Y.), thiamine-HCl (1.0 mg/L), nicotinic acid (0.5 mg/L), pyridoxine HCl (0.5 mg/L), sucrose (30 g/L), zeatin riboside (5 µM), 3-indoleacetyl-DL-aspartic acid (3 µM), pH 5.9. The feeder plates are prepared one day in advance and incubated at 25° C. A sterile 3 mm filter paper disk is placed on top of the tobacco cells after the suspension cells have grown for one day.

Tubers of *Solanum tuberosum* var Russet Burbank between the age of 1 and 6 months post harvest are peeled and washed in distilled water. All subsequent steps are carried out in a flow hood using sterile techniques. For surface sterilization, tubers are immersed in a solution of 10% commercial bleach (sodium hypochlorite) with 2 drops of Ivory® liquid soap per 100 ml for 10 minutes. Tubers are rinsed six times in sterile distilled water and kept immersed in sterile liquid MS medium (#1118, Gibco; Grand Island; N.Y.) to prevent browning. Tuber discs (1–2 mm thick) are prepared by cutting columns of potato tuber with a ~1 cm in diameter cork borer and slicing the columns into discs of the desired thickness. Discs are placed into the liquid MS medium culture of the transformed *Agrobacterium tumefaciens* containing the binary vector of interest (1×10$^7$–1×10$^8$ bacteria/ml) until thoroughly wetted. Excess bacteria are removed by blotting discs on sterile paper towels. The discs are co-cultivated with the bacteria for 48 hours on the feeder plates and then transferred to regeneration medium (co-cultivation medium plus 500 mg/L carbenicillin and 100 mg/L kanamycin). In 3 to 4 weeks, shoots develop from the discs.

When shoots are approximately 1 cm, they are excised and transferred to a 0.8% agar rooting medium containing MS salts, thiamine-HCl (1.0 mg/L), nicotinic acid (0.5 mg/L), pyridoxine-HCl (0.5 mg/L), sucrose (30 g/L), carbenicillin (200 mg/L) and kanamycin (100–200 mg/L) pH 5.9. Plants are rooted two times with at least one rooting taking place on rooting medium with the higher level of kanamycin (200 mg/L). Plants which have rooted twice are then confirmed as transformed by performing NPTII blot activity assays (Radke, S. E. et al, *Theor. Appl. Genet.* (1988) 75:685–694). Plants which are not positive for NPTII activity are discarded.

EXAMPLE 6

Analysis of Tubers from Transformed Potato Plants

In this Example, measurement of specific gravity in tubers from transgenic potato plants is described.

Rooted plants, transformed as described in Example 5, are cut into five sections at the internodes and each section is rooted again, also as described in Example 5. The newly rooted plants are transplanted from rooting medium to soil and placed in a growth chamber (21° C., 16 hour days with 250–300 µE/m$^2$/sec). Soil is prepared as follows: For about 340 gallons, combine 800 pounds 20/30 sand (approximately 14 cubic feet), 16 cubic feet Fisons Canadian Peat Moss, 16 cubic feet #3 vermiculite, and approximately 4.5 pounds hydrated lime in a Gleason mixer. The soil is steamed in the mixer for two hours; the mixer mixes for about 15 seconds at intervals of fifteen minutes over a period of one hour to ensure even heating throughout the soil. During and after the process of steaming, the soil reaches temperatures of at least 180° F. for one hour. The soil is left in the mixer until the next day. At that time, hydrated lime is added, if necessary, to adjust the pH to range between 6.30 and 6.80.

The relative humidity of the growth chamber is maintained at 70–90% for 2–4 days, after which the humidity is maintained at 40–60%. When plants are well established in the soil, after approximately two weeks, they are transferred to a greenhouse. In the greenhouse, plants are grown in 6.5 inch pots in a soil mix of peat:perlite:vermiculite (11:1:9), at an average temperature of 24° C. day/12° C. night. Day length is approximately 12 hours and light intensity levels vary from approximately 600 to 1000 µE/m$^2$/ sec.

Tubers from each plant are harvested and washed 14 weeks after transfer to the greenhouse. Immediately after harvest, three to five uniformly sized tubers from each pot are weighed and their specific gravity determined. In determining specific gravity, the tubers from each plant are first collectively weighed in air and then collectively weighed in water. Specific gravity is determined, where x=the weight of tubers in air and y=the weight of tubers in water, as x/(x–y).

In general, the specific gravities of tubers from five replicates of plants transformed with the glgA constructs (pCGN1457 and pCGN1457B) and of tubers from control plants are determined. Control plants include regenerated non-transformed potato plants and transgenic potato plants which lack the glgA constructs. Controls are subjected to the transformation and regeneration culture and growth conditions described above in production of glgA transformed plants. To compare values from each tuber sample, the specific gravity measurements are converted to reflect % total solids content of tubers. Percent total solids is calculated as (specific gravity)×(199.63)–194.84 (Porter, et al., *Am. Pot. J.* (1964) 41:329–336). Differences are detected in percent total solids as determined for tubers from several of the glgA transformed plants as compared to tubers from control plants.

Results are presented in Table 1 which represent average specific gravity of tubers of 5 replicate plants, except as otherwise indicated. Specific gravity measurements are determined for three to five uniformly sized tubers from each plant and the measurements of the tubers from the replicate plants are then averaged to determine average specific gravity (SpGr) of tubers for each transformation event. Values for one set of transformed control plants (Tx) and one set of untransformed/regenerated control plants (Rg) for each construct are shown at the top of their respective columns. Transformed control plants are transformed with a non-carbohydrate-related gene.

TABLE 1

Average Specific Gravity Measurements

| Event | SpGr | Event | SpGr |
|---|---|---|---|
| Controls | | Controls | |
| Tx | 1.079 | Tx | 1.083 |
| Rg | 1.081 | *Rg | 1.077 |
| Transformed Plants | | Transformed Plants | |
| 1457-3 | 1.073 | 1457B-3 | 1.062 |
| 1457-4 | 1.060 | 1457B-4 | 1.075 |
| 1457-6 | 1.076 | 1457B-5 | 1.073 |
| 1457-7 | 1.080 | 1457B-7 | 1.066 |
| 1457-8 | 1.077 | 1457B-8 | 1.066 |
| 1457-9 | 1.067 | 1457B-9 | 1.063 |
| 1457-10 | 1.083 | 1457B-10 | 1.075 |
| 1457-11 | 1.065 | 1457B-12 | 1.065 |
| 1457-12 | 1.066 | 1457B-13 | 1.058 |
| 1457-13 | 1.080 | *1457B-15 | 1.053 |
| 1457-14 | 1.062 | 1457B-16 | 1.075 |
| 1457-15 | 1.064 | 1457B-17 | 1.053 |
| 1457-16 | 1.068 | 1457B-18 | 1.068 |
| 1457-17 | 1.069 | 1457B-21 | 1.081 |
| 1457-18 | 1.060 | 1457B-22 | 1.067 |
| 1457-19 | 1.069 | 1457B-23 | 1.069 |
| 1457-20 | 1.066 | 1457B-24 | 1.068 |
| 1457-22 | 1.068 | | |

*Only 4 replicate plants are available for these samples.

It is readily apparent from the data presented in Table 1 that transgenic plants are obtained which produce tubers having an altered specific gravity as compared to the tubers from control plants.

Statistical analysis is conducted on the specific gravity measurements of tubers from the 5 replicates of one of the transformation events as compared to the - specific gravity measurements of tubers from two control events. The event analyzed is 1457-4 which has an average specific gravity of 1.060. The specific gravity measurements of tubers from the individual replicates that are used to calculate the average for this event are 1.059, 1.057, 1.067, 1.066, and 1.053. The specific gravity measurements for replicates of control tubers are as follows. Tx (ave. 1.079): 1.076, 1.082, 1.073, 1.083, and 1.079. Rg (ave. 1.081): 1.076, 1.087, 1.083, 1.082, and 1.077. These measurements are converted to percent solids as described above and the percent solids values are used for statistical analysis as follows.

A comparison of sample means is conducted on the percent solids values calculated for the three events, 1457-4, Tx and Rx, by calculating the t value (Student's t) and determining statistical difference based on a standard table of values for t. (See, for example, Steel and Torrie (1980) *Principles and Procedures of Statistics: A Biometrical Approach* (McGraw-Hill pub.) Chapter 5 and Table A.3). These analyses indicate a significant difference between the average specific gravity measurements of transgenic tubers as compared to control tubers at a confidence level of greater than 99%. The average specific gravity measurements of the two control groups are not significantly different.

Further analysis may be conducted on tubers from selected pCGN1457 and pCGN1457B transformed plants and from non-transformed controls (RB-43) to determine starch content, amylose percentages and to elucidate chain length distribution in the amylopectin component of the starch. Starch granules are isolated as described by Boyer et al. (1976) *Cereal Chemistry* 53:327–337) and starch content estimated on a weight basis (starch wt/fresh wt). Amylose percentages are determined by gel-filtration analysis (Boyer et al. (1985) Starch/Starke 37:73–79). Chain length distribution patterns are determined by HPLC analysis as described by Sanders et al. (1990) *Cereal Chemistry* 67:594–602). Amylopectins are characterized by the ratios (on a weight basis) of low molecular weight chains to high molecular weight chains as described by Hizukuri (*Carbohydrate Research* (1985) 141:295–306). Results of these analyses are presented in Table 2.

TABLE 2

Analyses of Trangenic Potato Tuber Starch

| Construct | Spec. Gravity | % Starch | % Amylose | % High M.W. Chains | % Low M.W. Chains | Low M.W./ High M.W. |
|---|---|---|---|---|---|---|
| RB-43 | 1.081 | 17.1 | 23 | 33 | 66 | 2.0 |
| 1457-4 | 1.060 | 11.0 | 12 | 20 | 80 | 4.0 |
| 1457-17 | 1.069 | 14.6 | 24 | 28 | 72 | 2.6 |
| 1457-18 | 1.060 | 11.8 | 8 | 15 | 85 | 5.7 |
| RB-43 | 1.077 | 17.2 | 27 | | | |
| 1457B-15 | 1.053 | 9.0 | 9 | 15 | 85 | 5.7 |
| 1457B-17 | 1.053 | 12.5 | 19 | 26 | 84 | 3.2 |

The data presented in Table 2 indicate that tubers, from transgenic plants which have an altered specific gravity, also have altered starch. In particular, the percentage of amylose in the transgenic potato tubers is decreased. In addition, the amylopectin portion of the starch from transgenic potato tubers has more low molecular weight chains and less high molecular weight chains than wild type potato tuber amylopectin, thus indicating that the amylopectin from transgenic tubers has more branch points.

It is evident from the above results, that plant cells and plants can be produced which have improved properties or may produce a desired product. In accordance with the subject invention, it is now seen that glycogen biosynthesis enzyme sequences may be introduced into a plant host cell and be used to express such enzyme or enzymes or to modify native starch precursors. Moreover, it is seen that such enzymes demonstrate biological activity on plant starch precursors resulting in a demonstrable phenotype in planta, namely altered specific gravity. In addition, the activity of glycogen biosynthetic enzymes in plants has been shown to result in starch having altered properties, in particular altered ratios of amylose/amylopectin and altered distribution of low molecular weight chain lengths to high molecular weight chain lengths in the amylopectin fraction. In this manner, plants, including plant cells and plant parts, having modified starch properties may be obtained, wherein the modified starch has unique and desirous properties.

In order to demonstrate the use of starch degradation product enzymes to produce CGT compounds in accordance with the present invention, the following examples demonstrate the creation of CGT structural gene constructs and the transfer of such constructs into plant expression systems.

EXAMPLE 7

Cloning the CGT Coding Region

This example describes the isolation of the coding region for a cyclodextrin glycosyltransferase (CGT) gene from *Klebsiella pneumoneae* and the engineering of the coding region for subsequent cloning.

Total genomic DNA is prepared from Klebsiella pneumoneae M5A1 (Binder et al., *Gene* (1986) 47:269–277) by growing a 5 ml culture in ECLB (Maniatis, T. et al., *Molecular Cloning: A Laboratory Manual*, Cold Spring Harbon, N.Y. (1982)) overnight at 37° C. The bacteria are pelleted by centrifugation for 10 minutes at 4500×g, the supernatant is discarded, and the pellet is resuspended in 2.5 ml of 10 mM Tris, 1 mM EDTA buffer. To this suspension is added 500 µl of a 5 mg/ml Pronase® protease (Calbiochem Brand Biochemials; La Jolla, Calif.) solution and 2 ml of 2% lauryl sulfate, sodium salt (Sigma; St. Louis, Mo.), with gentle mixing and the suspension is incubated at 37° C. for 50 minutes. A clear solution indicates that the bacteria have lysed. The solution is then extracted with 5 ml phenol, then 5 ml phenol:chloroform:isoamyl alcohol (25:24:1), followed by 5ml chloroform. Nucelic acids are precipitated from the aqueous phase with 1/10 volume of 3M sodium acetate and two volumes of 100% ethanol, and the tube is incubated at room temperature for 1 hour. Nucleic acids are removed from solution and resuspended in 1 ml water. A second ethanol precipitation is performed and the nucleic acids are resuspended in 200 µl of 10 mM Tris, 1 mM EDTA buffer.

Oligonucleotide probes flanking the 2 kb cyclodextrin glycosyltransferase (EC 2.4.1.19) gene of *K. pneumoneae* (Bender, H., *Arch. Microbiol.* (1977) 111:271–282) and containing restriction sites for BamHI and SalI are synthesized on an Applied Biosystems 380A DNA synthesizer (Foster City, Calif.) in accordance with the manufacturer's instructions. Specifically the probes are:

BamHI
str3: 5'ATATAGGATCCATTAGGACTAGATAATGAAAAGAA 3'
(SEQ ID NO:3)

SalI
str4: 5'AATAAGTCGACTTTTAATTAAAACGAGCCATTCGT 3'
(SEQ ID NO:4)

The nucleic acid preparation of *K. pneumoneae* is treated with RNAse and the DNA is used as a template in a polymerase chain reaction (PCR) with str3 and str4 as primers. A Perkin-Elmer/Cetus (Norwalk, Conn.) thermal cycler is used with the manufacturer's reagents and in accordance with the manufacturer's instructions. The reaction mixture contains 41.5 µ. H2O, 10 µl 10× Reaction buffer, 16 µl dNTP's (1.25 mM dCTP, dATP, dGTP & dTTP], 5 µl str3 (20 mM), 5 µl str4 (20 mM), 22 µl total *K. pneumoneae* DNA (0.05 µg/µl), and 0.5 µl Taq polymerase. The reaction is performed for 15 cycles with melting (denaturation) for 1 minute at 94° C., annealing (hybridization) for 2 minutes at 37° C. and chain elongation for 3 minutes at 72° C. The reaction is then performed for an additional 10 cycles with melting for 1 minute at 94° C., annealing or 2 minutes at 37° C. and chain elongation at 72° C. for 3 minutes 15 seconds initially and increasing the time by 15 seconds each cycle so that the last cycle is 5 minutes 45 seconds.

The resulting PCR product fragments (~2 kb) are digested with SalI and BamHI and ligated into a SalI and BamHI digest of pCGN65α3X (see below). Transformed *E. coli* DH5α cells (BRL; Gaithersburg, Md.) containing pCGN65α3X are screened on 1% starch plates (ECLB+1% starch) by flooding with I₂/KI and evaluating for clearing of starch from around the edge of the colony.

Clone 1 exhibited a good zone of clearing and is digested with SphI and SalI, ligated into SphI- and SalI-digested pUC19 (Norrander et al., *Gene* (1983) 26:101–106) and Yanisch-Perron et al., *Gene* (1985) 33:103–119), yielding the plasmid pCGT2 (-4.5kb). Sequence analysis of pCGT2 (FIG. 4 and SEQ ID NOS: 15) showed six single base changes randomly distributed throughout the CGT gene (99.7% homology) which resulted in three amino acid changes (FIG. 4B and SEQ ID NOS: 16, 18 and 20). Plasmid pCGT2 is digested with SphI, treated with the Klenow fragment of DNA polymerase I (Klenow fragment) to generate blunt ends and to ligate in a BglII linker. The resulting plasmid, pCGT4, is sequenced using the Sequenase® DNA sequencing kit (U.S. Biochemical; Cleveland, Ohio) in accordance with the manufacturer's instructions to confirm the correct reading frame:

```
       HindIII              BamHI
5' CCA! AGC! TTG! CG! GAT! CCG! CAG! ACG! ATT
       lac   a->           -> CGT  ->
```
(SEQ ID NO:5)

Construction of pCGN65α3X

Plasmid pUC18 (Yanisch-Perron et al., (1985) supra) is digested with HaeII to release the lacZ' fragment, treated with Klenow fragment to create blunt ends, and the lacZ'-containing fragment is ligated into pCGN565Rβ–H+X (see below), which has been digested with AccI and SphI, and treated with Klenow fragment, resulting in plasmid pCGN565RBα3X. In pCGN565RBα3X, the lac promoter is distal to the T-DNA right border. Both clones are positive for lacZ' expression when plated on an appropriate host. Each clone contains coordinates 13990-14273 of the T-DNA right border fragment (Barker et al., *Plant mol. Biol.* (1983) 2:335–350), having deleted the AccI-SphI fragment (coordinates 13800–13989). The 728 bp BglII-XhoI fragment of pCGN565RBα3X, containing the T-DNA right border piece and the lacZ' gene, is cloned into BglII- and XhoI-digested pCGN65ΔKX–S+X to replace the BglII-XhoI right border fragment of pCGN65ΔKX–S+X and create pCGN65α3X. The construction of pCGN65α3X is described in detail in co-pending U.S. application Ser. No. 07/382,176, filed Jul. 19, 1989.

Construction of pCGN565Rβ–H+X

Plasmid pCGN451 includes an octopine cassette which contains approximately 1556 bp of the 5' non-coding region fused, via an EcoRI linker, to the 3' non-coding region of the octopine synthase gene of pTiA6. The pTi coordinates are 11,207 to 12,823 for the 3' region and 13,643 to 15,208 for the 5' region (Barker et al., (1983) supra). Plasmid pCGN451 is digested with HpaI and ligated in the presence of synthetic SphI linker DNA to generate pCGN55. The XhoI-SphI fragment of pCGN55 (coordinates 13800-15208, including the right border of *Agrobacterium tumefaciens* T-DNA (Barker et al., *Gene* (1977) 2:95–113) is cloned into SalI- and SphI-digested pUC19 (Yanisch-Perron et al., (1985) supra) to create pCGN60. The 1.4kb HindIII-BamHI fragment of pCGN60 is cloned into HindIII- and BamHI-digested with pSP64 (Promega, Inc.) to generate pCGN1039. Plasmid pCGN1039 is digested with SmaI and NruI (deleting coordinates 14273–15208 (Barker et al., (1977) supra) and ligated in the presence of synthetic BglII linker DNA to create pCGN1039ΔNS. The 0.47kb EcoRI-HindIII fragment of pCGN1039ΔNS is cloned into EcoRI- and HindIII-digested pCGN565 to create pCGN565RB. The HindIII site of pCGN565RB is replaced with an XhoI site by HindIII digestion, treatment with Klenow fragment, and ligation in the presence of synthetic XhoI linker DNA to create pCGN565Rβ–H+X.

EXAMPLE 8

Plastid Translocating Sequences

This example describes the preparation of DNA sequences encoding transit peptides for use in the delivery of a CGT gene to starch-containing organelles.

Construction of SSU+aroA Transit Peptide

Plasmid pCGN1132 contains a 35S promoter-ribulosebisphosphate carboxylase small subunit (5'-35S-SSU) leader plus 48 bp of mature small subunit (SSU) protein from pea aroA sequence (the gene locus which encodes 5-enolpyruvyl-3-phosphoshikimate synthetase (EC 2.5.1.19)). It is prepared from pCGN1096, a plasmid containing a hybrid SSU protein gene, which carries DNA encoding mature SSU protein from pea, and SstI and EcoRI sites 3' of the coding region (used in the preparation of pCGN1115, a plasmid having a 5'-35S-SSU+48-aroA-tml-3' sequence, and pCGN1129, a plasmid having a 35S promoter in a chloramphenicol resistance gene (Cam$^r$) backbone).

Construction of pCGN1096

The aroA moiety of pCGN1077 is removed by digestion with SphI and SalI. In its place is cloned the region coding for the mature pea SSU protein, as an SphI-PstI fragment, which is then excised with SphI and SalI. The resulting plasmid, pCGN1094, codes for a hybrid SSU protein having the transit peptide of the soybean clone, and the mature portion of the pea clone and carrier SstI and EcoRI sites 3' of the coding region. The HindIII to BamHI region of transposon Tn6 (Jorgensen et al., *Mol. Gen. Genet.* (1979) 177:65) encoding the kanamycin resistance gene (Kan$^r$) is cloned into the same sites of pBR322 (Bolivar et al., *Gene* (1977) 2:95–133) generating pDS7. The BglII site 3' of the Kan$^r$ gene is digested and filled in with the large fragment of *E. coli* DNA polymerase 1 and deoxy-nucleotides triphosphate. An SstI linker is ligated into the blunted site, generating plasmid pCGN1093. Plasmid pPMG34.3 is digested with SalI, the site filled in as above and EcoRI linkers are ligated into the site resulting in plasmid pCGN1092. The latter plasmid is digested with SstI and SmaI and the Kan$^r$ gene excised from pCGN1093 with SstI and SmaI is ligated in, generating pCGN1095. The Kan$^r$ and aroA genes are excised as a piece from pCGN1095 by digestion with SstI and EcoRI and inserted into the SstI and EcoRI sites of pCGN1094, producing pCGN1096. Summarizing, pCGN1096 contains (5'->3') the following pertinent features: The SSU gene—a polylinker coding for PstI, SalI, SstI, and KpnI—the Kan$^r$ gene—SmaI and BamHI restriction sites—the aroA gene without the original ATG start codon. The construction of pCGN1096 is also described in detail in co-pending U.S. application Ser. No. 06/097,498, filed Sep. 16, 1987.

Plasmid pCGN1096 is digested to completion with SalI and then digested with exonuclease Bal31 (BRL; Gaithersburg, Md.) for 10 minutes, thus deleting a portion of the mature SSU gene. The resulting plasmid is then digested with SmaI to eliminate the Kan$^r$ gene and provide blunt ends, recircularized with T4 DNA ligase and transformed into *E. coli* LC3 (Comai et al., *Science* (1983) 221:370–371), an aroA mutant. DNA isolated from aroA$^+$ and Kan$^r$ colonies is digested with BamHI and SphI and ligated with BamHI$^-$ and SphI-digested M13mp18 (Norrander et al., *Gene* (1983) 26:101–106 and Yanisch-Perron et al., *Gene* (1985) 33:103–119) DNA for sequencing. Clone 7 has 48 bp of the mature SSU gene remaining (FIG. 1), and the 3' end consists of phe-glu-thr-leu-ser. Clone 7 is transformed into *E. coli* strain 71-18 (Yanisch-Perron et al. (1985) supra) and DNA isolated from transformants is digested with SphI and ClaI to remove the 0.65kb fragment containing the 48 bp of mature protein and the 5' end of the aroA gene. Plasmid pCGN1106 (Comai et al., *J. Biol. Chem.* (1988) 263:15104–15109) is also digested with SphI and ClaI and the 6.8 kb isolated vector fragment is ligated with the 0.65 kb fragment of clone 7 to yield pCGN1115 (5'-35S-SSU+48-aroA-tml-3').

The 7.2 kb plasmid pCGN1180 (35S-SSU+70-aroA-ocs3') (Comai et al. (1988) supra) and the 25.6 kb plasmid pCGN594 (Houck, et al., *Frontiers in Applied Microbiology* (1990) 4:1–17) (Lβ-Gent$^r$-ocs5'-Kan$^r$-ocs3'-RB) (construction of pCGN594 is described in co-pending U.S. application Ser. No. 07/382,802, filed Jul. 19, 1989) are digested with HindIII and ligated together to yield the 32.8 kb plasmid pCGN1109 (Lβ-Gent$^r$-35S-SSU+70-aroA-ocs3-ocs5'-Kan'r-ocs3' -RB).

Plasmid pCGN1109 is digested with EcoRI to delete an internal 9.1 kb fragment containing the SSU leader plus 70 bp of the mature SSU gene, the aroA gene and its ocs3' terminator, the Amp$^r$ backbone from pCGN1180 and ocs5I-Kan$^r$-ocs3I from pCGN594. The EcoRI digest of pCGN1109 is then treated with Klenow fragment to blunt the ends, and a XhoI linker (dCCTCGAGG) (New England Biolabs Inc.; Beverly, MA) is ligated in, yielding pCGN1125 (Lβ-35S-RB).

Plasmid pCGN1125 is digested with HindIII and BglII to delete the 0.72 kb fragment of the 35S promoter. This digest is ligated with HindIII- and BamHI-digested Cam$^r$ vector, pCGN786. Plasmid pCGN786 is a chloramphenicol resistant pUC based vector formed by insertion of a synthetic linker containing restriction digest sites EcoRI, SalI, BglII, PstI, XhoI, BamHI, and HindIII into pCGN566 (pCGN566 contains the EcoRI-HindIII linker of pUC18 inserted into the EcoKI-HindIII sites of pUC13-cm (K. Buckley (1985) Ph.D. thesis, University of California at San Diego). The resulting 3.22kb plasmid, pCGN1128, contains the 35S promoter with a 3' multilinker in a Cam$^r$ backbone.

Plasmid pCGN1128 is digested with HindIII, treated with Klenow fragment to blunt the ends and ligated with BglII linkers to yield pCGN1129, thus changing the HindIII site located 5' to the 35S promoter into a BglII site. .

Plasmid pCGN1115 is digested with SalI to removed a 1.6 kb fragment containing the SSU leader plus 48 bp of the mature SSU gene and the aroA gene. An XhoI digest of pCGN1129 opened the plasmid 3' to the 35S promoter. Ligation of these two digests yielded the 4.8 kb plasmid pCGN1132, containing 5'-35S-SSU leader plus 48 bp of mature SSU-aroA. Plasmid pCGN1132 is digested with EcoRI, treated with Klenow fragment to form blunt ends, and ligated with SacI linkers (d(CGAGCTCG) New England Biolabs Inc.; Beverly, Mass.) to yield pCGN1132S, thus changing the EcoRI site 3' to the aroA gene to a SacI site.

Transit Peptide+Cyclodextrin Glycosyltransferase Gene

Plasmid pCGT4 (See Example 7) and pCGN1132S are digested with BamHI and SalI and ligated together. The resulting plasmid pCGT5 contains 5'-35S-SSU+48-CGT-3'.

EXAMPLE 9

Cloning of Patatin Regulatory Regions and Preparation of Patatin-5'-nos-3' Expression Cassettes This example describes the cloning of patatin-5' regulatory regions from two potato varieties and the preparation of patatin-5'-nos-3' expression cassettes pCGN2143 and pCGN2144. Also provided is the cloning of patatin-3' regulatory regions and the preparation of patatin-5'-patatin-3' expression cassettes pCGN2173 and pCGN2174.

Genomic DNA is isolated from leaves of *Solanum tuberosum* var. Russett Burbank and var. Kennebec as described in Dellaporta et al., *Plant Mol. Biol. Reporter* (1983) 1(4):19–21, with the following modifications: Approximately 9 g fresh weight of leaf tissue is ground, a polytron grinding is not performed and in the final step the DNA is dissolved in 300 µl of 10 mM Tris, 1 mM EDTA, pH 8. A synthetic oligonucleotide, pat1, containing digestion sites for NheI, PstI and XhoI with 24 bp of homology of the 5'-region of a 701 bp fragment (coordinates 1611 to 2312) 5' to a class I patatin gene, isolated from *Solanum tuberosum* var. Maris Piper (Bevan et al., NAR (1986) 14:4625–4638) is synthesized (Applied BioSystems 380A DNA synthesizer): pat 1:

```
          NheI       PstI       XhoI
5' CAGCAGGCTAGCTCGCTGCAGCATCTCGAGATTTGTCAAATCAGGCTCAAAGATC 3'
(SEQ ID NO:6)
```

A second synthetic oligonucleotide, pat2, containing digestion sites for BamHI and SpeI with 25 bp of homology to the 3' region of the 701 bp piece is also synthesized: pat2:

```
        BamHI       SpeI
5' ACGACGGGATCCCATACTAGTTTTGCAAATGTTCAAATTGTTTTT 3'
(SEQ ID NO:7)
```

Using the genomic potato DNA as a template, and pat1 and pat2 as primers, a polymerase chain reaction (PCR) is performed in a Perkin-Elmer/Cetus thermal cycler with the manufacturer's reagents and in accordance with the manufacturer's instructions. The reaction contains 62.5 µH$_2$O, 10 µl 10× Reaction buffer, 16 µl dNTP's (1.25 mM dCTP, dATP, dGTP & dTTP], 5 µl pat1 (20 mM), 5 µl pat2 (20 mM), 1 µl potato genomic DNA (3 µg/µl), 0.5 µl Taq polymerase. The PCR is performed for 25 cycles with melting for 1 minute at 94° C., annealing for 2 minutes at 37° C. and chain elongation for 3 minutes at –72° C. The resulting PCR product fragments (approximately 700 bp) are digested with NheI and BamHI. Plasmid pCGN1586N (5'-D35S-TMVΩ''-nos'3'; pCGN1586 (described below) having a NheI site 5' to the 35S region) is digested with NheI and BamHI to delete the D35S-Ω' fragment. Ligation of NheI-BamHI digested pCGN1586N, which contains the nos-3' region, and the PCR fragments yield a patatin-5'-nos-3' cassette with SpeI, BamHI, SalI and SstI restriction sites between the 5' and 3' regions for insertion of a DNA sequence of interest.

The 5' regions of two clones, designated pCGN2143 and pCGN2144, are sequenced. Plasmid pCGN2143 has a Kennebec patatin-5' region that is 702 bp in length and 99.7% homologous to the native sequence (as reported by Bevan (1986) supra) (FIG. 2). The 5' region of pCGN2144, from Russet Burbank, is 636bp in length, containing a 71 bp deletion from coordinate 1971 to coordinate 2040. The remainder of the Russet Burbank clone is 97.0% homologous to the native sequence (as reported by Bevan (1986) supra) (FIG. 3).

A synthetic oligonucleotide, pat3S, with 24bp of homology to the 5' region of a 804 bp region 3' to a class I patatin gene (Bevan 5000 to 5804):
pat3S:

SstI
5' CAGCAGGAGCTCGTACAAGTTGGCGAAACATTATTG3'

(SEQ ID NO:8)

is synthesized. This oligonucleotide contained a restriction enzyme site for SstI. A second oligonucleotide, pat4, with 24 bp of homology to the 3' region of the 804 bp region is also synthesized:
pat4:

NheI          XhoI        PstI
5' ACGACGGCTAGCTCGCTCGAGCATCTGCAGTGCATATAAGTTCACATTAATATG3'
(SEQ ID NO:9)

It contains digestion sites for the enzymes NheI, XhoI and PstI.

Using Russet Burbank genomic potato DNA as a template, a polymerase chain reaction (PCR) as described above is performed for 25 cycles with melting for 1 minute at 94° C., annealing for 2 minutes at 42° C. and chain elongation for 3 minutes at 72° C. A Perkin-Elmer/Cetus thermal cycler is used with the manufacturer's reagents and in accordance with the manufacturer's instructions. Specifically, the reaction contained 53.5 µl H$_2$O, 10 µl 10× reaction buffer, 16 µl dNTP's [1.25mM dCTP, dATP, dGTP & dTTP], 5 µl pat3S (20 mM), 5 µl pat4 (20 mM), 10 µl genomic potato DNA (3 µg/µl), 0.5 µl Tag polymerase. The resulting approximately 800 bp PCR product fragments are digested with NheI and SstI and ligated into pCGN1586N (see below). Sequencing of one clone, designated pCGN2159, showed that the 3' fragment is 823 bp in length and 93.6% homologous to Bevan's reported sequence (Bevan (1986) supra).

Cloning of the patatin cassettes PCGN2173 and PCGN2174

A patatin cassette consisting of the 5' patatin region from Kennebec and 3' patatin region from Russet Burbank, identified as pCGN2173, is constructed by a three way ligation of the following fragments: The NheI to SstI Kennebec 5' patatin fragment of pCGN2143 (see above), the SstI to NheI Russet Burbank 3' patatin fragment of pCGN2159 and the NheI to NheI pUC backbone of pCGN1599.

A second patatin cassette, identified as pCGN2174, is constructed by a three way ligation of the NheI to SstI Russet Burbank 5' patatin fragment of pCGN2144 (see above), the SstI to NheI Russet Burbank 3' patatin fragment of pCGN2159 and the NheI to NheI pUC backbone of pCGN1599.

Construction of PCGN1586/1586N

Plasmid pCGN2113 (6.1 kb) contains a double-35S promoter (D35S) and the tml-3' region with multiple cloning sites between them, contained in a pUC-derived plasmid backbone bearing an ampicillin resistance gene (Amp$^r$). The promoter/tml cassette is bordered by multiple restriction sites for easy removal. Plasmid pCGN2113 is digested with EcoRI and SacI, deleting the 2.2 kb tml-3' region. Plasmid pBI221.1 (Jefferson, R. A., *Plant Mol. Biol. Reporter* (1987) 5:387–405) is digested with EcoRI and SacI to delete the 0.3 kb nos-3' region. The digested pCGN2113 and pBI221.1 DNAs are ligated together, and the resultant 4.2 kb recombinant plasmid with the tml-3' of pCGN2113 replaced by nos-3' is designated pCGN1575 (5'-D35S-nos-3').

Plasmid pCGN1575 is digested with SphI and XbaI, blunt ends generated by treatment with Klenow fragment, and the ends are ligated together. In the resulting plasmid, pCGN1577, the Sph, PstI, SalI and XbaI sites 5' of the D35S promoter are eliminated.

Plasmid pCGN1577 is digested with EcoRI, the sticky ends blunted by treatment with Klenow fragment, and synthetic BglII linkers (d(pCAGATCTG) New England Biolabs Inc.; Beverly, Mass.) are ligated in. A total of three BglII linkers are ligated into the EcoRI site creating two PstI sites. The resulting plasmid, termed pCGN1579 (D35S-nos-3'), has a 3' polylinker consisting of 5'-EcoRI, BglII, PstI, BglII, PstI, BglII, EcoRI-3'.

A tobacco Mosaic Virus omega' (TMVΩ') region (Gallie et al., NAR (1987) 15(21):8693–8711) with BglII, NcoI, BamHI, SalI and SacI restriction sites:

BglII
5' CAGGAGATCTTATTTTTACAACAATTACCAACAACAACAAACAACAAACAACATTACAAT
TACTATT TACAATTACACCATGGATCCGTCGACGAGCTC3'
           NcoI    BamHI   SalI   SacI
(SEQ ID NO: 10)

is synthesized on a Applied Biosystems® 380A DNA synthesizer and digested with BglII and SacI. Plasmid pCGN1577 is digested with BamHI and SacI and the synthetic TMVΩ' is ligated in between the 5'-D35S and nos-3' regions. The resulting plasmid is designated pCGN1586 (5'-D35S-TMVΩ'-nos'3'). Plasmid pCGN1586N is made by digesting pCGN1586 with HindIII and filling in the 5' overhang with Klenow fragment, thus forming a NheI site 5' to the D35S region.

EXAMPLE 10

Preparation of Patatin-5'-CGT-Nos-3' Binary Vectors

This example describes the construction of binary vectors containing: (1) the patatin-5' region from either *Solanum tuberosum* var. Kennebec or var. Russet Burbank, (2) DNA encoding a transit peptide from soybean RuBisCo SSU protein, (3) 48 bp of DNA encoding 16 amino acids of mature RuBisCo SSU protein from pea, (4) the CGT coding region from *Klebsiella pneumoneae*, and (5) the nos-3' region.

Plasmid pCGN2143 prepared as described in Example 9 is digested with SpeI and SstI, opening the plasmid between the patatin-5' region and nos-3' region. Plasmid pCGT5 (see Example 8) is digested with XbaI and SstI and ligated with pCGN2143 to yield pCGN2151. Plasmid pCGN2151 consists of 5'-Kennebec patatin-SSU+48-CGT-nos3'. Plasmid pCGN2151 is digested with PstI and ligated with PstI-digested pCGN1558 (see below). This yields the binary vectors pCGN2160a and pCGN2160b.

In pCGN2160a, the 5'-patatin-SSU+48bp-CGT-nos 3' is inserted into pCGN1558 such that it transcribes in the opposite direction as the 35S-Kan$^r$-tml gene. In pCGN2160b, the 5'-patatin-SSU+48bp-CGT-nos-3' is inserted into pCGN1558 such that it transcribes in the same direction as the 35S-Kan$^r$-tml gene.

Plasmid pCGN2144 is digested with SpeI and SstI, opening the plasmid between the patatin-5$^1$ and nos-3' regions. Plasmid pCGT5 is digested with XbaI and SstI and ligated with pCGN2144 to yield pCGN2152. Plasmid pCGN2152 consists of 5'-Russet Burbank patatin-SSU+48-CGT-nos3'. Plasmid pCGN2152 is digested with PstI and ligated with pCGN1558 (see below) digested with PstI. This yields the binary vectors pCGN2161a and pCGN2161b. In pCGN2161a, the 5'-patatin-SSU+48 bp-CGT-nos3' is inserted into pCGN1558 such that it transcribes in the opposite direction as the 35S-Kan$^r$-tml gene. In pCGN2161b, the 5'-patatin-SSU+48bp-CGT-nos-3' is inserted into pCGN1558 such that it transcribes in the same direction as the 35S-Kan$^r$-tml gene.

Construction of pCCGN1558

Plasmid pCGN1558 (McBride and Summerfelt, *Plant Mol. Biol.* (1990) 14(27) :269–276) is a binary plant transformation vector containing the left and right T-DNA borders of *Agrobacterium tumefaciens* octopine Ti-plasmid pTiA6 (Currier and Nester, *J. Bact.* (1976) 126:157–165), the gentamicin resistance gene (Gen$^r$) of pPH1JI (Hirsch and Beringer, *Plasmid* (1984) 12:139–141) an *Agrobacterium rhizogenes* Ri plasmid origin of replication from pLJbB11 (Jouanin et al., *Mol. Gen. Genet.* (1985) 201:370–374), a 35S promoter-Kan$^r$-tml-31 region capable of conferring kanamycin resistance to transformed plants, a ColE1 origin of replication from pBR322 (Bolivar et al. (1977) supra) and a lacZ' screenable marker gene from pUC18 (Yanish-Perron et al. (1985) supra). The construction of pCGN1558 is described in co-pending U.S. application Ser. No. 07/494, 722, filed Mar. 16, 1990.

EXAMPLE 11

Preparation of Transgenic Plants

This example describes the transformation of *Agrobacterium tumefaciens* with a CGT gene DNA construct in accordance with the present invention and the cocultivation of such *A. tumefaciens* with plant cells to transform host cells and enable the resultant plants to produce cyclodextrins.

Transformation of Agrobacterium tumefaciens

Cells of *Agrobacterium tumefaciens* strain 2760 (also known as LBA4404, Hoekema et al., *Nature* (1983) 303:179–180) are transformed with binary vectors, such as pCGN2160a, pCGN2160b, pCGN2161a and pCGN2161b (as described in Example 10) using the method of Holsters et al. (*Mol. Gen. Genet.* (1978) 163:181–187). The transformed *A. tumefaciens* are then used in the cocultivation of plants, in order to transfer the CGT construct into an expression system.

The Agrobacterium are grown in AB medium (per liter: 6 g $K_2HPO_4$, 2.3 g $NaH_2PO_4.H_2O$, 2 g $NH_4Cl$, 3 g KCl, 5 g glucose, 2.5 mg $FeSO_4$, 246 mg $MgSO_4$, 14.7 mg $CaCl_2$, 15 g agar) plus 100 µg/L gentamicin sulfate and 100 µg/L streptomycin sulfate for 4–5 days. Single colonies are inoculated into 10 ml of MG/L broth (per liter: 5 g mannitol, 1 g L-Glutamic acid or 1.15 g sodium glutamate, 0.5g $KH_2PO_4$, 0.10 g NaCl, 0.10 g $MgSO_4.0.7H_2O$, 1 µg biotin, 5 g tryptone, 2.5 g yeast extract; adjust pH to 7.0) and are incubated overnight in a shaker at 30° C. and 180 rpm. Before cocultivation, the Agrobacterium culture is centrifuged at 12,000×g for 10 minutes and resuspended in 20 ml MS medium (#510–1118, Gibco; Grand Island, N.Y.).

Cocultivation with Potato Cells

Feeder plates are prepared by pipetting 0.5 ml of a tobacco suspension culture (~$10^6$ cells/ml) onto 0.8% agar co-cultivation medium containing MS salts (#510–117, Gibco; Grand Island, N.Y.), 1.0 mg/L thiamine-HCl, 0.5 mg/L nicotinic acid, 0.5 mg/L pyridoxine-HCl, 30 g/L sucrose, 5 µM zeatin riboside, 3 µM 3-indoleacetyl-DL-aspartic acid, pH 5.9. The feeder plates are prepared one day in advance and incubated at 25OC. A sterile 3 mm filter paper disk is placed on top of the tobacco cells after they have grown for one day.

Tubers of *Solanum tuberosum* var. Russet Burbank and var. Kennebec between the age of 1 and 6 months post-harvest are peeled and washed in distilled water. All subsequent steps are carried out in a flow hood using sterile techniques. For surface sterilization, tubers are immersed in a solution of 10% commercial bleach (sodium hypochlorite) with 2 drops of Ivory® liquid soap per 100 ml for 10 minutes. Tubers are rinsed six times in sterile distilled water and kept immersed in sterile liquid MS medium (#1118, Gibco; Grand Island; N.Y.) to prevent browning.

Tuber discs (1–2mm thick) are prepared by cutting columns of potato tuber with a 1 cm cork borer and slicing the columns to the desired thickness. Discs are placed into the liquid MS medium culture of the transformed *A. tumefaciens* containing the binary vector of interest ($1 \times 10^7 - 1 \times 10^8$ bacteria/ml) until thoroughly wetted. Excess bacteria are removed by blotting discs on sterile paper towels. The discs are co-cultivated with the bacteria for 48 hours on the feeder plates and then transferred to regeneration medium (co-cultivation medium plus 500 mg/L carbenicillin and 100 mg/L kanamycin). In 3 to 4 weeks, shoots develop from the discs.

When shoots are approximately 1 cm, they are excised and transferred to a 0.8% agar rooting medium containing MS salts, 1.0 mg/L thiamine-HCl, 0.5 mg/L nicotinic acid, 0.5 mg/L pyridoxine-HCl, 30 g/L sucrose, 200 mg/L carbenicillin and 100–200 mg/L kanamycin at pH 5.9. Plants are rooted two times with at least one rooting taking place on rooting medium with the higher level of kanamycin (200 mg/L). Plants which rooted twice are then confirmed as transformed by performing the NPTII blot activity assays (Radke, S. E. et al., *Theo. Appl. Genet.* (1988) 75:685–694). Plants which are not positive for NPII activity are discarded.

Northern Blot Analysis of Transformed Plants

Total RNA is isolated from 5 g of tuber tissue (as described by Logeman et al., *Anal. Biochem.* (1987) 163:16–20). Poly-(A)+RNA is purified over oligo(dT) cellulose (as described by Maniatis et al. (1982) supra). RNA denaturing gels are run and blotted (as described by Facciotti et al., *Bio/Technology* (1985) 3:241–246). Equivalent amounts of poly-(A)+RNA are run in each lane. A 1.9 kb BamHI fragment of pCGT4 containing the CGT gene is used as a probe in the hybridization. The fragment may be isolated from an agarose gel using the Gene Clean® Kit (Bio 101, Inc.; La Jolla, Calif.) in accordance with the manufacturer's instructions. Nick-translation and hybridization are performed (as described by Shewmaker et al., *Virology* (1985) 140:281–288 except that washes are at 55° C). The washed blot is autoradiographed on Kodak® X-OMat AR X-ray film (Rochester, N.Y.) at −70° C.

An autoradiogram of Russet Burbank potatoes each transformed with one of pCGN2160a, pCGN2161a or pCGN2161b shows bands in each of the transformant sample lanes. The bands are 2.3 kb in size, corresponding to the size of CGT message RNA. There is no band present in the lane containing RNA from the untransformed control.

EXAMPLE 12

Recovery of Cyclodextrin From Plants

In this example, the recovery and detection of cyclodextrin in transgenic potato tubers is described.

Rooted plants transformed as described in Example 11 are transplanted from rooting medium to a growth chamber (21° C., 16 hour photoperiod with 250–300 µE/m²/sec light intensity) in soil prepared as follows: For about 340 gallons, combine 800 lb 20/30 sand (approximately 14 cubic feet), 16 cubic feet Fisons° Canadian Peat Moss, 16 cubic feet #3 vermiculite, and approximately 4.5 lb hydrated lime in a Gleason® mixer. The soil is steamed in the mixer for two hours; the mixer mixes for about 15 seconds at interval of fifteen minutes over a period of one hour to ensure even heating throughout the soil. During and after the process of steaming, the soil reaches temperatures of at least 180° F. for one hour. The soil then sits in the mixer until the next day. At that time, hydrated lime is added, if necessary, to adjust the pH to range between 6.30 and 6.80.

The relative humidity of the growth chamber is maintained at 70–90% for 2–4 days, after which the humidity is maintained at 40–60%. When plants are well established in the soil, at approximately two weeks, they are transplanted into the greenhouse. Plants are grown in 6.5 inch pots in a soil mix of peat:perlite:vermiculite (11:1:9) at an average temperature of 24° C. day/12° C. night. Day length is approximately 12 hours and light intensity levels varied from approximately 600 to 1000 µE/m²/sec.

Tubers are harvested from plants 14 weeks after transplant into the greenhouse. Immediately after harvest, tubers are washed, weighed and their specific gravity determined. Three representative tubers from each transformant are peeled, rinsed in distilled water, chopped into approximately 0.5 cm cubes, quick frozen in liquid nitrogen, and stored at approximately −70° C until assayed. Extraction of Cyclodextrin To prepare samples for chromatography, cubes of frozen tuber tissue are ground into a powder in a coffee mill (KrupsO, Closter, N.J.). For each plant assayed, extracts from tubers are prepared as follows: Five grams of frozen potato powder are ground in a prechilled mortar and pestle with 5 ml 25% ethanol and then frozen at −70° C for at least overnight. Samples are then centrifuged at 8500×g for 10 minutes, the supernatant transferred to a clean tube, and the ethanol removed by roto-evaporation for 1 hour.

The cyclodextrin is separated from the tissue samples in C18 SEP-PAK columns (Waters Chromatography Div.; Milford, Mass.), previously washed with 5 ml of 100% methanol, followed by 5 ml of 50% methanol, followed 5 ml of water prior to sample application. After the sample is applied, the cartridge is washed with 10 ml of distilled water to remove contaminants, and the cyclodextrins are removed with 0.75 ml of 100% methanol, discarding the first two drops. The sample is then roto-evaporated to dryness, and redissolved in 20 µl of 30% methanol. Detection of Cyclodextrin Thin layer chromatography (TLC) is performed as described by Szejtli (Szejtli, J., Cyclodextrin Technology (1988) pp. 20–22, Kluwer Academic Publishers, Boston). Samples are spotted on silicagel G plates (#01011, Analtech; Newark, Del.) and dried. The chromatogram is developed for approximately 3 hours to a height of 13–15cm, with a n-butanol-ethanol-water (4:3:3) mixture. After drying, the plate is exposed to iodine vapor for 5–10 min. to visualize the chromatogram.

Positive controls of α-cyclodextrin (α-CD) and β-cyclodextrin (β-CD) are run alongside samples from transgenic tissue, and average Rf values for four plates are 0.39 for α-CD and 0.36 for β-CD. The α-CD band stained light violet, while the β-CD band stained yellow. Tuber tissue from 20 transformed plants is screened for the presence of α-CD and β-CD. Tissue of tubers from eight Russet Burbank plants (RB2160α-11, RB2160b-7, RB2160b-9, RB2161α-2, RB2161b-3, RB2161b-5, RB2161b-11) produced bands which stained the same color as the α-CD control bands and had similar Rf values. In addition to the putative α-CD bands, the tubers from two plants . (RB2160b-7 and 2160b-9) produced bands with Rf values and color similar to the β-CD control band.

In accordance with one aspect of the subject invention, cyclodextrin can be produced by host plants by incorporation of a cyclodextrin glycosyltransferase structural gene together with the appropriate regulatory sequence. In addition, DNA sequences coding for cyclodextrin glycosyltransferase are provided which can be used for producing cyclodextrin, for example, in methods of the present invention. Thus, plants are grown which can produce cyclodextrin, in order to enhance the utility of the crop plants.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

We claim:

1. A nucleic acid construct comprising a chimeric gene which is expressed in plant cells said chimeric gene comprising a nucleotide sequence encoding a cyclodextrin glycosyltransferase enzyme operably linked with a promoter which is operable in a plant cell.

2. The construct of claim 1 wherein said nucleotide sequence is deoxyribonucleic acid.

3. The construct of claim 1 having a sequence comprising, in the 5'-3' direction of transcription, a transcription initiation region, a translational initiation region, an open reading frame sequence encoding said enzyme, and a transcription/translational termination region, wherein said regulatory regions are capable of functioning in a plant cell.

4. The construct of claim 3 wherein said transcription and translational initiation regions comprise at least a portion of the regulatory region-5' to a patatin gene from Solanum tuberosum.

5. The construct of claim 4, wherein said transcription and translational initiation regions are from Solanum tuberosum var. Kennebec.

6. The construct of claim 4, wherein said transcription and translational initiation regions are from Solanum tuberosum var. Russet Burbank.

7. The construct of claim 4, wherein said transcription and translational initiation regions are from a gene which is preferentially expressed in a potato tuber.

8. The construct of claim 3 further comprising a T-DNA border.

9. The construct of claim 1, wherein said cyclodextrin glycosyltransferase enzyme is a Klebsiella pneumoneae enzyme.

10. The construct of claim 1, further comprising a sequence coding for a marker capable of being identified and selected in a eukaryotic cell containing said sequence.

11. The construct of claim 3 further comprising: a nucleic acid sequence, bound to the 3'-end of said transcription and translational initiation region, and encoding a transit peptide joined in reading frame at the 5'-terminus of said open reading frame sequence, where the transit peptide is capable of directing transport of the expression product of said enzyme-encoding sequence, to at least one discrete location in a plant.

12. The construct of claim 11, wherein said transcription initiation region is from a gene preferentially expressed in starch-containing tissue of said plant cell.

13. The construct of claim 12, wherein said gene is a patatin gene derived from Solanum tuberosum.

14. The construct of claim 13, wherein said patatin gene is derived from a member selected from the group consisting of Solanum tuberosum var. Kennebac and Solanum tuberosum var. Russett Burbank.

15. A method to modify a starch storage organ comprising growing a plant host under conditions which permit the formation of a starch storage organ, having in its genome a nucleic acid construct which is capable of expressing a chimeric gene comprising a nucleotide sequence encoding a cyclodextrin zlycosvltransferase enzyme operably linked with a promoter, preferentially in said starch storage organ.

16. The method of claim 15 wherein the plant host is selected from the group consisting of Zea species Triticum species, Secale species, Sorghum species, Oryza species, Solanum species, Ipomoea species, Discorea species, Manihot species, Marantaceae species, Cycadaceae species, Cannaceae species, Zingiberaceae species, Palmae species and Cycadales species.

17. A method for producing reserve polysaccharide degradation products in plants which comprises:
 a) stably modifying at least one plant host cell with a nucleic acid construct comprising, in the 5'-3' direction of transcription:
  i) a transcriptional and translational initiation region functional in a plant host cell; and
  ii) a structural gene coding for a cyclodextrin gvcosvltransferase enzyme gene sequence, said sequence being under the transcriptional control of said plant host;
 and
 b) maintaining the plant host containing said construct under conditions which permit the expression of a functional cyclodextrin lycosultransferase enzyme encoded by said enzyme gene sequence.

18. The method of claim 17, wherein said transcriptional and translational initiation region comprises at least a portion of a region 5' to a patatin gene from Solanum tuberosum.

19. The method of claim 18, wherein said transcriptional and translational initiation region is from Solanum tuberosum var. Kennebec.

20. The method of claim 18, wherein said transcriptional and translational initiation region is from Solanum tuberosum var. Russet Burbank.

21. The method of claim 17, wherein said cyclodextrin glycosyltransferase enzyme is a Klebsiella pneumoneae enzyme.

22. The method of claim 17 wherein said nucleic acid construct further comprises a sequence encoding a transit peptide in reading frame at the 5'-terminus of said enzyme coding sequence, where the transit peptide is capable of directing transport of the expression product of said enzyme encoding sequence to at least one discrete location in the plant host organism.

23. The method of claim 17 wherein the plant host is selected from the group consisting of Zea species, Triticum species, Secale species, Sorghum species, Oryza species Solanum species, Ipomoea species, Discorea species, Manihot species, Marantaceae species, Cycadaceae species, Cannaceae species, Zingiberaceae species, Palmae species and Cycadales species.

24. A plant starch storage organ having a modified specific gravity produced by the method of claim 15.

25. A plant starch storage organ produced by the method of claim 15.

26. A plant host cell comprising the nucleic acid construct of claim 1 wherein said cell is capable of expressing at least one functional cyclodextrin glycosultransferase enzyme.

27. The plant host cell of claim 26, wherein said cyclodextrin glycosyltransferase enzyme is a *Klevsiella pneumoneae* enzyme.

28. The plant host cell of claim 26 wherein the plant host is selected from the group consisting of Zea species, Triticum species, Secale species, Sorghum species, Oryza species, Solanum species Ipomoea species, Discorea species, Manihot species, Marantaceae species, Cycadaceae species, Cannaceae species, Zingiberaceae species, Palmae species and Cycadales species.

29. A transformed plant comprising the nucleic acid construct of claim 1 wherein said plant is capable of producing at least one cyclodextrin as a starch degradation product.

30. The plant of claim 29 wherein said cyclodextrin comprises at least one member selected from the group consisting of $\alpha$-cyclodextrins, $\beta$-cyclodextrins and $\gamma$-cyclodextrins.

31. The plant of claim 30 wherein the plant is selected from the group consisting of Zea species, Triticum species, Secale species, Sorghum species, Oryza species, Solanum species, Ipomoea species Discorea species, Manihot species, Marantaceae species, Cycadaceae species, Cannaceae species, Zingiberaceae species, Palmae species and Cycadales species.

32. The construct of claim 9, wherein said nucleotide sequence is a plant preferred coding sequence.

33. The method of claim 21, wherein said nucleotide sequence is a plant-preferred coding sequence.

34. The plant host cell of claim 27, wherein said nucleotide sequence is a plant-preferred coding sequence.

35. The method of claim 16 wherein the plant host is selected from the group consisting of *Zea mays, Secale cereale, Sorghum bicolor, Oryza sativa, Solanum tuberosum, Ipomoea batatas,* and *Manihot esculenta.*

36. The method of claim 15, wherein the plant host is a *Triticum aestivum×Secale cereale* hybrid.

37. The method of claim 23 wherein the plant host is selected from the group consisting of *Zea mays, Secale cereale, Sorghum bicolor, Oryza sativa, Solanum tuberosum, Ipomoea batatas,* and *Manihot esculenta.*

38. The method of claim 17, wherein the plant host is a *Triticum aestivum×Secale cereale* hybrid.

39. The plant host cell of claim 28, wherein the plant host is selected from the group consisting of *Zea mays, Secale cereale, Sorghum bicolor, Oryza sativa, Solanum tuberosum, Ipomoea batatas,* and *Manihot esculenta.*

40. The plant host cell of claim 26, wherein the plant host is a *Triticum aestivum×Secale cereale* hybrid.

41. The plant of claim wherein the plant is selected from the group consisting of *Zea mays, Secale cereale, Sorghum bicolor, Oryza sativa, Solanum tuberosum, Ipomoea batatas,* and *Manihot esculenta.*

42. The plant of claim 30, wherein the plant is a *Triticum aestivum×Secale cereale* hybrid.

\* \* \* \* \*

UNITED STATES PATENT AND TRADEMARK OFFICE
CERTIFICATE OF CORRECTION

PATENT NO. : 5,750,875
DATED : May 12, 1998
INVENTOR(S) : Stalker et al.

It is certified that error appears in the above-identified patent and that said Letters Patent is hereby corrected as shown below:

On the title page, Column 2, "Bell Seltzer Intellectual Property Group" should read --BELL SELTZER Intellectual Property Law Group of ALSTON & BIRD LLP--.

Column 72, line 22, "zlycosvltransferase" should read --glycosyltransferase--.

Column 72, lines 38 - 39, "gvcosvltransferase" should read --glycosyltransferase--.

Column 72, line 45, "lycosultransferase" should read --glycosyltransferase--.

Column 73, line 11, "glycosultransferase" should read --glycosyltransferase--.

Column 73, line 13, "Klevsiella" should read --Klebsiella--.

Signed and Sealed this

Twenty-seventh Day of April, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO:1:

```
Phe  Glu  Thr  Leu  Ser
 1                    5
```

( 2 ) INFORMATION FOR SEQ ID NO:2:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:2:

```
CAGGAGATCT TATTTTTACA ACAATTACCA ACAACAACAA ACAACAAACA ACATTACAAT        60
TACTATTTAC AATTACACCA TGGATCCGTC GACGAGCTC                               99
```

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:3:

```
ATATAGGATC CATTAGGACT AGATAATGAA AAGAA                                   35
```

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:4:

```
AATAAGTCGA CTTTTAATTA AAACGAGCCA TTCGT                                   35
```

( 2 ) INFORMATION FOR SEQ ID NO:5:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( x i ) SEQUENCE DESCRIPTION: SEQ ID NO:5:

CCAAGCTTGC GGATCCGCAG ACGATT                                                          26

( 2 ) INFORMATION FOR SEQ ID NO:6:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:6:

CAGCAGGCTA GCTCGCTGCA GCATCTCGAG ATTTGTCAAA TCAGGCTCAA AGATC       55

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:7:

ACGACGGGAT CCCATACTAG TTTTGCAAAT GTTCAAATTG TTTTT                   45

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:8:

CAGCAGGAGC TCGTACAAGT TGGCGAAACA TTATTG                                   36

( 2 ) INFORMATION FOR SEQ ID NO:9:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:9:

ACGACGGCTA GCTCGCTCGA GCATCTGCAG TGCATATAAG TTCACATTAA TATG    54

( 2 ) INFORMATION FOR SEQ ID NO:10:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:10:

CAGGAGATCT TATTTTTACA ACAATTACCA ACAACAACAA ACAACAAACA ACATTACAAT    60

TACTATTTAC AATTACACCA TGGATCCGTC GACGAGCTC    99

( 2 ) INFORMATION FOR SEQ ID NO:11:

( i ) SEQUENCE CHARACTERISTICS:
        ( A ) LENGTH: 1464 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:11:

GATCTAACAG GAGCGATAAT GCAGGTTTTA CATGTATGTT CAGAGATGTT CCCGCTGCTT    60

AAAACCGGCG GTCTGGCTGA TGTTATTGGG GCATTACCCG CAGCACAAAT CGCAGACGGC    120

GTTGACGCTC GCGTACTGTT GCCTGCATTT CCCGATATTC GCCGTGGCGT GACCGATGCG    180

CAGGTAGTAT CCCGTCGTGA TACCTTCGCC GGACATATCA CGCTGTTGTT CGGTCATTAC    240

AACGGGGTTG GCATTTACCT GATTGACGCG CCGCATCTCT ATGATCGTCC GGGAAGCCCG    300

TATCACGATA CCAACTTATT TGCCTATACC GACAACGTAT GCGTTTTGC GCTGCTGGGG    360

TGGGTTGGGG CAGAAATGGC CAGCGGGCTT GACCCATTCT GGCGTCCTGA TGTGGTGCAT    420

GCGCACGACT GGCATGCAGG CCTTGCGCCT GCGTATCTGG CGGCGCGCGG GCGTCCGGCG    480

AAGTCGGTGT TTACTGGGCA CAACCTGGCC TATCAAGGCA TGTTTTATGC ACATCACATG    540

AATGACATCC AATTGCCATG GTCATTCTTT AATATTCATG GGCTGGAATT CAACGGACAA    600

ATCTCTTTCC TGAAGGCCGG TCTGTACTAT GCCGATCACA TTACGGCGGT CAGTCCAACC    660

TACGCTCGCG AGATCACCGA ACCGCAGTTT GCCTACGGTA TGGAAGGTCT GTTGCAACAG    720

CGTCACCGTG AAGGGCGTCT TTCCGGCGTA CTGAACGGCG TGGACGAGAA AATCTGGAGT    780

CCAGAGACGG ACTTACTGTT GGCCTCGCGT TACACCCGCG ATACGTTGGA AGATAAAGCG    840

GAAAATAAGC GCCAGTTACA AATCGCAATG GGGCTTAAGG TTGACGATAA AGTGCCGCTT    900

TTTGCAGTGG TGAGCCGTCT GACCAGCCAG AAAGGTCTCG ACCTGGTGCT GGAAGCCTTA    960

CCGGGTCTTC TGGAGCAGGG CGGGCAGCTG GCGCTACTCG GCGCGGGCGA TCCGGTGCTG    1020

CAGGAAGGTT TCCTTGCGGC GGCAGCGGAA TACCCCGGTC AGGTGGGCGT TCAGATTGGC    1080

TATCACGAAG CATTTTCGCA TCGCATTATG GGCGGCGCGG ACGTCATTCT GGTGCCCAGC    1140

CGTTTTGAAC CGTGCGGCTT AACGCAACTT TATGGATTGA AGTACGGTAC GCTGCCGTTA    1200

GTGCGGCGCA CCGGTGGGCT TGCTGATACG GTTTCTGACT GTTCTCTTGA GAACCTTGCA    1260

GATGGCGTCG CCAGTGGGTT TGTCTTTGAA GATAGTAATG CCTGGTCGCT GTTACGGGCT    1320

```
ATTCGACGTG CTTTTGTACT GTGGTCCCGT CCTTCACTGT GGCGGTTTGT GCAACGTCAG    1380

GCTATGGCAA TGGATTTTAG CTGGCAGGTC GCGGCGAAGT CGTACCGTGA GCTTTACTAT    1440

CGCTCGAAAT AGTTTTCAGT CGAC                                           1464
```

(2) INFORMATION FOR SEQ ID NO:12:

(i) SEQUENCE CHARACTERISTICS:
        (A) LENGTH: 477 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:12:

```
Met Gln Val Leu His Val Cys Ser Glu Met Phe Pro Leu Leu Lys Thr
  1               5                  10                  15

Gly Gly Leu Ala Asp Val Ile Gly Ala Leu Pro Ala Ala Gln Ile Ala
                 20                  25                  30

Asp Gly Val Asp Ala Arg Val Leu Leu Pro Ala Phe Pro Asp Ile Arg
             35                  40                  45

Arg Gly Val Thr Asp Ala Gln Val Val Ser Arg Arg Asp Thr Phe Ala
         50                  55                  60

Gly His Ile Thr Leu Leu Phe Gly His Tyr Asn Gly Val Gly Ile Tyr
 65                  70                  75                  80

Leu Ile Asp Ala Pro His Leu Tyr Asp Arg Pro Gly Ser Pro Tyr His
                 85                  90                  95

Asp Thr Asn Leu Phe Ala Tyr Thr Asp Asn Val Leu Arg Phe Ala Leu
                100                 105                 110

Leu Gly Trp Val Gly Ala Glu Met Ala Ser Gly Leu Asp Pro Phe Trp
            115                 120                 125

Arg Pro Asp Val Val His Ala His Asp Trp His Ala Gly Leu Ala Pro
        130                 135                 140

Ala Tyr Leu Ala Ala Arg Gly Arg Pro Ala Lys Ser Val Phe Thr Gly
145                 150                 155                 160

His Asn Leu Ala Tyr Gln Gly Met Phe Tyr Ala His His Met Asn Asp
                165                 170                 175

Ile Gln Leu Pro Trp Ser Phe Phe Asn Ile His Gly Leu Glu Phe Asn
                180                 185                 190

Gly Gln Ile Ser Phe Leu Lys Ala Gly Leu Tyr Tyr Ala Asp His Ile
            195                 200                 205

Thr Ala Val Ser Pro Thr Tyr Ala Arg Glu Ile Thr Glu Pro Gln Phe
        210                 215                 220

Ala Tyr Gly Met Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
                245                 250                 255

Thr Asp Leu Leu Leu Ala Ser Arg Tyr Thr Arg Asp Thr Leu Glu Asp
            260                 265                 270

Lys Ala Glu Asn Lys Arg Gln Leu Gln Ile Ala Met Gly Leu Lys Val
        275                 280                 285

Asp Asp Lys Val Pro Leu Phe Ala Val Val Ser Arg Leu Thr Ser Gln
290                 295                 300

Lys Gly Leu Asp Leu Val Leu Glu Ala Leu Pro Gly Leu Leu Glu Gln
305                 310                 315                 320
```

```
            Gly  Gly  Gln  Leu  Ala  Leu  Leu  Gly  Ala  Gly  Asp  Pro  Val  Leu  Gln  Glu
                           325                     330                     335

Gly  Phe  Leu  Ala  Ala  Ala  Ala  Glu  Tyr  Pro  Gly  Gln  Val  Gly  Val  Gln
                           340                     345                     350

Ile  Gly  Tyr  His  Glu  Ala  Phe  Ser  His  Arg  Ile  Met  Gly  Gly  Ala  Asp
                           355                     360                     365

Val  Ile  Leu  Val  Pro  Ser  Arg  Phe  Glu  Pro  Cys  Gly  Leu  Thr  Gln  Leu
                           370                     375                     380

Tyr  Gly  Leu  Lys  Tyr  Gly  Thr  Leu  Pro  Leu  Val  Arg  Arg  Thr  Gly  Gly
            385                      390                     395                          400

Leu  Ala  Asp  Thr  Val  Ser  Asp  Cys  Ser  Leu  Glu  Asn  Leu  Ala  Asp  Gly
                                405                     410                     415

Val  Ala  Ser  Gly  Phe  Val  Phe  Glu  Asp  Ser  Asn  Ala  Trp  Ser  Leu  Leu
                           420                     425                     430

Arg  Ala  Ile  Arg  Arg  Ala  Phe  Val  Leu  Trp  Ser  Arg  Pro  Ser  Leu  Trp
                           435                     440                     445

Arg  Phe  Val  Gln  Arg  Gln  Ala  Met  Ala  Met  Asp  Phe  Ser  Trp  Gln  Val
                      450                     455                     460

Ala  Ala  Lys  Ser  Tyr  Arg  Glu  Leu  Tyr  Tyr  Arg  Ser  Lys
            465                      470                     475
```

(2) INFORMATION FOR SEQ ID NO:13:

(i) SEQUENCE CHARACTERISTICS:
    (A) LENGTH: 1323 base pairs
    (B) TYPE: nucleic acid
    (C) STRANDEDNESS: single
    (D) TOPOLOGY: circular (ii) MOLECULE TYPE: DNA (genomic)

(iii) HYPOTHETICAL: NO (xi) SEQUENCE DESCRIPTION: SEQ ID NO:13:

```
GATCTAGGAG CGATA ATG GTT AGT TTA GAG AAG AAC GAT CAC TTA ATG TTG           51
                 Met Val Ser Leu Glu Lys Asn Asp His Leu Met Leu
                  1               5                  10

GCG CGC CAG CTG CCA TTG AAA TCT GTT GCC CTG ATA CTG GCG GGA GGA            99
Ala Arg Gln Leu Pro Leu Lys Ser Val Ala Leu Ile Leu Ala Gly Gly
             15                  20                  25

CGT GGT ACC CGC CTG AAG GAT TTA ACC AAT AAG CGA GCA AAA CCG GCC           147
Arg Gly Thr Arg Leu Lys Asp Leu Thr Asn Lys Arg Ala Lys Pro Ala
         30                  35                  40

GTA CAC TTC GGC GGT AAG TTC CGC ATT ATC GAC TTT GCG CTG TCT AAC           195
Val His Phe Gly Gly Lys Phe Arg Ile Ile Asp Phe Ala Leu Ser Asn
45                  50                  55                  60

TGC ATC AAC TCC GGG ATC CGT CGT ATG GGC GTG ATC ACC CAG TAC CAG           243
Cys Ile Asn Ser Gly Ile Arg Arg Met Gly Val Ile Thr Gln Tyr Gln
                 65                  70                  75

TCC CAC ACT CTG GTG CAG CAC ATT CAG CGC GGC TGG TCA TTC TTC AAT           291
Ser His Thr Leu Val Gln His Ile Gln Arg Gly Trp Ser Phe Phe Asn
             80                  85                  90

GAA GAA ATG AAC GAG TTT GTC GAT CTG CTG CCA GCA CAG CAG AGA ATG           339
Glu Glu Met Asn Glu Phe Val Asp Leu Leu Pro Ala Gln Gln Arg Met
         95                 100                 105

AAA GGG GAA AAC TGG TAT CGC GGC ACC GCA GAT GCG GTC ACC CAA AAC           387
Lys Gly Glu Asn Trp Tyr Arg Gly Thr Ala Asp Ala Val Thr Gln Asn
110                 115                 120

CTC GAC ATT ATC CGC CGT TAT AAA GCG GAA TAC GTG GTG ATC CTG GCG           435
Leu Asp Ile Ile Arg Arg Tyr Lys Ala Glu Tyr Val Val Ile Leu Ala
```

|  |  |  |  |  |  |  |  |  |  |  |  |  |  |  |  |
|---|---|---|---|---|---|---|---|---|---|---|---|---|---|---|---|
| 125 |  |  |  |  | 130 |  |  |  |  | 135 |  |  |  |  | 140 |

```
GGC  GAC  CAT  ATC  TAC  AAG  CAA  GAC  TAC  TCG  CGT  ATG  CTT  ATC  GAT  CAC        483
Gly  Asp  His  Ile  Tyr  Lys  Gln  Asp  Tyr  Ser  Arg  Met  Leu  Ile  Asp  His
                    145                     150                     155

GTC  GAA  AAA  GGC  GCA  CGT  TGC  ACC  GTT  GCT  TGT  ATG  CCA  GTA  CCG  ATT        531
Val  Glu  Lys  Gly  Ala  Arg  Cys  Thr  Val  Ala  Cys  Met  Pro  Val  Pro  Ile
               160                     165                     170

GAA  GAA  GCC  TCC  GCA  TTT  GGC  GTT  ATG  GCG  GTT  GAT  GAG  AAC  GAT  AAA        579
Glu  Glu  Ala  Ser  Ala  Phe  Gly  Val  Met  Ala  Val  Asp  Glu  Asn  Asp  Lys
          175                     180                     185

ATT  ATC  GAA  TTC  GTT  GAA  AAA  CCT  GCT  AAC  CCG  CCG  TCA  ATG  CCG  AAC        627
Ile  Ile  Glu  Phe  Val  Glu  Lys  Pro  Ala  Asn  Pro  Pro  Ser  Met  Pro  Asn
     190                     195                     200

GAT  CCG  AGC  AAA  TCT  CTG  GCG  AGT  ATG  GGT  ATC  TAC  GTC  TTT  GAC  GCC        675
Asp  Pro  Ser  Lys  Ser  Leu  Ala  Ser  Met  Gly  Ile  Tyr  Val  Phe  Asp  Ala
205                     210                     215                     220

GAC  TAT  CTG  TAT  GAA  CTG  CTG  GAA  GAA  GAC  GAT  CGC  GAT  GAG  AAC  TCC        723
Asp  Tyr  Leu  Tyr  Glu  Leu  Leu  Glu  Glu  Asp  Asp  Arg  Asp  Glu  Asn  Ser
                    225                     230                     235

AGC  CAC  GAC  TTT  GGC  AAA  GAT  TTG  ATT  CCC  AAG  ATC  ACC  GAA  GCC  GGT        771
Ser  His  Asp  Phe  Gly  Lys  Asp  Leu  Ile  Pro  Lys  Ile  Thr  Glu  Ala  Gly
               240                     245                     250

CTG  GCC  TAT  GCG  CAC  CCG  TTC  CCG  CTC  TCT  TGC  GTA  CAA  TCC  GAC  CCG        819
Leu  Ala  Tyr  Ala  His  Pro  Phe  Pro  Leu  Ser  Cys  Val  Gln  Ser  Asp  Pro
          255                     260                     265

GAT  GCC  GAG  CCG  TAC  TGG  CGC  GAT  GTG  GGT  ACG  CTG  GAA  GCT  TAC  TGG        867
Asp  Ala  Glu  Pro  Tyr  Trp  Arg  Asp  Val  Gly  Thr  Leu  Glu  Ala  Tyr  Trp
     270                     275                     280

AAA  GCG  AAC  CTC  GAT  CTG  GCC  TCT  GTG  GTG  CCG  GAA  CTG  GAT  ATG  TAC        915
Lys  Ala  Asn  Leu  Asp  Leu  Ala  Ser  Val  Val  Pro  Glu  Leu  Asp  Met  Tyr
285                     290                     295                     300

GAT  CGC  AAT  TGG  CCA  ATT  CGC  ACC  TAC  AAT  GAA  TCA  TTA  CCG  CCA  GCG        963
Asp  Arg  Asn  Trp  Pro  Ile  Arg  Thr  Tyr  Asn  Glu  Ser  Leu  Pro  Pro  Ala
                    305                     310                     315

AAA  TTC  GTG  CAG  GAT  CGC  TCC  GGT  AGC  CAC  GGG  ATG  ACC  CTT  AAC  TCA       1011
Lys  Phe  Val  Gln  Asp  Arg  Ser  Gly  Ser  His  Gly  Met  Thr  Leu  Asn  Ser
               320                     325                     330

CTG  GTT  TCC  GAC  GGT  TGT  GTG  ATC  TCC  GGT  TCG  GTG  GTG  GTG  CAG  TCC       1059
Leu  Val  Ser  Asp  Gly  Cys  Val  Ile  Ser  Gly  Ser  Val  Val  Val  Gln  Ser
          335                     340                     345

GTT  CTG  TTC  TCG  CGC  GTT  CGC  GTG  AAT  TCA  TTC  TGC  GAC  ATT  GAT  TCC       1107
Val  Leu  Phe  Ser  Arg  Val  Arg  Val  Asn  Ser  Phe  Cys  Asp  Ile  Asp  Ser
     350                     355                          360

GCC  GTA  TTG  TTA  CCG  GAA  GTA  TGG  GTA  GGT  CGC  TCG  TGC  CGT  CTG  CGC       1155
Ala  Val  Leu  Leu  Pro  Glu  Val  Trp  Val  Gly  Arg  Ser  Cys  Arg  Leu  Arg
365                     370                     375                     380

CGC  TGC  GTC  ATC  GAT  CGT  GCT  TGT  GTT  ATT  CCG  GAA  GGC  ATG  GTG  ATT       1203
Arg  Cys  Val  Ile  Asp  Arg  Ala  Cys  Val  Ile  Pro  Glu  Gly  Met  Val  Ile
                    385                     390                     395

GGT  GAA  AAC  GCA  GAG  GAA  GAT  GCA  CGT  CGT  TTC  TAT  CGT  TCA  GAA  GAA       1251
Gly  Glu  Asn  Ala  Glu  Glu  Asp  Ala  Arg  Arg  Phe  Tyr  Arg  Ser  Glu  Glu
               400                     405                     410

GGC  ATC  GTG  CTG  GTA  ACG  CGC  GAA  ATG  CTA  CGG  AAG  TTA  GGG  CAT  AAA       1299
Gly  Ile  Val  Leu  Val  Thr  Arg  Glu  Met  Leu  Arg  Lys  Leu  Gly  His  Lys
          415                     420                     425

CAG  GAG  CGA  TAATGCAGGG  TCGAC                                                     1323
Gln  Glu  Arg
430
```

( 2 ) INFORMATION FOR SEQ ID NO:14:

( i ) SEQUENCE CHARACTERISTICS:
  ( A ) LENGTH: 431 amino acids
  ( B ) TYPE: amino acid
  ( D ) TOPOLOGY: linear ( i i ) MOLECULE TYPE: protein ( x i ) SEQUENCE DESCRIPTION: SEQ ID NO:14:

```
Met Val Ser Leu Glu Lys Asn Asp His Leu Met Leu Ala Arg Gln Leu
 1               5                  10                  15

Pro Leu Lys Ser Val Ala Leu Ile Leu Ala Gly Gly Arg Gly Thr Arg
            20                  25                  30

Leu Lys Asp Leu Thr Asn Lys Arg Ala Lys Pro Ala Val His Phe Gly
        35                  40                  45

Gly Lys Phe Arg Ile Ile Asp Phe Ala Leu Ser Asn Cys Ile Asn Ser
    50                  55                  60

Gly Ile Arg Arg Met Gly Val Ile Thr Gln Tyr Gln Ser His Thr Leu
65                  70                  75                  80

Val Gln His Ile Gln Arg Gly Trp Ser Phe Phe Asn Glu Glu Met Asn
                85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Val Ile Leu Ala Gly Asp His Ile
    130                 135                 140

Tyr Lys Gln Asp Tyr Ser Arg Met Leu Ile Asp His Val Glu Lys Gly
145                 150                 155                 160

Ala Arg Cys Thr Val Ala Cys Met Pro Val Pro Ile Glu Glu Ala Ser
                165                 170                 175

Ala Phe Gly Val Met Ala Val Asp Glu Asn Asp Lys Ile Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
    210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Pro Glu Leu Asp Met Tyr Asp Arg Asn Trp
    290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Asp
                325                 330                 335

Gly Cys Val Ile Ser Gly Ser Val Val Gln Ser Val Leu Phe Ser
            340                 345                 350

Arg Val Arg Val Asn Ser Phe Cys Asp Ile Asp Ser Ala Val Leu Leu
        355                 360                 365

Pro Glu Val Trp Val Gly Arg Ser Cys Arg Leu Arg Arg Cys Val Ile
```

```
           370                        375                        380
Asp  Arg  Ala  Cys  Val  Ile  Pro  Glu  Gly  Met  Val  Ile  Gly  Glu  Asn  Ala
385                      390                       395                      400

Glu  Glu  Asp  Ala  Arg  Arg  Phe  Tyr  Arg  Ser  Glu  Glu  Gly  Ile  Val  Leu
                    405                       410                      415

Val  Thr  Arg  Glu  Met  Leu  Arg  Lys  Leu  Gly  His  Lys  Gln  Glu  Arg
               420                       425                      430
```

( 2 ) INFORMATION FOR SEQ ID NO:15:

( i ) SEQUENCE CHARACTERISTICS:
        ( A ) LENGTH: 281 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:15:

```
TCT  AGA  AGC  TTG  GAT  ATC  TGG  CAG  CAG  AAA  AAC  AAG  TAG  TTG  AGA  ACT    48
Ser  Arg  Ser  Leu  Asp  Ile  Trp  Gln  Gln  Lys  Asn  Lys       Leu  Arg  Thr
 1                   5                        10                           15

AAG  AAG  AAG  AAA  ATG  GCT  TCC  TCA  ATG  ATC  TCC  TCC  CCA  GCT  GTT  ACC    96
Lys  Lys  Lys  Lys  Met  Ala  Ser  Ser  Met  Ile  Ser  Ser  Pro  Ala  Val  Thr
                20                        25                            30

ACC  GTC  AAC  CGT  GCC  GGT  GCC  GGC  ATG  GTT  GCT  CCA  TTC  ACC  GGC  CTC   144
Thr  Val  Asn  Arg  Ala  Gly  Ala  Gly  Met  Val  Ala  Pro  Phe  Thr  Gly  Leu
                 35                       40                       45

AAA  TCC  ATG  GCT  GGC  TTC  CCC  ACG  AGG  AAG  ACC  AAC  AAT  GAC  ATT  ACC   192
Lys  Ser  Met  Ala  Gly  Phe  Pro  Thr  Arg  Lys  Thr  Asn  Asn  Asp  Ile  Thr
           50                        55                        60

TCC  ATT  GCT  AGC  AAC  GGT  GGA  AGA  GTA  CAA  TGC  ATG  CAG  GTG  TGG  CCT   240
Ser  Ile  Ala  Ser  Asn  Gly  Gly  Arg  Val  Gln  Cys  Met  Gln  Val  Trp  Pro
      65                        70                       75

CCA  ATT  GGA  AAG  AAG  AAG  TTT  GAG  ACT  CTT  TCC  TGG  GAT  CC              281
Pro  Ile  Gly  Lys  Lys  Lys  Phe  Glu  Thr  Leu  Ser  Trp  Asp
 80                       85                       90
```

( 2 ) INFORMATION FOR SEQ ID NO:16:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ser  Arg  Ser  Leu  Asp  Ile  Trp  Gln  Gln  Lys  Asn  Lys  Leu  Arg  Thr  Lys
 1                   5                        10                           15

Lys  Lys  Lys  Met  Ala  Ser  Ser  Met  Ile  Ser  Ser  Pro  Ala  Val  Thr  Thr
                20                        25                            30

Val  Asn  Arg  Ala  Gly  Ala  Gly  Met  Val  Ala  Pro  Phe  Thr  Gly  Leu  Lys
                 35                       40                       45

Ser  Met  Ala  Gly  Phe  Pro  Thr  Arg  Lys  Thr  Asn  Asn  Asp  Ile  Thr  Ser
      50                        55                        60

Ile  Ala  Ser  Asn  Gly  Gly  Arg  Val  Gln  Cys  Met  Gln  Val  Trp  Pro  Pro
 65                       70                       75                      80

Ile  Gly  Lys  Lys  Lys  Phe  Glu  Thr  Leu  Ser  Trp  Asp
                85                       90
```

( 2 ) INFORMATION FOR SEQ ID NO:17:

( i ) SEQUENCE CHARACTERISTICS:
        ( A ) LENGTH: 281 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:17:

```
T CTA GAA GCT TGG ATA TCT GGC AGC AGA AAA ACA AGT AGT TGA GAA           46
  Leu Glu Ala Trp Ile Ser Gly Ser Arg Lys Thr Ser Ser     Glu
  1               5                   10

CTA AGA AGA AGA AAA TGG CTT CCT CAA TGA TCT CCT CCC CAG CTG TTA         94
Leu Arg Arg Arg Lys Trp Leu Pro Gln     Ser Pro Pro Gln Leu Leu
15              20                      25

CCA CCG TCA ACC GTG CCG GTG CCG GCA TGG TTG CTC CAT TCA CCG GCC         142
Pro Pro Ser Thr Val Pro Val Pro Ala Trp Leu Leu His Ser Pro Ala
30              35                  40                      45

TCA AAT CCA TGG CTG GCT TCC CCA CGA GGA AGA CCA ACA ATG ACA TTA         190
Ser Asn Pro Trp Leu Ala Ser Pro Arg Gly Arg Pro Thr Met Thr Leu
                50                  55                      60

CCT CCA TTG CTA GCA ACG GTG GAA GAG TAC AAT GCA TGC AGG TGT GGC         238
Pro Pro Leu Leu Ala Thr Val Glu Glu Tyr Asn Ala Cys Arg Cys Gly
            65                  70                  75

CTC CAA TTG GAA AGA AGA AGT TTG AGA CTC TTT CCT GGG ATC                 280
Leu Gln Leu Glu Arg Arg Ser Leu Arg Leu Phe Pro Gly Ile
        80                  85                  90

C                                                                       281
```

( 2 ) INFORMATION FOR SEQ ID NO:18:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Leu Glu Ala Trp Ile Ser Gly Ser Arg Lys Thr Ser Ser Glu Leu Arg
1               5                   10                  15

Arg Arg Lys Trp Leu Pro Gln Ser Pro Gln Leu Leu Pro Ser
            20                  25                  30

Thr Val Pro Val Pro Ala Trp Leu Leu His Ser Pro Ala Ser Asn Pro
            35                  40                  45

Trp Leu Ala Ser Pro Arg Gly Arg Pro Thr Met Thr Leu Pro Pro Leu
        50                  55                  60

Leu Ala Thr Val Glu Glu Tyr Asn Ala Cys Arg Cys Gly Leu Gln Leu
65                  70                  75                  80

Glu Arg Arg Ser Leu Arg Leu Phe Pro Gly Ile
            85                  90
```

( 2 ) INFORMATION FOR SEQ ID NO:19:

( i ) SEQUENCE CHARACTERISTICS:
        ( A ) LENGTH: 281 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( x i ) SEQUENCE DESCRIPTION: SEQ ID NO:19:

```
TCTAG AAG CTT GGA TAT CTG GCA GCA GAA AAA CAA GTA GTT GAG AAC      47
      Lys Leu Gly Tyr Leu Ala Ala Glu Lys Gln Val Val Glu Asn
        1           5                  10

TAA GAA GAA GAA AAT GGC TTC CTC AAT GAT CTC CTC CCC AGC TGT TAC    95
    Glu Glu Glu Asn Gly Phe Leu Asn Asp Leu Leu Pro Ser Cys Tyr
     15                  20                  25

CAC CGT CAA CCG TGC CGG TGC CGG CAT GGT TGC TCC ATT CAC CGG CCT   143
His Arg Gln Pro Cys Arg Cys Arg His Gly Cys Ser Ile His Arg Pro
 30                  35                  40                  45

CAA ATC CAT GGC TGG CTT CCC CAC GAG GAA GAC CAA CAA TGA CAT TAC   191
Gln Ile His Gly Trp Leu Pro His Glu Glu Asp Gln Gln     His Tyr
                 50                  55                      60

CTC CAT TGC TAG CAA CGG TGG AAG AGT ACA ATG CAT GCA GGT GTG GCC   239
Leu His Cys     Gln Arg Trp Lys Ser Thr Met His Ala Gly Val Ala
                     65                  70                  75

TCC AAT TGG AAA GAA GAA GTT TGA GAC TCT TTC CTG GGA TCC           281
Ser Asn Trp Lys Glu Glu Val     Asp Ser Phe Leu Gly Ser
                 80                      85
```

( 2 ) INFORMATION FOR SEQ ID NO:20:

( i ) SEQUENCE CHARACTERISTICS:
( A ) LENGTH: 88 amino acids
( B ) TYPE: amino acid
( D ) TOPOLOGY: linear ( i i ) MOLECULE TYPE: protein ( x i ) SEQUENCE DESCRIPTION: SEQ ID NO:20:

```
Lys Leu Gly Tyr Leu Ala Ala Glu Lys Gln Val Val Glu Asn Glu Glu
 1               5                  10                  15

Glu Asn Gly Phe Leu Asn Asp Leu Leu Pro Ser Cys Tyr His Arg Gln
                 20                  25                  30

Pro Cys Arg Cys Arg His Gly Cys Ser Ile His Arg Pro Gln Ile His
             35                  40                  45

Gly Trp Leu Pro His Glu Glu Asp Gln Gln His Tyr Leu His Cys Gln
 50                  55                  60

Arg Trp Lys Ser Thr Met His Ala Gly Val Ala Ser Asn Trp Lys Glu
 65                  70                  75                  80

Glu Val Asp Ser Phe Leu Gly Ser
                 85
```

( 2 ) INFORMATION FOR SEQ ID NO:21:

( i ) SEQUENCE CHARACTERISTICS:
( A ) LENGTH: 718 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:21:

```
CTCGAGATTT GTCAAATCAG GCTCAAAGAT CGTTTTTCAT ATCGGAATGA GGATTTTATT      60
TATTCTTTTA AAAATAAAGA GGTGTTGAGC TAAACAATTT CAAATCTCAT CACACATATG     120
GGGTCAGCCA CAAAAATAAA GAACGGTTGG AACGGATCTA TTATATAATA CTAATAAAGA     180
```

| | | | | | | |
|---|---|---|---|---|---|---|
| ATAGAAAAAG | GAAAGTGAGT | GAGGTGCGAG | GGAGAGAATC | TGTTTACTAT | CAGAGTCGAT | 240 |
| CATGTGTCAG | TTTTATCGAT | ATGACTCTGA | CTTCAACTGA | GTTAAGCAA | TTCTGATAAG | 300 |
| GCGAGGAAAA | TCACAGTGCT | GAATCTAGAA | AAATCTCATA | GTGTGAGATA | AGTCTCAACA | 360 |
| AAAACGTTGA | GTCCATAGAG | GGGGTGTATG | TGACACCCCA | ACCTCAGCAA | AAGAAAACCT | 420 |
| CCCCTCAAGA | AGGACATTTG | CGGTGCTAAA | CAATTTCAAG | TCTCATCACA | CATATATATT | 480 |
| ATATAATACT | AATAAAGAAT | AGAAAAGGA | AAGGTAAACA | TCACTAATGA | CAGTTGCGGT | 540 |
| GCAAAGTGAG | TGAGATAATA | AACATCAGTA | ATAGACATCA | CTAACTTTTA | TTGGTTATGT | 600 |
| CAAACTCAAA | ATAAAATTTC | TCAACTTGTT | TACGTGCCTA | TATATACCAT | GCTTGTTATA | 660 |
| TGCTCAAAGC | ACCAACAAAA | TTTAAAAACA | ATTTGAACAT | TTGCAAAACT | AGTATGGG | 718 |

( 2 ) INFORMATION FOR SEQ ID NO:22:

( i ) SEQUENCE CHARACTERISTICS:
        ( A ) LENGTH: 703 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:22:

| | | | | | | |
|---|---|---|---|---|---|---|
| ATTTGTCAAA | TCAGGCTCAA | AGATCGTTTT | TCATATCGGA | ATGAGGATTT | TATTTATTCT | 60 |
| TTTAAAAATA | AAGAGGTGTT | GAGCTAAACA | ATTTCAAATC | TCATCACACA | TATGGGGTCA | 120 |
| GCCACAAAAA | TAAAGAACGG | TTGGAACGGA | TCTATTATAT | AATACTAATA | AAGAATAGAA | 180 |
| AAAGGAAAGT | GAGTGAGGTG | CGAGGGAGAG | AATCTGTTTA | CTATCAGAGT | CGATCATGTG | 240 |
| TCAGTTTTAT | CGATATGACT | CTGATTTCAA | CTGAGTTTAA | GCAATTCTGA | TAAGGCGAGG | 300 |
| AAAATCACAG | TGCTGAAATC | TAGAAAAATC | TCATAGTGTG | AGATAAGTCT | CAACAAAAAC | 360 |
| GTTGAGTCCA | TAGAGGGGGT | GTATGTGACA | CCCCAACCTC | AGCAAAAGAA | AACCTCCCCT | 420 |
| CAAGAAGGAC | ATTTGCGGTG | CTAAACAATT | TCAAGTCTCA | TCACACATAT | ATATTATATA | 480 |
| ATACTAATAA | AGAATAGAAA | AAGGAAAGGT | AAACATCACT | AATGACAGTT | GCGGTGCAAA | 540 |
| GTGAGTGAGA | TAATAAACAT | CAGTAATAGA | CATCACTAAC | TTTTATTGGT | TATGTCAAAC | 600 |
| TCAAAATAAA | ATTTCTCAAC | TTGTTTACGT | GCCTATATAT | ACCATGCTTG | TTATATGCTC | 660 |
| AAAGCACCAA | CAAAATTTAA | AAACAATTTG | AACATTTGCA | AAA | | 703 |

( 2 ) INFORMATION FOR SEQ ID NO:23:

( i ) SEQUENCE CHARACTERISTICS:
        ( A ) LENGTH: 650 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:23:

| | | | | | | |
|---|---|---|---|---|---|---|
| CTCGAGATTT | GTCAAATCAG | GCTCAAAGAT | CGTTTTCAT | ATCGGAATGA | GGATTTTATT | 60 |
| TATTCTTTTA | AAATAAAGA | GGTGGTGAGC | TAAACAATTT | CAAATCTCAT | CACACATATG | 120 |
| GGGTCAGCCA | CAAAAATAAA | GAACGGTTGG | AACGGATCTA | TTATATAATA | CTAATAAAGA | 180 |
| ATAGGAAAAG | GAAAGTGAGT | GAGGTGCGAG | GGAGAGAATT | TGTTTAATAT | CAGAGTCGAT | 240 |

| | | | | | |
|---|---|---|---|---|---|
|CATGTGTCAG|TTTTATCGAT|ATGATTCTGA|CTTCAACTGA|GTTAAGCAA|TTCTGATAAG| 300
|GCGGAGAAAA|TCATAGTGCT|GAGTCTAGAA|AAATCTCATG|CAGTGTGAGA|TAAACCTCAA| 360
|CAAGAACATT|TGCGGTGCTA|ACAATTTCA|AGTCTTATCA|CACATATATA|TTATATATTA| 420
|CTAATAAAGA|ATAGAAAAG|GAAAGGTAAA|CATCACTAAT|GACAGTTGCG|GTGCAAAGTG| 480
|AGTGAGATAA|TAAACATCAC|TAATAGACAT|CACTAACTTT|TATTGGTTAT|GTCAAACTCA| 540
|AAATAAAATT|TCTCAACTTG|TTTACGTGCC|TATATATACC|ATGCTTGTTA|TATGCTCAAA| 600
|GCACCAACAA|AATTTAAAAA|CAATTTGAAC|ATTTGCAAAA|CTAGTATGGG| | 650

( 2 ) INFORMATION FOR SEQ ID NO:24:

( i ) SEQUENCE CHARACTERISTICS:
    ( A ) LENGTH: 703 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:24:

| | | | | | |
|---|---|---|---|---|---|
|ATTTGTCAAA|TCAGGCTCAA|AGATCGTTTT|TCATATCGGA|ATGAGGATTT|TATTTATTCT| 60
|TTTAAAAATA|AAGAGGTGTT|GAGCTAAACA|ATTTCAAATC|TCATCACACA|TATGGGGTCA| 120
|GCCACAAAAA|TAAAGAACGG|TTGGAACGGA|TCTATTATAT|AATACTAATA|AAGAATAGAA| 180
|AAAGGAAAGT|GAGTGAGGTG|CGAGGGAGAG|AATCTGTTTA|CTATCAGAGT|CGATCATGTG| 240
|TCAGTTTTAT|CGATATGACT|CTGATTTCAA|CTGAGTTTAA|GCAATTCTGA|TAAGGCGAGG| 300
|AAAATCACAG|TGCTGAAATC|TAGAAAAATC|TCATAGTGTG|AGATAAGTCT|CAACAAAAAC| 360
|GTTGAGTCCA|TAGAGGGGT|GTATGTGACA|CCCCAACCTC|AGCAAAGAA|AACCTCCCCT| 420
|CAAGAAGGAC|ATTTGCGGTG|CTAAACAATT|TCAAGTCTCA|TCACACATAT|ATATTATATA| 480
|ATACTAATAA|AGAATAGAAA|AAGGAAAGGT|AAACATCACT|AATGACAGTT|GCGGTGCAAA| 540
|GTGAGTGAGA|TAATAAACAT|CAGTAATAGA|CATCACTAAC|TTTATTGGT|TATGTCAAAC| 600
|TCAAAATAAA|ATTTCTCAAC|TTGTTTACGT|GCCTATATAT|ACCATGCTTG|TTATATGCTC| 660
|AAAGCACCAA|CAAAATTTAA|AAACAATTTG|AACATTTGCA|AAA| | 703

( 2 ) INFORMATION FOR SEQ ID NO:25:

( i ) SEQUENCE CHARACTERISTICS:
    ( A ) LENGTH: 2000 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:25:

| | | | | | |
|---|---|---|---|---|---|
|GGATCCATTA|GGACTAGATA|ATGAAAAGAA|ACCGTTTTTT|TAATACCTCG|GCTGCTATTG| 60
|CCATTTCGAT|TGCATTAAAT|ACTTTTTTT|GTAGCATGCA|GACGATTGCT|GCTGAACCAG| 120
|AAGAAACTTA|TCTTGATTTT|CGTAAGGAGA|CGATATATTT|TCTATTCCTT|GATCGTTTCA| 180
|GCGATGGAGA|TCCAAGTAAT|AATGCAGGGT|TTAATTCTGC|AACCTACGAT|CCTAATAATT| 240
|TAAAAAAATA|TACTGGAGGA|GATCTCCGGG|GGTTGATTAA|TAAACTACCC|TATTTAAAAT| 300
|CACTTGGTGT|TACTTCAATC|TGGATTACTC|CCCCAATCGA|TAATGTGAAT|AATACTGATG| 360

```
CTGCTGGCAA TACTGGATAT CATGGTTATT GGGGAAGAGA TTATTTTCGT ATAGATGAAC      420
ATTTTGGCAA TCTCGATGAT TTCAAAGAAC TGACTAGTTT GATGCATAGT CCTGATTATA      480
ATATGAAACT GGTTCTTGAT TATGCCCCTA ATCATTCGAA TGCTAATGAT GAAAATGAAT      540
TTGGTGCACT ATATCGTGAT GGTGTGTTTA TTACTGATTA TCCTACAGAT GTTGCCGCCA      600
ATACGGGCTG GTATCATCAC AATGGTGGGG TAACGAACTG GAATGATTTC TTCCAAGTGA      660
AGAATCATAA TCTATTCAAT CTATCAGACC TCAATCAATC CAATACTGAT GTCTACCAGT      720
ACTTGTTGGA TGGCTCTAAA TTTTGGATCG ATGCTGGTGT GGATGCTATC AGGATTGATG      780
CCATCAAGCA TATGGACAAG TCTTTTATAC AGAAATGGAC CAGCGATATT TATGATTACA      840
GTAAGTCTAT CGGCCGGGAA GGATTTTTTT CTTCGGTGA ATGGTTGGT GCCAGTGCGA        900
ATACTACAAC AGGTGTTGAT GGTAATGCTA TCGATTACGC CAACACTTCC GGGTCAGCGT      960
TGCTGGATTT TGGATTCCGC GATACTTTAG AAAGAGTTTT GGTAGGACGT AGCGGAAATA     1020
CAATGAAAAC GTTAAATAGT TATCTGATAA AAAGACAAAC AGTCTTTACC AGTGATGACT     1080
GGCAGGTTGT TTTTATGGAT AACCATGATA TGGCACGCAT TGGTACCGCT CTGCGTTCAA     1140
ACGCCACTAC TTTTGGTCCT GGAAATAATG AAACCGGTGG AAGTCAGAGT GAAGCTTTTG     1200
CTCAGAAACG TATAGACCTC GGTCTGGTTG CGACAATGAC TGTACGTGGT ATTCCTGCCA     1260
TTTATTATGG TACTGAACAT TATGCCGCTA ACTTTACCTC TAACAGTTTT GGTCAAGTTG     1320
GCAGTGATCC TTACAACCGA GAGAAAATGC CAGGATTTGA TACGGAAAGT GAGGCTTTCT     1380
CCATTATTAA AACACTGGGT GACCTAAGGA AAAGTAGCCC GGCAATTCAA AATGGAACTT     1440
ATACTGAACT ATGGGTTAAT GATGATATAT TAGTATTTGA GCGGCGTTCT GGGAACGATA     1500
TTGTTATTGT TGCACTTAAT CGTGGTGAGG CTAACACAAT TAATGTTAAA AATATAGCGG     1560
TTCCTAATGG GGTATATCCG AGTTTGATTG GGAATAATAG TGTTTCAGTA GCAAATAAAC     1620
AGGCAACACT AACACTTATG CAAAATGAAG CTGTTGTCAT TCGCTCACAA TCAGATGATG     1680
CGGAGAACCC TACAGTACAA AGCATAAACT TCGCATGTAA TAACGGTTAT ACGATTTCAG     1740
GTCAAAGTGT TTATATTATT GGTAATATAC CTCAGTTAGG TGGTTGGGAC TTAACTAAAG     1800
CGGTAAAAAT ATCACCGACA CAATATCCAC AATGGAGTGC GAGCTTAGAG CTTCCTTCTG     1860
ACTTAAATGT TGAATGGAAG TGTGTGAAAC GTAATGAAAC CAATCCGACG GCTAATGTTG     1920
AGTGGCAGTC TGGTGCAAAT AACCAGTTCA ATAGCAATGA CACACAAACA ACGAATGGCT     1980
CGTTTTAATT AAAAGTCGAC                                                 2000
```

( 2 ) INFORMATION FOR SEQ ID NO:26:

( i ) SEQUENCE CHARACTERISTICS:
        ( A ) LENGTH: 1988 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO.

( x i ) SEQUENCE DESCRIPTION: SEQ ID NO:26:

```
ATTAGGACTA GATAATGAAA AGAAACCGTT TTTTAATAC CTCGGCTGCT ATTGCCATTT       60
CGATTGCATT AAATACTTTT TTTGTAGCA TGCAGACGAT TGCTGCTGAA CCAGAAGAAA      120
CTTATCTTGA TTTTCGTAAG GAGACGATAT ATTTTCTATT CCTTGATCGT TTCAGCGATG    180
GAGATCCAAG TAATAATGCA GGGTTTAATT CTGCAACCTA CGATCCTAAT AATTTAAAAA    240
```

-continued

| | | | | | |
|---|---|---|---|---|---|
| AATATACTGG | AGGAGATCTC | CGGGGGTTGA | TTAATAAACT | ACCCTATTTA | AAATCACTTG | 300
| GTGTTACTTC | AATCTGGATT | ACTCCCCCAA | TCGATAATGT | GAATAATACT | GATGCTGCTG | 360
| GCAATACTGG | ATATCATGGT | TATTGGGGAA | GAGATTATTT | TCGTATAGAT | GAACATTTTG | 420
| GCAATCTCGA | TGATTTCAAA | GAACTGACTA | GTTTGATGCA | TAGTCCTGAT | TATAATATGA | 480
| AACTGGTTCT | TGATTATGCC | CCTAATCATT | CGAATGCTAA | TGATGAAAAT | GAATTTGGTG | 540
| CACTATATCG | TGATGGTGTG | TTTATTACTG | ATTATCCTAC | GAATGTTGCC | GCCAATACGG | 600
| GCTGGTATCA | TCACAATGGT | GGGGTAACGA | ACTGGAATGA | TTTCTTCCAA | GTGAAGAATC | 660
| ATAATCTATT | CAATCTATCA | GACCTCAATC | AATCCAATAC | TGATGTCTAC | CAGTACTTGT | 720
| TGGATGGTTC | TAAATTTTGG | ATCGATGCTG | GTGTGGATGC | TATCAGGATT | GATGCCATCA | 780
| AGCATATGGA | CAAGTCTTTT | ATACAGAAAT | GGACCAGCGA | TATTATGAT | TACAGTAAGT | 840
| CTATCGGCCG | GAAGGATTT | TTTTCTTCG | GTGAATGGTT | TGGTGCCAGT | GCGAATACTA | 900
| CAACAGGTGT | TGATGGTAAT | GCTATCGATT | ACGCCAACAC | TTCCGGGTCA | GCGTTGCTGG | 960
| ATTTTGGATT | CCGCGATACT | TTAGAAAGAG | TTTTGGTAGG | ACGTAGCGGA | AATACAATGA | 1020
| AAACGTTAAA | TAGTTATCTG | ATAAAAAGAC | AAACAGTCTT | TACCAGTGAT | GACTGGCAGG | 1080
| TTGTTTTTAT | GGATAACCAT | GATATGGCAC | GCATTGGTAC | CGCTCTGCGT | TCAAACGCCA | 1140
| CTACTTTTGG | TCCTGGAAAT | AATGAAACCG | GTGGAAGTCA | GAGTGAAGCT | TTGCTCAGA | 1200
| AACGTATAGA | CCTCGGTCTG | GTTGCGACAA | TGACTGTACG | TGGTATTCCT | GCCATTTATT | 1260
| ATGGTACTGA | ACATTATGCC | GCTAACTTTA | CCTCTAACAG | TTTTGGTCAA | GTTGGCAGTG | 1320
| ATCCTTACAA | CCGAGAGAAA | ATGCCAGGAT | TGATACGGA | AAGTGAGGCT | TTCTCCATTA | 1380
| TTAAAACACT | GGGTGACCTA | AGGAAAAGTA | GCCCGGCAAT | TCAAAATGGA | ACTTATACTG | 1440
| AACTATGGGT | TAATGATGAT | ATATTAGTAT | TTGAGCGGCG | TTCTGGGAAC | GATATTGTTA | 1500
| TTGTTGCACT | TAATCGTGGT | GAGGCTAACA | CAATTAATGT | TAAAAATATA | GCGGTTCCTA | 1560
| ATGGGGTATA | TCCGAGTTTG | ATTGGGAATA | ATAGTGTTTC | AGTAGCAAAT | AAACGGACAA | 1620
| CACTAACACT | TATGCAAAAT | GAAGCTGTTG | TCATTCGCTC | ACAATCAGAT | GATGCGGAGA | 1680
| ACCCTACAGT | ACAAAGCATA | AACTTCACAT | GTAATAACGG | TTATACGATT | TCAGGTCAAA | 1740
| GTGTTTATAT | TATTGGTAAT | ATACCTCAGT | TAGGTGGTTG | GGACTTAACT | AAAGCGGTAA | 1800
| AAATATCACC | GACACAATAT | CCACAATGGA | GTGCGAGCTT | AGAGCTTCCT | TCTGACTTAA | 1860
| ATGTTGAATG | GAAGTGTGTG | AAACGTAATG | AAACCAATCC | GACGGCTAAT | GTTGAGTGGC | 1920
| AGTCTGGTGC | AAATAACCAG | TTCAATAGCA | ATGACACACA | AACAACGAAT | GGCTCGTTTT | 1980
| AATTAAAA | | | | | | 1988

( 2 ) INFORMATION FOR SEQ ID NO:27:

( i ) SEQUENCE CHARACTERISTICS:
        ( A ) LENGTH: 655 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:27:

```
Met Lys Arg Asn Arg Phe Phe Asn Thr Ser Ala Ala Ile Ala Ile Ser
 1               5                  10                  15

Ile Ala Leu Asn Thr Phe Phe Cys Ser Met Gln Thr Ile Ala Ala Glu
             20                  25                  30
```

-continued

```
Pro Glu Glu Thr Tyr Leu Asp Phe Arg Lys Glu Thr Ile Tyr Phe Leu
    35                  40                  45
Phe Leu Asp Arg Phe Ser Asp Gly Asp Pro Ser Asn Asn Ala Gly Phe
        50                  55                  60
Asn Ser Ala Thr Tyr Asp Pro Asn Asn Leu Lys Lys Tyr Thr Gly Gly
65                  70                  75                  80
Asp Leu Arg Gly Leu Ile Asn Lys Leu Pro Tyr Leu Lys Ser Leu Gly
                85                  90                  95
Val Thr Ser Ile Trp Ile Thr Pro Pro Ile Asp Asn Val Asn Asn Thr
            100                 105                 110
Asp Ala Ala Gly Asn Thr Gly Tyr His Gly Tyr Trp Gly Arg Asp Tyr
        115                 120                 125
Phe Arg Ile Asp Glu His Phe Gly Asn Leu Asp Phe Lys Glu Leu
    130                 135                 140
Thr Ser Leu Met His Ser Pro Asp Tyr Asn Met Lys Leu Val Leu Asp
145                 150                 155                 160
Tyr Ala Pro Asn His Ser Asn Ala Asn Asp Glu Asn Glu Phe Gly Ala
                165                 170                 175
Leu Tyr Arg Asp Gly Val Phe Ile Thr Asp Tyr Pro Thr Asp Val Ala
            180                 185                 190
Ala Asn Thr Gly Trp Tyr His His Asn Gly Gly Val Thr Asn Trp Asn
        195                 200                 205
Asp Phe Phe Gln Val Lys Asn His Asn Leu Phe Asn Leu Ser Asp Leu
    210                 215                 220
Asn Gln Ser Asn Thr Asp Val Tyr Gln Tyr Leu Leu Asp Gly Ser Lys
225                 230                 235                 240
Phe Trp Ile Asp Ala Gly Val Asp Ala Ile Arg Ile Asp Ala Ile Lys
                245                 250                 255
His Met Asp Lys Ser Phe Ile Gln Lys Trp Thr Ser Asp Ile Tyr Asp
            260                 265                 270
Tyr Ser Lys Ser Ile Gly Arg Glu Gly Phe Phe Phe Gly Glu Trp
        275                 280                 285
Phe Gly Ala Ser Ala Asn Thr Thr Thr Gly Val Asp Gly Asn Ala Ile
    290                 295                 300
Asp Tyr Ala Asn Thr Ser Gly Ser Ala Leu Leu Asp Phe Gly Phe Arg
305                 310                 315                 320
Asp Thr Leu Glu Arg Val Leu Val Gly Arg Ser Gly Asn Thr Met Lys
                325                 330                 335
Thr Leu Asn Ser Tyr Leu Ile Lys Arg Gln Thr Val Phe Thr Ser Asp
            340                 345                 350
Asp Trp Gln Val Val Phe Met Asp Asn His Asp Met Ala Arg Ile Gly
        355                 360                 365
Thr Ala Leu Arg Ser Asn Ala Thr Thr Phe Gly Pro Gly Asn Asn Glu
    370                 375                 380
Thr Gly Gly Ser Gln Ser Glu Ala Phe Ala Gln Lys Arg Ile Asp Leu
385                 390                 395                 400
Gly Leu Val Ala Thr Met Thr Val Arg Gly Ile Pro Ala Ile Tyr Tyr
                405                 410                 415
Gly Thr Glu His Tyr Ala Ala Asn Phe Thr Ser Asn Ser Phe Gly Gln
            420                 425                 430
Val Gly Ser Asp Pro Tyr Asn Arg Glu Lys Met Pro Gly Phe Asp Thr
        435                 440                 445
Glu Ser Glu Ala Phe Ser Ile Ile Lys Thr Leu Gly Asp Leu Arg Lys
```

|       |       |       |       |       | 450   |       |       |       |       | 455   |       |       |       |       | 460   |       |       |       |       |
|-------|-------|-------|-------|-------|-------|-------|-------|-------|-------|-------|-------|-------|-------|-------|-------|-------|-------|-------|-------|
| Ser 465 | Ser | Pro | Ala | Ile | Gln 470 | Asn | Gly | Thr | Tyr | Thr 475 | Glu | Leu | Trp | Val | Asn 480 |
| Asp | Asp | Ile | Leu | Val 485 | Phe | Glu | Arg | Arg | Ser 490 | Gly | Asn | Asp | Ile | Val 495 | Ile |
| Val | Ala | Leu | Asn 500 | Arg | Gly | Glu | Ala | Asn 505 | Thr | Ile | Asn | Val | Lys 510 | Asn | Ile |
| Ala | Val | Pro 515 | Asn | Gly | Val | Tyr | Pro 520 | Ser | Leu | Ile | Gly | Asn 525 | Asn | Ser | Val |
| Ser | Val 530 | Ala | Asn | Lys | Gln 535 | Ala | Thr | Leu | Thr | Leu 540 | Met | Gln | Asn | Glu | Ala |
| Val 545 | Val | Ile | Arg | Ser | Gln 550 | Ser | Asp | Asp | Ala | Glu 555 | Asn | Pro | Thr | Val | Gln 560 |
| Ser | Ile | Asn | Phe | Ala 565 | Cys | Asn | Asn | Gly | Tyr 570 | Thr | Ile | Ser | Gly | Gln 575 | Ser |
| Val | Tyr | Ile | Ile 580 | Gly | Asn | Ile | Pro | Gln 585 | Leu | Gly | Gly | Trp | Asp 590 | Leu | Thr |
| Lys | Ala | Val 595 | Lys | Ile | Ser | Pro | Thr 600 | Gln | Tyr | Pro | Gln | Trp 605 | Ser | Ala | Ser |
| Leu | Glu 610 | Leu | Pro | Ser | Asp | Leu 615 | Asn | Val | Glu | Trp | Lys 620 | Cys | Val | Lys | Arg |
| Asn 625 | Glu | Thr | Asn | Pro | Thr 630 | Ala | Asn | Val | Glu | Trp 635 | Gln | Ser | Gly | Ala | Asn 640 |
| Asn | Gln | Phe | Asn | Ser 645 | Asn | Asp | Thr | Gln | Thr 650 | Thr | Asn | Gly | Ser | Phe 655 |       |

(2) INFORMATION FOR SEQ ID NO:28:

(i) SEQUENCE CHARACTERISTICS:
        (A) LENGTH: 655 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:28:

| Met 1 | Lys | Arg | Asn | Arg 5 | Phe | Phe | Asn | Thr | Ser 10 | Ala | Ala | Ile | Ala | Ile 15 | Ser |
| Ile | Ala | Leu | Asn 20 | Thr | Phe | Phe | Cys | Ser 25 | Met | Gln | Thr | Ile | Ala 30 | Ala | Glu |
| Pro | Glu | Glu 35 | Thr | Tyr | Leu | Asp | Phe 40 | Arg | Lys | Glu | Thr | Ile 45 | Tyr | Phe | Leu |
| Phe | Leu 50 | Asp | Arg | Phe | Ser | Asp 55 | Gly | Asp | Pro | Ser | Asn 60 | Asn | Ala | Gly | Phe |
| Asn 65 | Ser | Ala | Thr | Tyr | Asp 70 | Pro | Asn | Asn | Leu | Lys 75 | Lys | Tyr | Thr | Gly | Gly 80 |
| Asp | Leu | Arg | Gly | Leu 85 | Ile | Asn | Lys | Leu | Pro 90 | Tyr | Leu | Lys | Ser | Leu 95 | Gly |
| Val | Thr | Ser | Ile 100 | Trp | Ile | Thr | Pro | Pro 105 | Ile | Asp | Asn | Val | Asn 110 | Asn | Thr |
| Asp | Ala | Ala 115 | Gly | Asn | Thr | Gly | Tyr 120 | His | Gly | Tyr | Trp | Gly 125 | Arg | Asp | Tyr |
| Phe | Arg 130 | Ile | Asp | Glu | His | Phe 135 | Gly | Asn | Leu | Asp | Asp 140 | Phe | Lys | Glu | Leu |

| | | | | | | | | | | | | | | |
|---|---|---|---|---|---|---|---|---|---|---|---|---|---|---|
| Thr | Ser | Leu | Met | His | Ser | Pro | Asp | Tyr | Asn | Met | Lys | Leu | Val | Leu | Asp |
| 145 | | | | | 150 | | | | | 155 | | | | | 160 |
| Tyr | Ala | Pro | Asn | His | Ser | Asn | Ala | Asn | Asp | Glu | Asn | Glu | Phe | Gly | Ala |
| | | | | 165 | | | | | 170 | | | | | 175 | |
| Leu | Tyr | Arg | Asp | Gly | Val | Phe | Ile | Thr | Asp | Tyr | Pro | Thr | Asn | Val | Ala |
| | | | 180 | | | | | | 185 | | | | 190 | | |
| Ala | Asn | Thr | Gly | Trp | Tyr | His | His | Asn | Gly | Gly | Val | Thr | Asn | Trp | Asn |
| | | 195 | | | | | 200 | | | | | 205 | | | |
| Asp | Phe | Phe | Gln | Val | Lys | Asn | His | Asn | Leu | Phe | Asn | Leu | Ser | Asp | Leu |
| | 210 | | | | | 215 | | | | 220 | | | | | |
| Asn | Gln | Ser | Asn | Thr | Asp | Val | Tyr | Gln | Tyr | Leu | Leu | Asp | Gly | Ser | Lys |
| 225 | | | | | 230 | | | | | 235 | | | | | 240 |
| Phe | Trp | Ile | Asp | Ala | Gly | Val | Asp | Ala | Ile | Arg | Ile | Asp | Ala | Ile | Lys |
| | | | | 245 | | | | | 250 | | | | | 255 | |
| His | Met | Asp | Lys | Ser | Phe | Ile | Gln | Lys | Trp | Thr | Ser | Asp | Ile | Tyr | Asp |
| | | | 260 | | | | | 265 | | | | | 270 | | |
| Tyr | Ser | Lys | Ser | Ile | Gly | Arg | Glu | Gly | Phe | Phe | Phe | Phe | Gly | Glu | Trp |
| | | 275 | | | | | 280 | | | | | 285 | | | |
| Phe | Gly | Ala | Ser | Ala | Asn | Thr | Thr | Thr | Gly | Val | Asp | Gly | Asn | Ala | Ile |
| | 290 | | | | | 295 | | | | | 300 | | | | |
| Asp | Tyr | Ala | Asn | Thr | Ser | Gly | Ser | Ala | Leu | Leu | Asp | Phe | Gly | Phe | Arg |
| 305 | | | | | 310 | | | | | 315 | | | | | 320 |
| Asp | Thr | Leu | Glu | Arg | Val | Leu | Val | Gly | Arg | Ser | Gly | Asn | Thr | Met | Lys |
| | | | | 325 | | | | | 330 | | | | | 335 | |
| Thr | Leu | Asn | Ser | Tyr | Leu | Ile | Lys | Arg | Gln | Thr | Val | Phe | Thr | Ser | Asp |
| | | | 340 | | | | | 345 | | | | | 350 | | |
| Asp | Trp | Gln | Val | Val | Phe | Met | Asp | Asn | His | Asp | Met | Ala | Arg | Ile | Gly |
| | | 355 | | | | | 360 | | | | | 365 | | | |
| Thr | Ala | Leu | Arg | Ser | Asn | Ala | Thr | Thr | Phe | Gly | Pro | Gly | Asn | Asn | Glu |
| | 370 | | | | | 375 | | | | | 380 | | | | |
| Thr | Gly | Gly | Ser | Gln | Ser | Glu | Ala | Phe | Ala | Gln | Lys | Arg | Ile | Asp | Leu |
| 385 | | | | | 390 | | | | | 395 | | | | | 400 |
| Gly | Leu | Val | Ala | Thr | Met | Thr | Val | Arg | Gly | Ile | Pro | Ala | Ile | Tyr | Tyr |
| | | | | 405 | | | | | 410 | | | | | 415 | |
| Gly | Thr | Glu | His | Tyr | Ala | Ala | Asn | Phe | Thr | Ser | Asn | Ser | Phe | Gly | Gln |
| | | | 420 | | | | | 425 | | | | | 430 | | |
| Val | Gly | Ser | Asp | Pro | Tyr | Asn | Arg | Glu | Lys | Met | Pro | Gly | Phe | Asp | Thr |
| | | 435 | | | | | 440 | | | | | 445 | | | |
| Glu | Ser | Glu | Ala | Phe | Ser | Ile | Ile | Lys | Thr | Leu | Gly | Asp | Leu | Arg | Lys |
| | 450 | | | | | 455 | | | | | 460 | | | | |
| Ser | Ser | Pro | Ala | Ile | Gln | Asn | Gly | Thr | Tyr | Thr | Glu | Leu | Trp | Val | Asn |
| 465 | | | | | 470 | | | | | 475 | | | | | 480 |
| Asp | Asp | Ile | Leu | Val | Phe | Glu | Arg | Arg | Ser | Gly | Asn | Asp | Ile | Val | Ile |
| | | | | 485 | | | | | 490 | | | | | 495 | |
| Val | Ala | Leu | Asn | Arg | Gly | Glu | Ala | Asn | Thr | Ile | Asn | Val | Lys | Asn | Ile |
| | | | 500 | | | | | 505 | | | | | 510 | | |
| Ala | Val | Pro | Asn | Gly | Val | Tyr | Pro | Ser | Leu | Ile | Gly | Asn | Asn | Ser | Val |
| | | 515 | | | | | 520 | | | | | 525 | | | |
| Ser | Val | Ala | Asn | Lys | Arg | Thr | Thr | Leu | Thr | Leu | Met | Gln | Asn | Glu | Ala |
| | 530 | | | | | 535 | | | | | 540 | | | | |
| Val | Val | Ile | Arg | Ser | Gln | Ser | Asp | Asp | Ala | Glu | Asn | Pro | Thr | Val | Gln |
| 545 | | | | | 550 | | | | | 555 | | | | | 560 |
| Ser | Ile | Asn | Phe | Thr | Cys | Asn | Asn | Gly | Tyr | Thr | Ile | Ser | Gly | Gln | Ser |
| | | | | 565 | | | | | 570 | | | | | 575 | |

| | | | | | | | | | | | | | | |
|---|---|---|---|---|---|---|---|---|---|---|---|---|---|---|
| Val | Tyr | Ile | Ile 580 | Gly | Asn | Ile | Pro | Gln 585 | Leu | Gly | Gly | Trp | Asp 590 | Leu | Thr |
| Lys | Ala | Val 595 | Lys | Ile | Ser | Pro | Thr 600 | Gln | Tyr | Pro | Gln | Trp 605 | Ser | Ala | Ser |
| Leu | Glu 610 | Leu | Pro | Ser | Asp | Leu 615 | Asn | Val | Glu | Trp | Lys 620 | Cys | Val | Lys | Arg |
| Asn 625 | Glu | Thr | Asn | Pro | Thr 630 | Ala | Asn | Val | Glu | Trp 635 | Gln | Ser | Gly | Ala | Asn 640 |
| Asn | Gln | Phe | Asn | Ser 645 | Asn | Asp | Thr | Gln | Thr 650 | Thr | Asn | Gly | Ser | Phe 655 | |